US009351716B2

(12) United States Patent
Miles et al.

(10) Patent No.: US 9,351,716 B2
(45) Date of Patent: *May 31, 2016

(54) MEDICAL DEVICE AND DELIVERY SYSTEM FOR MODIFICATION OF LEFT ATRIAL APPENDAGE AND METHODS THEREOF

(75) Inventors: Scott D. Miles, Sandy, UT (US); Clark C. Davis, Holladay, UT (US); Daryl R. Edmiston, Draper, UT (US); Richard J. Linder, Sandy, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 428 days.

This patent is subject to a terminal disclaimer.

(21) Appl. No.: 13/450,755

(22) Filed: Apr. 19, 2012

(65) Prior Publication Data

US 2012/0316584 A1 Dec. 13, 2012

Related U.S. Application Data

(63) Continuation-in-part of application No. 12/818,059, filed on Jun. 17, 2010.

(60) Provisional application No. 61/477,075, filed on Apr. 19, 2011, provisional application No. 61/345,514,
(Continued)

(51) Int. Cl.
*A61B 17/00* (2006.01)
*A61B 17/12* (2006.01)

(52) U.S. Cl.
CPC ....... *A61B 17/0057* (2013.01); *A61B 17/12022* (2013.01); *A61B 17/12122* (2013.01);
(Continued)

(58) Field of Classification Search
CPC .............. A61B 17/0057; A61B 17/12022; A61B 17/12177; A61B 17/12122; A61B 17/12172
USPC .......................................... 606/200
See application file for complete search history.

(56) References Cited

U.S. PATENT DOCUMENTS 3,095,877 A 7/1963 Rowan
3,874,388 A 4/1975 King et al.
(Continued)

FOREIGN PATENT DOCUMENTS

CA 2627408 5/2008
DE 102006056283 A1 6/2008
(Continued)

OTHER PUBLICATIONS

International Search Report dated Jun. 15, 2009, for International Application No. PCT/US2008/080374 (7 pages).
(Continued)

*Primary Examiner* — Richard Louis
(74) *Attorney, Agent, or Firm* — David L. Stott

(57) ABSTRACT

Devices, methods and systems are provided for occluding an opening within the tissue of a body, such as a left atrial appendage. In one embodiment, a delivery system for use in occluding an opening in the tissue of a body includes an actuation assembly operatively coupled to a medical device including an anchor portion and an occluder portion. The actuation assembly is configured to move the anchor portion between a deployed state and retracted state while the occluder portion maintains a deployed state. With this arrangement, the deployed occluder portion can be visualized via imaging at a preferred position prior to deploying the anchor portion of the medical device.

17 Claims, 44 Drawing Sheets

Related U.S. Application Data filed on May 17, 2010, provisional application No. 61/325,230, filed on Apr. 16, 2010, provisional application No. 61/320,635, filed on Apr. 2, 2010, provisional application No. 61/294,058, filed on Jan. 11, 2010, provisional application No. 61/218,018, filed on Jun. 17, 2009.

(52) U.S. Cl.
CPC ..... *A61B17/12172* (2013.01); *A61B 17/12177* (2013.01); *A61B 2017/0053* (2013.01); *A61B 2017/0069* (2013.01); *A61B 2017/00309* (2013.01); *A61B 2017/00327* (2013.01); *A61B 2017/00575* (2013.01); *A61B 2017/12054* (2013.01)

(56) References Cited

U.S. PATENT DOCUMENTS

| | | | |
|---|---|---|---|
| 5,171,259 A | 12/1992 | Inoue | |
| 5,192,301 A | 3/1993 | Kamiya et al. | |
| 5,284,488 A | 2/1994 | Sideris | |
| 5,334,217 A | 8/1994 | Das | |
| 5,425,733 A | 6/1995 | Schmieding | |
| 5,425,740 A | 6/1995 | Hutchinson, Jr. | |
| 5,433,727 A | 7/1995 | Sideris | |
| 5,792,165 A | 8/1998 | Klieman et al. | |
| 5,861,003 A | 1/1999 | Latson et al. | |
| 5,904,703 A | 5/1999 | Gilson | |
| 5,910,154 A | 6/1999 | Tsugita et al. | |
| 5,992,158 A | 11/1999 | Goddard et al. | |
| 6,152,144 A | 11/2000 | Lesh et al. | |
| 6,174,322 B1 | 1/2001 | Schneidt | |
| 6,231,561 B1 | 5/2001 | Frazier et al. | |
| 6,238,403 B1 | 5/2001 | Greene, Jr. et al. | |
| 6,290,674 B1 | 9/2001 | Roue et al. | |
| 6,328,727 B1 | 12/2001 | Frazier et al. | |
| 6,355,051 B1 | 3/2002 | Sisskind et al. | |
| 6,371,971 B1 | 4/2002 | Tsugita et al. | |
| 6,398,760 B1 | 6/2002 | Danby | |
| 6,419,669 B1 | 7/2002 | Frazier et al. | |
| 6,436,088 B2 | 8/2002 | Frazier et al. | |
| 6,458,100 B2 | 10/2002 | Roue et al. | |
| 6,488,689 B1 | 12/2002 | Kaplan et al. | |
| 6,530,934 B1 | 3/2003 | Jacobsen et al. | |
| 6,551,303 B1 | 4/2003 | Van Tassel et al. | |
| 6,551,341 B2 | 4/2003 | Boylan et al. | |
| 6,561,969 B2 | 5/2003 | Frazier et al. | |
| 6,650,923 B1 | 11/2003 | Lesh et al. | |
| 6,651,557 B1 | 11/2003 | Costin et al. | |
| 6,652,555 B1 | 11/2003 | VanTassel et al. | |
| 6,652,556 B1 | 11/2003 | VanTassel et al. | |
| 6,666,861 B1 | 12/2003 | Grabek | |
| 6,689,150 B1 | 2/2004 | VanTassel et al. | |
| 6,702,825 B2 | 3/2004 | Frazier et al. | |
| 6,706,065 B2 | 3/2004 | Langberg et al. | |
| 6,712,804 B2 | 3/2004 | Roue et al. | |
| 6,730,108 B2 | 5/2004 | Van Tassel et al. | |
| 6,746,472 B2 | 6/2004 | Frazier et al. | |
| 6,790,229 B1 | 9/2004 | Berreklouw | |
| 6,949,113 B2 | 9/2005 | Van Tassel et al. | |
| 6,979,344 B2 | 12/2005 | Jones et al. | |
| 6,994,092 B2 | 2/2006 | van der Burg et al. | |
| 7,011,671 B2 | 3/2006 | Welch | |
| 7,014,645 B2 | 3/2006 | Greene, Jr. et al. | |
| 7,025,756 B2 | 4/2006 | Frazier et al. | |
| 7,044,134 B2 | 5/2006 | Khairkhahan et al. | |
| 7,056,294 B2 | 6/2006 | Khairkhahan et al. | |
| 7,115,110 B2 | 10/2006 | Frazier et al. | |
| 7,128,073 B1 | 10/2006 | van der Burg et al. | |
| 7,152,605 B2 | 12/2006 | Khairkhahan et al. | |
| 7,169,164 B2 | 1/2007 | Borillo et al. | |
| 7,192,439 B2 | 3/2007 | Khairkhahan et al. | |
| 7,226,458 B2 | 6/2007 | Kaplan et al. | |
| 7,293,562 B2 | 11/2007 | Malecki et al. | |
| 7,597,704 B2 | 10/2009 | Frazier et al. | |
| 7,608,091 B2 | 10/2009 | Goldfarb et al. | |
| 7,717,937 B2 | 5/2010 | Wahr et al. | |
| 7,727,189 B2 | 6/2010 | Van Tassel et al. | |
| 7,780,645 B2 | 8/2010 | Jones | |
| 7,842,054 B2 | 11/2010 | Greene, Jr. et al. | |
| 8,142,470 B2 | 3/2012 | Quinn et al. | |
| 8,740,934 B2 | 6/2014 | McGuckin, Jr. | |
| 2001/0003161 A1 | 6/2001 | Vardi et al. | |
| 2001/0037141 A1 | 11/2001 | Yee et al. | |
| 2002/0026094 A1 | 2/2002 | Roth | |
| 2002/0026217 A1 | 2/2002 | Baker et al. | |
| 2002/0062130 A1 | 5/2002 | Jugenheimer et al. | |
| 2002/0177855 A1 | 11/2002 | Greene, Jr. et al. | |
| 2002/0183787 A1 | 12/2002 | Wahr et al. | |
| 2003/0014075 A1 | 1/2003 | Rosenbluth et al. | |
| 2003/0055455 A1 | 3/2003 | Yang et al. | |
| 2003/0057156 A1 | 3/2003 | Peterson et al. | |
| 2003/0120337 A1 | 6/2003 | Van Tassel et al. | |
| 2003/0125790 A1 | 7/2003 | Fastovsky et al. | |
| 2003/0171739 A1 | 9/2003 | Murphy et al. | |
| 2003/0181942 A1 * | 9/2003 | Sutton et al. | 606/200 |
| 2003/0187474 A1 | 10/2003 | Keegan et al. | |
| 2003/0191526 A1 | 10/2003 | Van Tassel et al. | |
| 2003/0195555 A1 | 10/2003 | Khairkhahan et al. | |
| 2003/0199923 A1 | 10/2003 | Khairkhahan et al. | |
| 2003/0204203 A1 | 10/2003 | Khairkhahan et al. | |
| 2003/0212432 A1 | 11/2003 | Khairkhahan et al. | |
| 2003/0220667 A1 | 11/2003 | van der Burg et al. | |
| 2004/0034366 A1 | 2/2004 | van der Burg et al. | |
| 2004/0049224 A1 * | 3/2004 | Buehlmann et al. | 606/200 |
| 2004/0122467 A1 | 6/2004 | VanTassel et al. | |
| 2004/0127935 A1 * | 7/2004 | VanTassel et al. | 606/200 |
| 2004/0215230 A1 | 10/2004 | Frazier et al. | |
| 2004/0254594 A1 | 12/2004 | Alfaro | |
| 2004/0260317 A1 | 12/2004 | Bloom et al. | |
| 2004/0267191 A1 | 12/2004 | Gifford, III et al. | |
| 2005/0004652 A1 | 1/2005 | van der Burg et al. | |
| 2005/0033409 A1 | 2/2005 | Burke et al. | |
| 2005/0038470 A1 | 2/2005 | Van Der Burg et al. | |
| 2005/0043759 A1 * | 2/2005 | Chanduszko | 606/213 |
| 2005/0049573 A1 | 3/2005 | Van Tassel et al. | |
| 2005/0060017 A1 | 3/2005 | Fischell et al. | |
| 2005/0065589 A1 | 3/2005 | Schneider et al. | |
| 2005/0075665 A1 | 4/2005 | Brenzel et al. | |
| 2005/0090860 A1 | 4/2005 | Paprocki | |
| 2005/0113861 A1 | 5/2005 | Corcoran et al. | |
| 2005/0149173 A1 | 7/2005 | Hunter et al. | |
| 2005/0192616 A1 | 9/2005 | Callister et al. | |
| 2005/0192627 A1 | 9/2005 | Whisenant et al. | |
| 2005/0234540 A1 | 10/2005 | Peavey et al. | |
| 2005/0234543 A1 | 10/2005 | Glaser et al. | |
| 2005/0251144 A1 | 11/2005 | Wilson et al. | |
| 2005/0256532 A1 | 11/2005 | Nayak et al. | |
| 2005/0267524 A1 | 12/2005 | Chanduszko | |
| 2006/0000443 A1 * | 1/2006 | Kado et al. | 123/399 |
| 2006/0004433 A1 * | 1/2006 | Greenberg et al. | 623/1.11 |
| 2006/0009798 A1 | 1/2006 | Callister | |
| 2006/0009800 A1 | 1/2006 | Christianson et al. | |
| 2006/0036282 A1 | 2/2006 | Wahr et al. | |
| 2006/0052816 A1 | 3/2006 | Bates et al. | |
| 2006/0122646 A1 | 6/2006 | Corcoran et al. | |
| 2006/0149299 A1 | 7/2006 | Greene et al. | |
| 2006/0149307 A1 | 7/2006 | Durgin | |
| 2006/0149314 A1 | 7/2006 | Borillo et al. | |
| 2006/0155323 A1 | 7/2006 | Porter et al. | |
| 2006/0206148 A1 | 9/2006 | Khairkhahan et al. | |
| 2006/0217761 A1 | 9/2006 | Opolski | |
| 2006/0276839 A1 | 12/2006 | McGuckin, Jr. | |
| 2007/0073247 A1 | 3/2007 | Ewaschuk | |
| 2007/0083230 A1 | 4/2007 | Javois | |
| 2007/0083232 A1 | 4/2007 | Lee | |
| 2007/0088388 A1 | 4/2007 | Opolski et al. | |
| 2007/0112382 A1 | 5/2007 | Thill et al. | |
| 2007/0123934 A1 | 5/2007 | Whisenant et al. | |
| 2007/0129753 A1 | 6/2007 | Quinn et al. | |
| 2007/0129757 A1 | 6/2007 | Armstrong | |
| 2007/0135826 A1 | 6/2007 | Zaver et al. | |
| 2007/0149995 A1 * | 6/2007 | Quinn et al. | 606/194 |

(56) References Cited

U.S. PATENT DOCUMENTS

| | | |
|---|---|---|
| 2007/0167981 A1 | 7/2007 | Opolski et al. |
| 2007/0173885 A1 | 7/2007 | Cartier et al. |
| 2007/0179527 A1 | 8/2007 | Eskuri et al. |
| 2007/0179583 A1 | 8/2007 | Goetzinger et al. |
| 2007/0191884 A1 | 8/2007 | Eskridge et al. |
| 2007/0198059 A1 | 8/2007 | Patel et al. |
| 2007/0213766 A1 | 9/2007 | Ravikumar |
| 2007/0237720 A1 | 10/2007 | Padilla et al. |
| 2007/0270891 A1 | 11/2007 | McGuckin |
| 2007/0276415 A1 | 11/2007 | Kladakis et al. |
| 2008/0039929 A1 | 2/2008 | Davis et al. |
| 2008/0119891 A1 | 5/2008 | Miles et al. |
| 2008/0215086 A1 | 9/2008 | Olsen et al. |
| 2009/0025820 A1 | 1/2009 | Adams |
| 2009/0069840 A1 | 3/2009 | Hallisey |
| 2009/0099596 A1 | 4/2009 | McGuckin, Jr. et al. |
| 2009/0105747 A1 | 4/2009 | Chanduszko et al. |
| 2009/0112249 A1 | 4/2009 | Miles et al. |
| 2009/0171386 A1 * | 7/2009 | Amplatz et al. ............... 606/213 |
| 2009/0299338 A1 | 12/2009 | di Palma |
| 2009/0318948 A1 | 12/2009 | Linder et al. |
| 2010/0191279 A1 * | 7/2010 | Kassab et al. ................ 606/213 |
| 2010/0228279 A1 | 9/2010 | Miles et al. |
| 2010/0228285 A1 | 9/2010 | Miles et al. |
| 2010/0234878 A1 | 9/2010 | Hruska et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0022079 A1 | 1/2011 | Miles et al. |
| 2011/0046658 A1 | 2/2011 | Connor et al. |
| 2011/0054515 A1 | 3/2011 | Bridgeman et al. |
| 2011/0208233 A1 | 8/2011 | McGuckin, Jr. et al. |
| 2012/0316584 A1 | 12/2012 | Miles et al. |

FOREIGN PATENT DOCUMENTS

| | | |
|---|---|---|
| EP | 1266630 A1 | 12/2002 |
| EP | 1358850 A2 | 11/2003 |
| EP | 1523957 A2 | 4/2005 |
| EP | 1741393 A1 | 1/2007 |
| JP | 2008536620 | 9/2008 |
| JP | 2010500917 | 1/2010 |
| WO | 9933402 | 7/1999 |
| WO | 0027292 | 5/2000 |
| WO | 0193920 | 12/2001 |
| WO | 02071977 | 9/2002 |
| WO | 2003028802 | 4/2003 |
| WO | 2004045393 A2 | 6/2004 |
| WO | 2004/100803 | 11/2004 |
| WO | 2005053547 A2 | 6/2005 |
| WO | 2005099365 A2 | 10/2005 |
| WO | 2006033641 | 3/2006 |
| WO | 2006047748 A2 | 5/2006 |
| WO | 2007054116 | 5/2007 |
| WO | 2007/147145 | 12/2007 |
| WO | 2010081033 A1 | 7/2010 |
| WO | 2010148246 A2 | 12/2010 |

OTHER PUBLICATIONS

International Search Report dated May 6, 2010, for International Application No. PCT/US2010/020539 (5 pages).
International Search Report dated May 7, 2010, for International Application No. PCT/US2010/020547 (4 pages).
International Search Report dated Apr. 29, 2010, for International Application No. PCT/US2010/020549 (7 pages).
Office Action and English Translation issued in JP2012-516313 on Mar. 25, 2014.
English Abstract and English machine translation of the Specification and Claims of DE102006056283, Jun. 5, 2008.
International Search Report dated Feb. 7, 2013 for International Application No. PCT/US2012/063074 (5 pages).

* cited by examiner

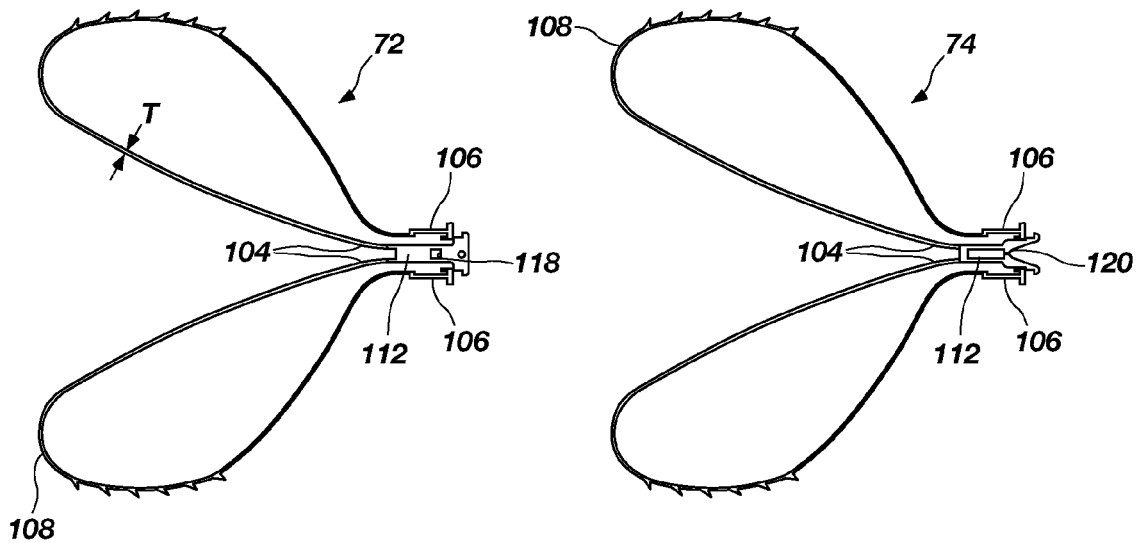
FIG. 6A  FIG. 6B
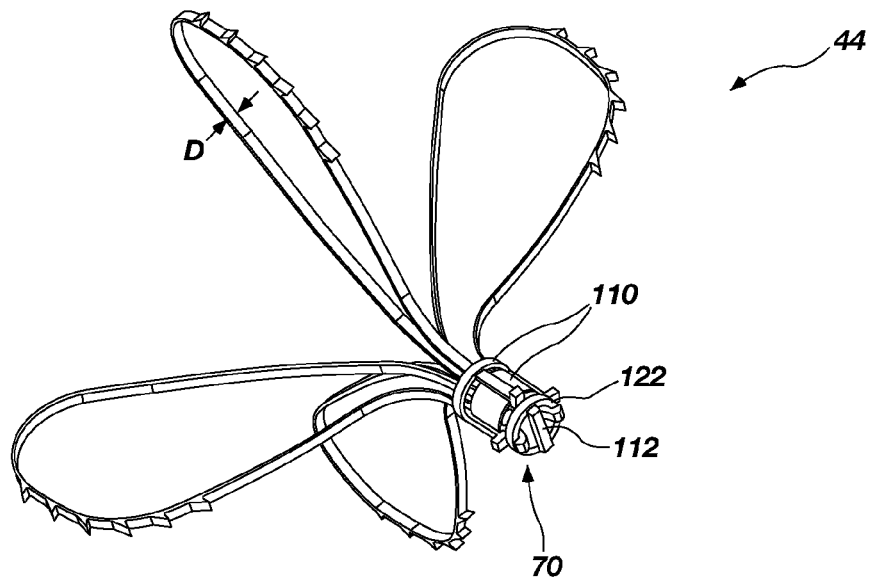
FIG. 6C

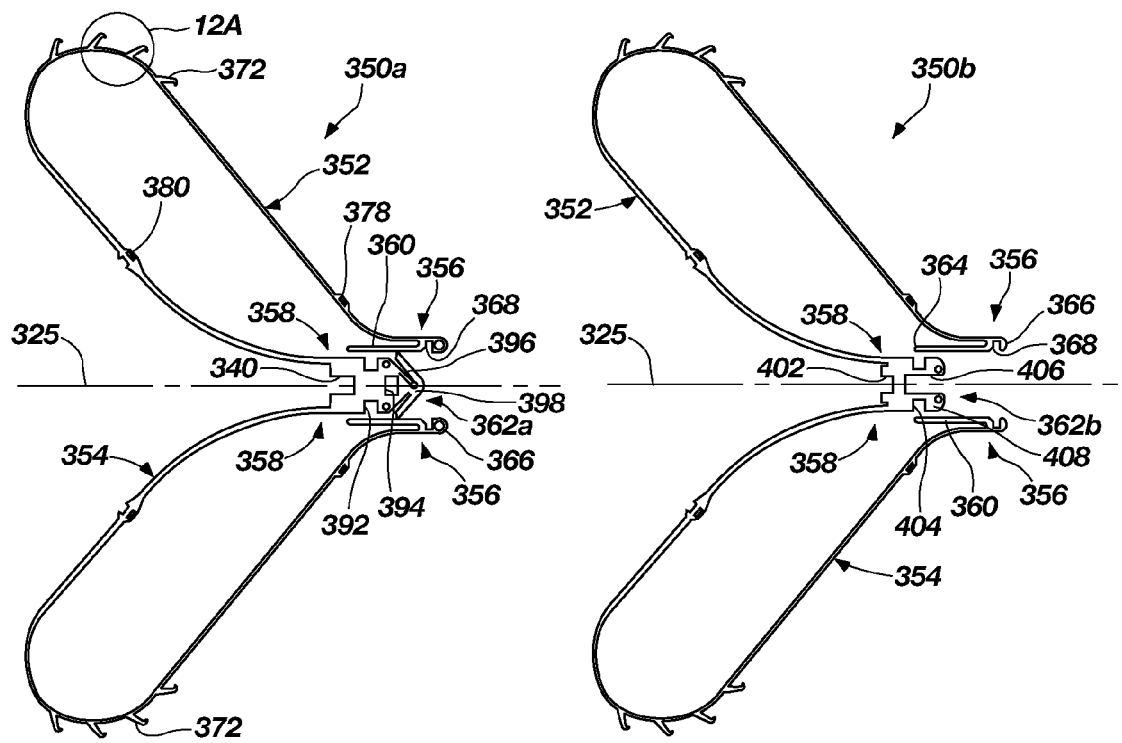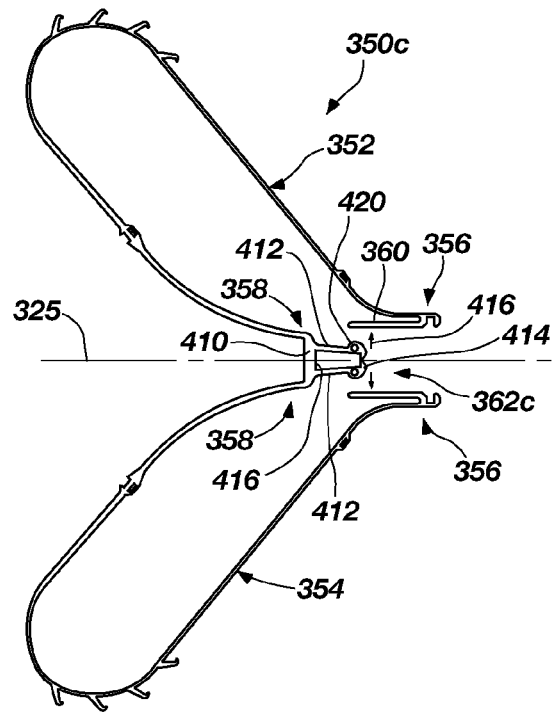
FIG. 11A
FIG. 11B
FIG. 11C

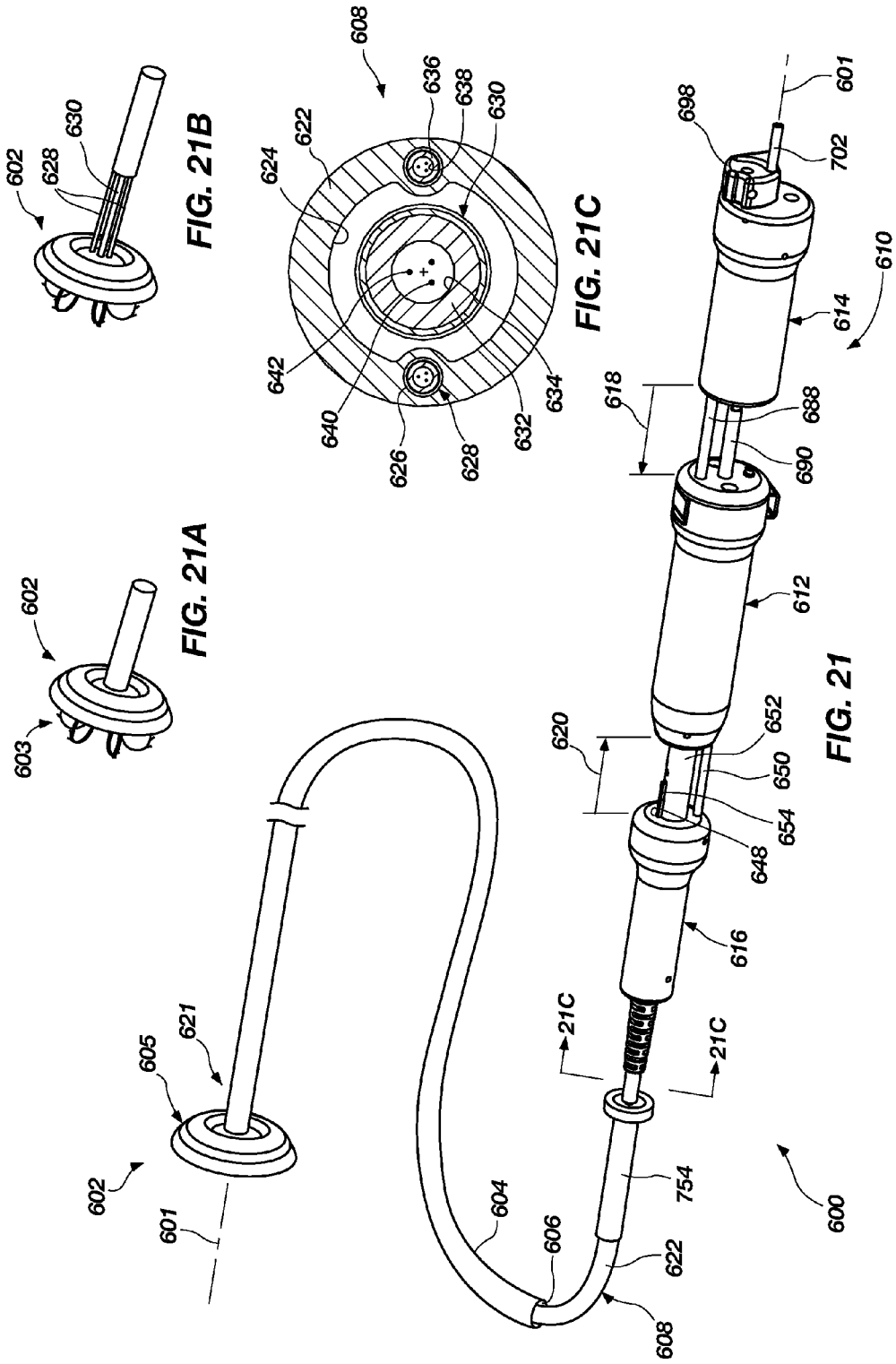

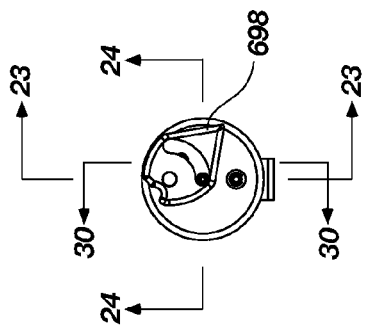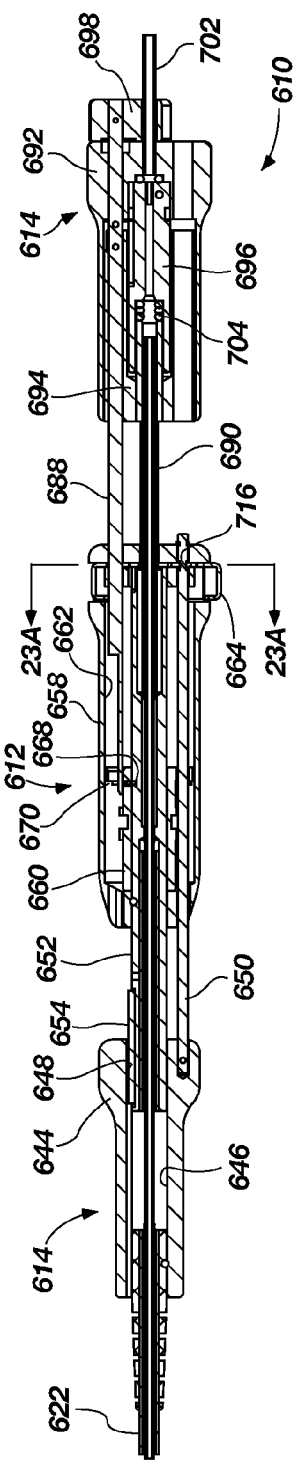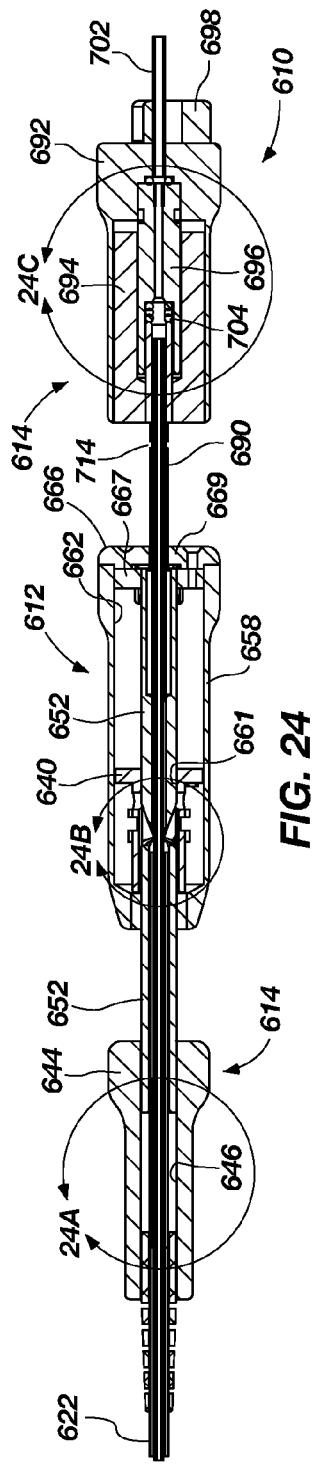

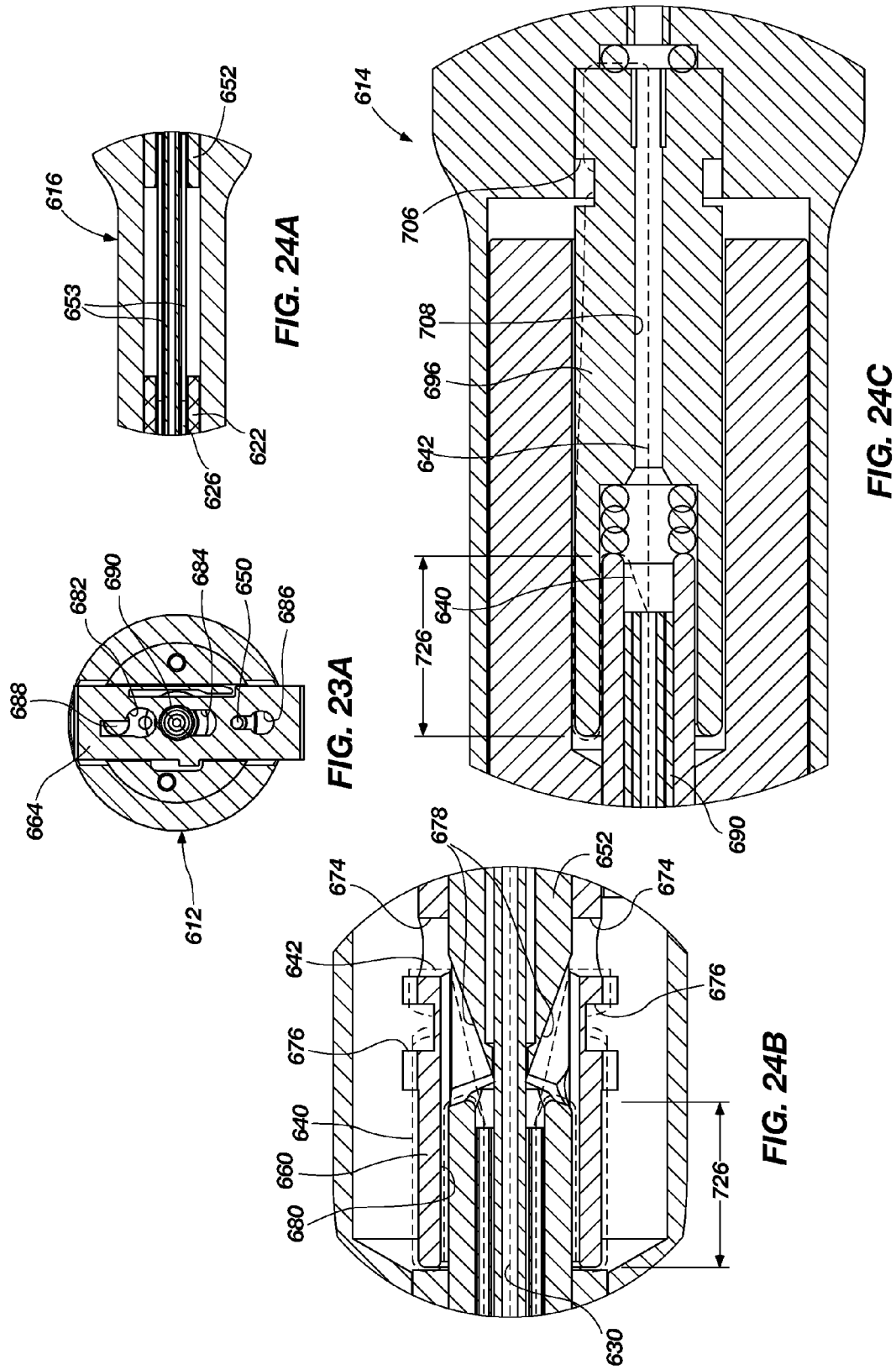

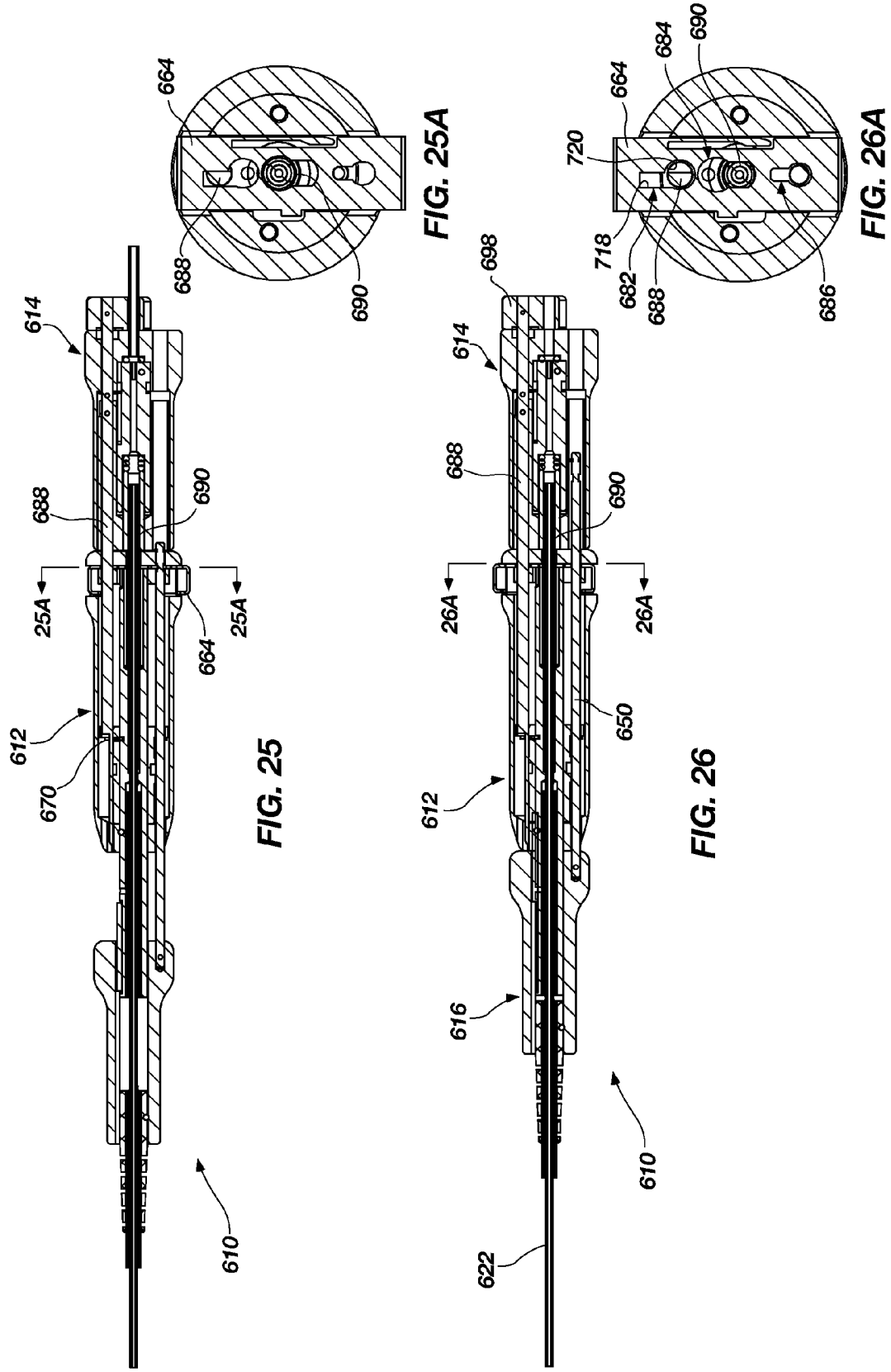

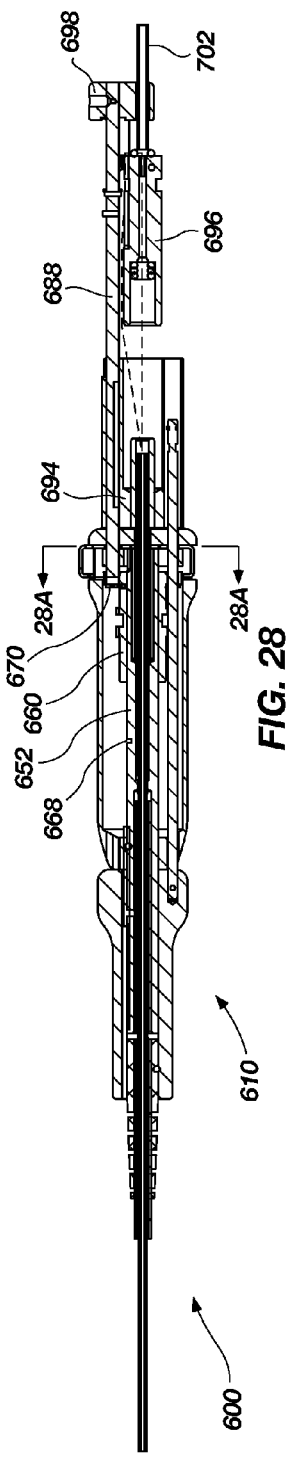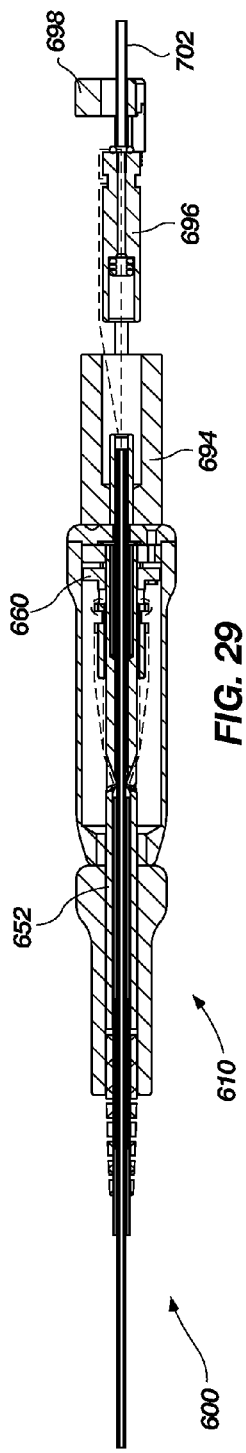

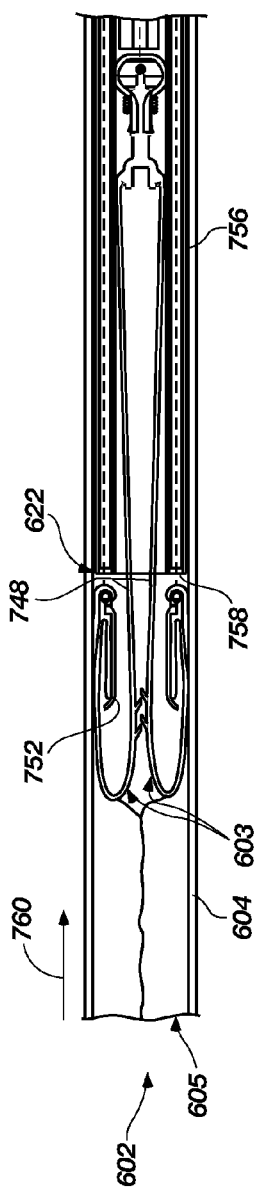
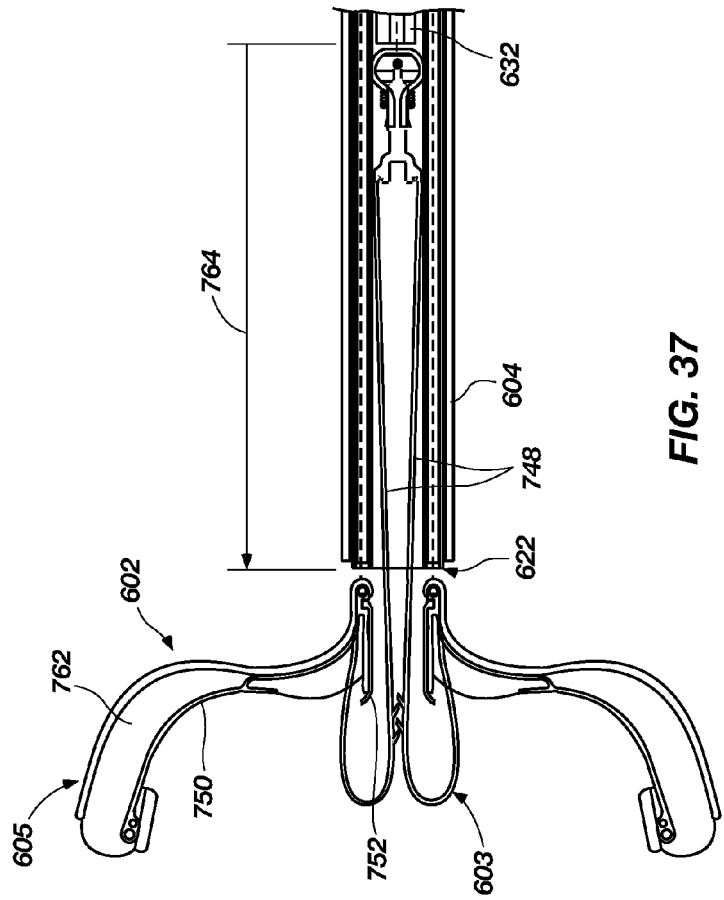
FIG. 36
FIG. 37

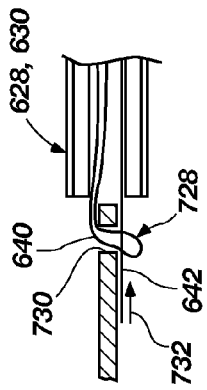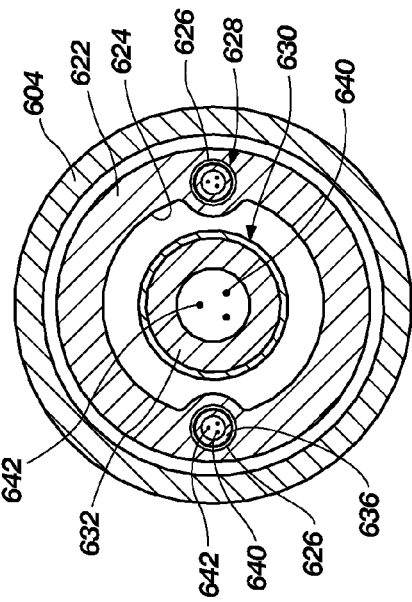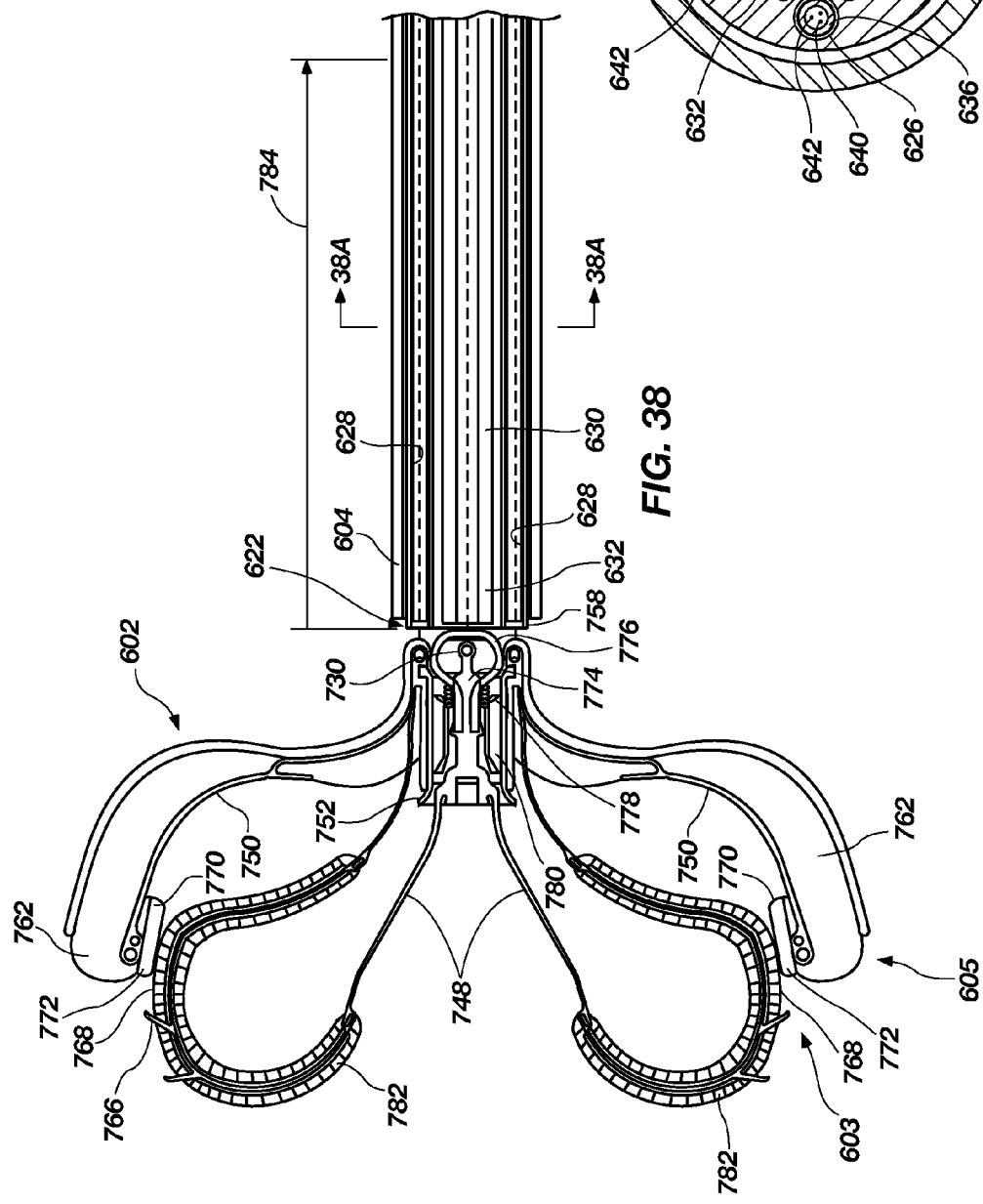

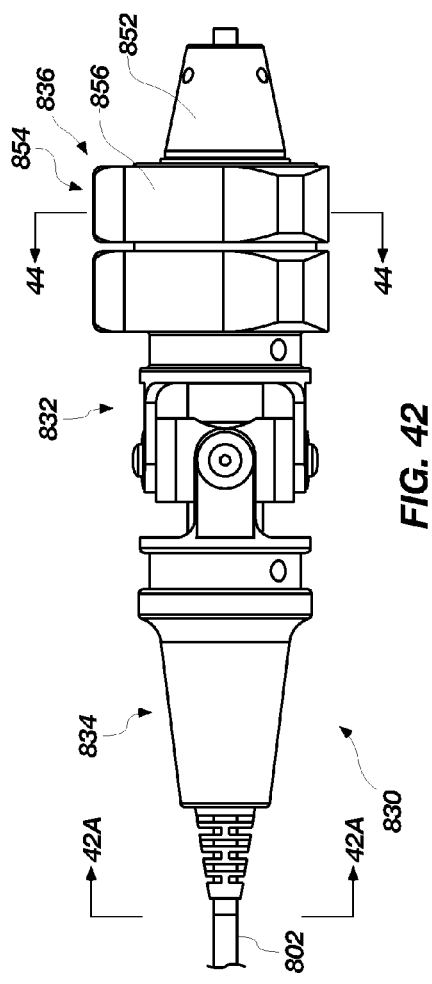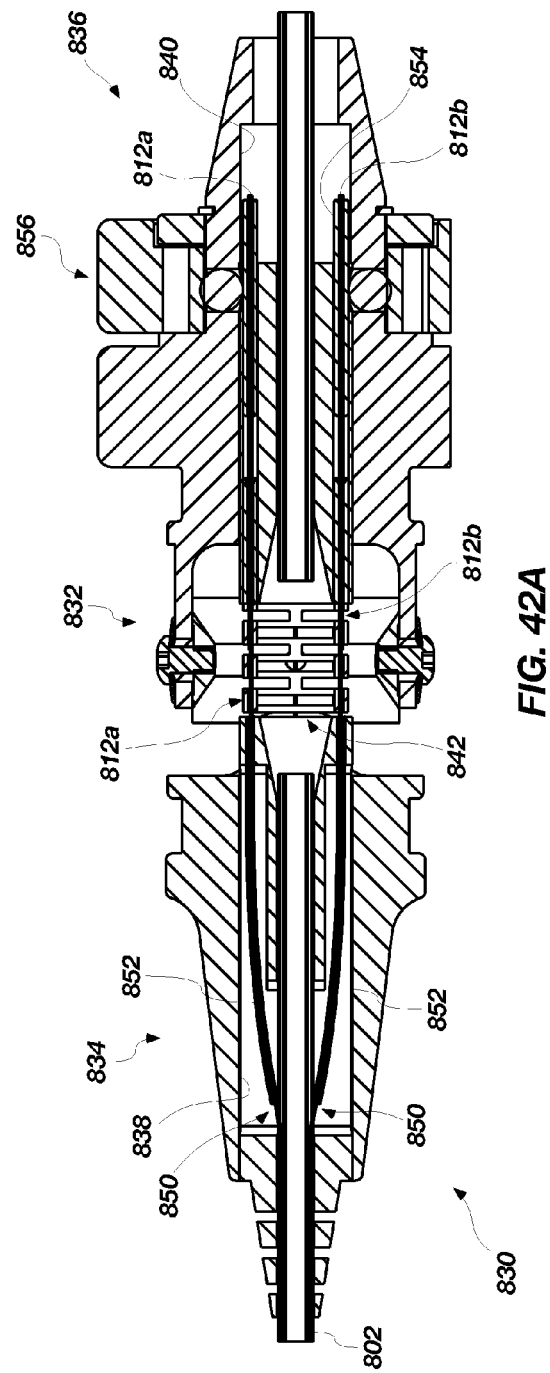

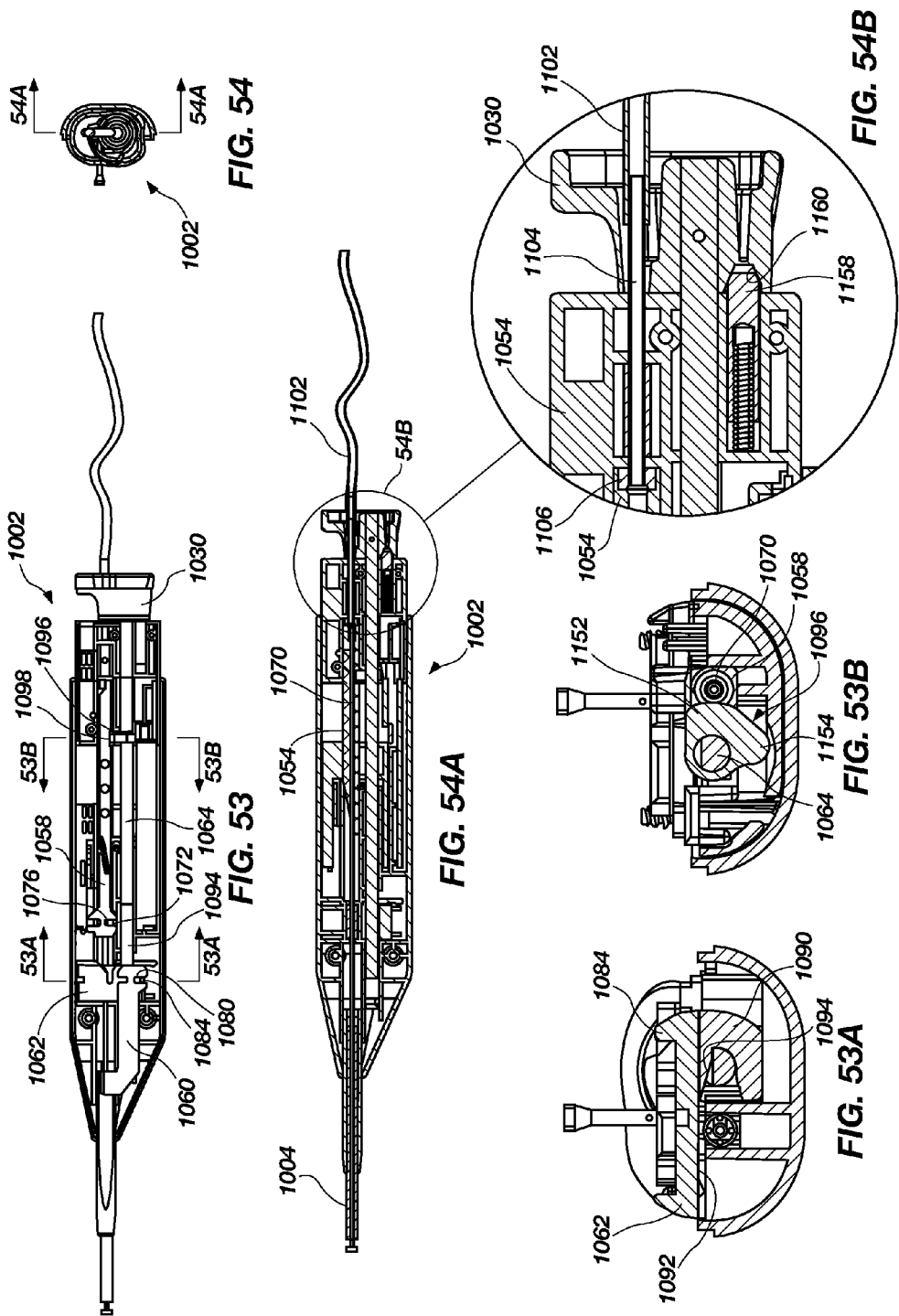

MEDICAL DEVICE AND DELIVERY SYSTEM FOR MODIFICATION OF LEFT ATRIAL APPENDAGE AND METHODS THEREOF

CROSS-REFERENCE TO RELATED APPLICATIONS

This application claims benefit to U.S. Provisional Patent Application No. 61/477,075, filed on Apr. 19, 2011. This application also claims benefit to, and is a continuation-in-part of, U.S. patent application Ser. No. 12/818,059, filed on Jun. 17, 2010, which in turn claims benefit to the following U.S. Provisional patent applications: U.S. Provisional Application No. 61/345,514, filed on May 17, 2010; U.S. Provisional Application No. 61/325,230, filed on Apr. 16, 2010; U.S. Provisional Application No. 61/320,635, filed on Apr. 2, 2010; U.S. Provisional Application No. 61/294,058, filed on Jan. 11, 2010; and U.S. Provisional Application No. 61/218, 018, filed on Jun. 17, 2009. The disclosures of each application listed above are incorporated by reference herein in their entireties.

TECHNICAL FIELD

The present invention relates generally to the occlusion or modification of tissue openings or appendages and, more specifically, to devices, systems and methods for occluding or otherwise structurally altering such openings and appendages including, for example, left atrial appendages.

BACKGROUND

The upper chambers of the heart, the atria, have appendages attached to each of them. For example, the left atrial appendage is a feature of all human hearts. The physiologic function of such appendages is not completely understood, but they do act as a filling reservoir during the normal pumping of the heart. The appendages typically protrude from the atria and cover an external portion of the atria. Atrial appendages differ substantially from one to another. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface with one or multiple lobes.

The atrial appendages appear to be inert while blood is being pumped through them during normal heart function. In other words, the appendages don't appear to have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation once normal sinus rhythm is restored following arrhythmia events.

Historically, appendages have sometimes been modified surgically to reduce the risk imposed by atrial fibrillation. In recent years devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This process, coupled with the growth of endothelium over the face of the device, can leave a smooth, endothelialized surface where the appendage is located. In comparison to surgical procedures, devices implanted percutaneously are a less invasive means for addressing the problems associated with the left atrial appendage.

However, due to the wide variability of the ostium size and volume of the left atrial appendage, current implantable devices conventionally include a structure that cannot meet such variability, resulting in inadequate devices for many left atrial appendage anatomies. Further, such implantable devices are substantially limited by the orientation by which they can successfully be deployed. As such, it would be advantageous to provide a percutaneous system, method and/or device that addresses, for example, the issues of implant orientation, the variability in sizes and shapes of the left atrial appendage, or all of these, in order to provide high success in left atrial appendage modification. It would also be desirable to provided a device, system and method that enable easy positioning and repositioning of the device relative to the structure being modified or occluded including the positioning (or repositioning) of an occluder portion independent of other components or features of the device.

A variety of features and advantages will be apparent to those of ordinary skill in the art upon reading the description of various embodiments set forth below.

BRIEF SUMMARY OF THE INVENTION

Embodiments of the present invention are directed to various devices, systems and methods of occluding an opening in the tissue of a body. For example, in one embodiment, a medical device delivery system is provided for occluding a left atrial appendage of a heart. The medical device delivery system includes a medical device, a delivery catheter, and an actuation assembly. The medical device includes an occluder portion and an anchor portion each independently moveable between a non-deployed position and a deployed position. The delivery catheter includes an anchor tether extending through a lumen defined through the delivery catheter such that the anchor tether is coupled to the medical device. The actuation assembly is coupled to a handle housing, the actuation assembly including an actuation member and an anchor operator. The anchor operator is moveable by actuating the actuation member, the anchor operator moveable between a proximal position and a distal position relative to the handle housing. With this arrangement, upon the occluder portion being maintained in the deployed position, movement of the anchor operator between the proximal position and the distal position moves the anchor portion between the non-deployed position and the deployed position.

In another embodiment, the actuation assembly includes a float operator. The float operator is moveable by the actuation member, the float operator moveable between a distal position and a proximal position. As such, upon the anchor portion being maintained in the deployed position, movement of the float operator from the distal position to the proximal position moves the delivery catheter proximally relative to the medical device. In another embodiment, actuation of the float operator to the proximal position exposes a distal portion of the anchor tether from a distal end of the delivery catheter.

In another embodiment, the actuation assembly includes a mode switch movable by the actuation member. The mode switch is moveable between a mode switch first position and a mode switch second position such that the mode switch first position facilitates actuation of the anchor operator by the actuation member and the mode switch second position facilitates actuation of the float operator by the actuation member. Further, in one embodiment, the mode switch first position locks-out actuation of the float operator. In another embodiment, the mode switch second position locks-out actuation of the anchor operator.

In another embodiment, the delivery catheter defines a central lumen and a secondary lumen extending longitudinally through the delivery catheter. With such lumens, the anchor tether extends through the central lumen and an occluder tether extends through the secondary lumen.

In still another embodiment, the system includes a sheath with a lumen extending longitudinally therethrough such that the medical device is moveable through the lumen of the sheath to advance the medical device to the left atrial appendage. In one embodiment, the sheath includes a sheath hub at a proximal end of the sheath. Such sheath hub is sized and configured to advance the medical device therethrough. Further, the sheath hub includes transparent material to enable viewability through the sheath hub. In another embodiment, the sheath hub includes a valve configuration having an open position and a closed position. The open position is configured to facilitate advancing the medical device through the valve configuration and the closed position is configured to prevent back-flow of blood from the sheath hub. In another embodiment, such valve configuration also can include a transparent material and a fluid port extending therefrom to allow viewability of air and to facilitate pulling the air from the fluid port.

In another embodiment, the sheath of the medical device delivery system is also configured to facilitate the deployment functions of the occluder portion. For example, the occluder portion of the medical device is distal a distal end of the delivery catheter and is moved from the non-deployed position to the deployed position by the sheath being moved proximally. In another embodiment, the occluder portion is moveable between the non-deployed position and the deployed position with movement of the sheath. In still another embodiment, the anchor portion in the non-deployed position is at least partially pulled into and proximal to a distal end of the delivery catheter; and the anchor portion in the deployed position is moved out of the distal end of the delivery catheter. In another embodiment, the anchor portion includes multiple engaging members extending therefrom such that the engaging members are sized and configured to substantially prevent proximal and distal movement of the medical device relative to the left atrial appendage.

In one embodiment, the medical device delivery system includes a release assembly. The release assembly includes a release knob, a release enable rod, an anchor release member, and an occluder release member. The release knob is configured to be rotatably movable from a release knob first position to a release knob second position, and further, the release knob is configured to be linearly moveable from the release knob second position to a release knob third position. The release enable rod is coupled to the release knob and is configured to facilitate the release knob to be moved dependent upon a position of the actuation assembly. The anchor release member is operatively coupled to the release enable rod and is coupled to wires of the anchor tether. The occluder release member is coupled to an occluder tether.

In another embodiment, movement of the release knob from the release knob first position to the release knob second position operatively couples the release enable rod to the occluder release member. In another embodiment, movement of the release knob from the release knob second position to the release knob third position simultaneously moves both the anchor release member and the occluder release member to facilitate simultaneous detachment of the anchor tether and the occluder tether from the medical device. Further, in another embodiment, the release enable rod includes a flat portion configured to prevent rotation of the release knob when the anchor operator is movable by the actuation knob.

In accordance with another embodiment of the present invention, a medical device delivery system is provided for occluding a left atrial appendage of a heart. The medical device delivery system includes a medical device, a delivery catheter and an actuation assembly. The medical device includes an occluder portion and an anchor portion such that the anchor portion is configured to be retractable with the occluder portion maintained in a deployed position. The delivery catheter includes one or more tethers extending through one or more lumens defined through the delivery catheter and the one or more tethers are coupled to the medical device. The actuation assembly is coupled to a handle housing, the actuation assembly including an actuation member and an anchor operator. The anchor operator is moveable by the actuation member between one or more proximal positions and a distal position. Further, the anchor operator is coupled to at least one of the one or more tethers. With this arrangement, upon the occluder portion being maintained in the deployed position, movement of the anchor operator between the one or more proximal positions and the distal position moves the anchor portion between a retractable position and a deployed position.

In one embodiment, the anchor portion and the occluder portion are configured to be moveable between deployed and non-deployed positions independent of each other. In another embodiment, the anchor portion in the retracted position is at least partially pulled into and proximal a distal end of the delivery catheter; and the anchor portion in the deployed position is moved out of the distal end of the delivery catheter. In still another embodiment, the anchor portion includes multiple engaging members extending therefrom such that the engaging members are sized and configured to substantially prevent proximal and distal movement of the medical device relative to the left atrial appendage.

In another embodiment, the medical device delivery system includes a sheath with a lumen extending longitudinally therethrough such that the medical device is moveable through the sheath to advance the medical device to the left atrial appendage. In another embodiment, the occluder portion is moveable between a non-deployed position and the deployed position with movement of the sheath. Further, in another embodiment, the occluder portion is distal to a distal end of the delivery catheter and is moved from a non-deployed position to the deployed position by the sheath being manually moved proximally.

In accordance with another embodiment of the present invention, a method for occluding a left atrial appendage of a heart is provided. The method includes advancing a delivery catheter and medical device through a sheath to the left atrium of a heart and to a distal portion of the sheath, the medical device having an occluder portion and an anchor portion independently moveable between a non-deployed position and a deployed position; positioning the distal portion of the sheath within the left atrial appendage of the heart with both the occluder portion and anchor portion in the non-deployed position; withdrawing the sheath relative to the medical device to move the occluder portion of the medical device from the non-deployed position to the deployed position; actuating a portion of a handle operatively coupled to the medical device to move the anchor portion between the non-deployed position and the deployed position while the occluder portion maintains the deployed position; stabilizing the medical device in the left atrial appendage with the anchor portion engaging tissue in the left atrial appendage in the deployed position; and releasing the medical device from the delivery catheter in the left atrial appendage.

In another embodiment, the positioning step includes exposing a distal end of the occluder portion from a distal tip of the sheath to expose a cushion tip without exposing any metallic portions of a frame of the medical device. In another embodiment, the actuating step includes moving an actuation element of the handle between a first position and a second position that corresponds with the non-deployed position and the deployed position of the anchor portion, respectively. Further, the actuating step may include moving the actuation element from the second position to a third position for locking-out actuation of the anchor portion of the medical device and enabling a float mode of the medical device. Furthermore, the actuating step may include moving the actuation element from the third position to a fourth position for withdrawing the delivery catheter relative to the medical device to put the medical device in a float mode.

In another embodiment, the method further includes floating the medical device by withdrawing the delivery catheter relative to the medical device to expose tethers coupled to the medical device. In another embodiment, the releasing step includes rotating a release knob and linearly moving the release knob to detach a coupling element from the medical device. Further, the stabilizing step includes atraumatically engaging tissue with engaging members that substantially minimize movement of the medical device in both a distal direction and a proximal direction. In addition, in another embodiment, subsequent to the stabilizing step, the method includes modifying a position of the occluder portion in the left atrial appendage by actuating the portion of the handle to move the anchor portion from the deployed position to the non-deployed position.

In accordance with another embodiment of the present invention, a method of occluding a left atrial appendage of a heart is provided. The method includes: providing a medical device having an occluder portion and an anchor portion, a handle having an actuating assembly, and a coupling member extending through a delivery catheter between the medical device and the actuating assembly of the handle; advancing the medical device to the left atrial appendage through a sheath; deploying the occluder portion in the left atrial appendage by withdrawing the sheath; moving an actuation element coupled to the actuation assembly between a first hard stop and a second hard stop to move the anchor portion between a retracted position and a deployed position while the occluder portion maintains a deployed position; stabilizing the medical device in the left atrial appendage with the anchor portion engaging tissue in the left atrial appendage in the deployed position; and releasing the medical device from the delivery catheter in the left atrial appendage.

In one embodiment, the releasing step includes rotating a release knob to enable detachment of the medical device, and then linearly moving the release knob to detach the medical device from the coupling member extending through the delivery catheter. The step of linearly moving the release knob may include moving a pin wire and a pull wire operatively coupled to the release knob at the handle and directly coupled to the medical device.

In another embodiment, the advancing step includes exposing a distal end of the occluder portion from a distal tip of the sheath to expose a portion of the occluder portion to provide a cushion tip without substantially exposing any metallic portions of a frame of the medical device. Further, the advancing step includes atraumatically positioning the distal tip of the sheath in the left atrial appendage with the cushion tip of the occluder portion exposed at the distal tip of the sheath.

In another embodiment, the step for deploying the occluder portion may include movably positioning the occluder portion while in a deployed position in the left atrial appendage and while the anchor portion is in the retracted position. Further, subsequent to the stabilizing step, the method may include moving the occluder portion to a different position in the left atrial appendage by actuating the handle to move the anchor portion from the deployed position to the retracted position.

These various embodiments may include other components, features or acts as will be apparent from the detailed description set forth below. Additionally, other embodiments, configurations and processes are set forth below in the detailed description of the invention.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 1A is a side view of a medical device employed with the medical device delivery system of FIG. 1, depicting the device being implanted in a left atrial appendage, according to an embodiment of the present invention;

FIGS. 6A and 6B are side views of anchor frame segments of an anchor system, according to an embodiment of the present invention;

FIG. 6C is a perspective view of an anchor system using the frame segments shown in FIGS. 6A and 6B, according to an embodiment of the present invention;

FIGS. 11A through 11C are side views of anchor frame segments of the medical device shown in FIGS. 9A and 9B, according to the present invention;

FIG. 21 is a perspective view of a medical device coupled to medical device delivery system, depicting a handle system in a first handle position, according to one embodiment of the present invention;

FIG. 21A is partial perspective view of the medical device and medical device delivery system of FIG. 21, depicting the medical device with an anchor portion deployed when the handle system is in a second handle position, according to an embodiment of the present invention;

FIG. 21B is a partial perspective view of the medical device and medical device delivery system of FIG. 21, depicting the medical device with tethers deployed when the handle system is in a third handle position, according to an embodiment of the present invention;

FIG. 21C is an enlarged cross-sectional view of the catheter system, taken along line 21C of FIG. 21, according to another embodiment of the present invention;

FIG. 22 is a proximal end view of the handle system of FIG. 21, according to an embodiment of the present invention;

FIG. 23 is a cross-sectional side view of the handle system, taken along line 23 of FIG. 22, depicting the handle system in the first handle position, according to an embodiment of the present invention;

FIG. 23A is a cross-sectional view of the handle system, taken along line 23A of FIG. 23, depicting a mode switch of the handle system, according to an embodiment of the present invention;

FIG. 24 is a cross-sectional bottom view of the handle system, taken along line 24 of FIG. 22, depicting the handle system in the first handle position, according to an embodiment of the present invention;

FIG. 24A is an enlarged section view of a float handle portion of the handle system, taken from detail "24A" of FIG. 24, according to an embodiment of the present invention;

FIG. 24B is an enlarged section view of a occluder handle portion of the handle system, taken from detail "24B" of FIG. 24, according to an embodiment of the present invention;

FIG. 24C is an enlarged section view of an anchor handle portion of the handle system, taken from detail "24C" of FIG. 24, according to an embodiment of the present invention;

FIG. 25 is a cross-sectional side view of the handle system, depicting the handle system in the second handle position, according to another embodiment of the present invention;

FIG. 25A is a cross-sectional view of the handle system, taken along section line "25A" of FIG. 25, according to an embodiment of the present invention;

FIG. 26 is a cross-sectional side view of the handle system, depicting the handle system in the third handle position, according to an embodiment of the present invention;

FIG. 26A is a cross-sectional view of the handle system, taken along section line "26A" of FIG. 26, according to an embodiment of the present invention;

FIG. 27 is a proximal end view of the handle system, depicting a release-enable switch in a released position, according to an embodiment of the present invention;

FIG. 28 is a cross-sectional side view of the handle system, taken along section line "28" of FIG. 27, depicting the handle system in the released position;

FIG. 28A is a cross-sectional view of the handle system, taken along section line "28A" of FIG. 28;

FIG. 29 is a cross-sectional bottom view of the handle system, taken along section line "29" of FIG. 27, depicting the handle system in the released position;

FIG. 36 is an enlarged cross-sectional view of a medical device being pushed through a sheath by a catheter system, according to an embodiment of the present invention;

FIG. 37 is an enlarged cross-sectional view of an occluder portion of the medical device being deployed from the sheath, according to an embodiment of the present invention;

FIG. 38 is an enlarged cross-sectional view of an anchor portion with the occluder portion of the medical device deployed from the catheter system, according to an embodiment of the present invention;

FIG. 38A is an enlarged cross-sectional view of the catheter system and sheath, taken from line 38A, according to an embodiment of the present invention;

FIG. 39 is an enlarged cross-sectional view of an interconnection between the medical device and tether wires, according to an embodiment of the present invention;

FIG. 42 is a side view of an articulating handle system, according to an embodiment of the present invention;

FIG. 42A is an enlarged cross-sectional view of the articulating handle system, taken from line 42A of FIG. 42, according to an embodiment of the present invention;

FIG. 48A is a partial perspective view of the medical device system of FIG. 48, illustrating the medical device with both the occluder portion and the anchor portion deployed, according to an embodiment of the present invention;

FIG. 48B is a partial perspective view of the medical device system of FIG. 48, illustrating the medical device in a float mode, according to an embodiment of the present invention;

FIG. 48C is a partial perspective view of the medical device system of FIG. 48, illustrating the medical device detached from the medical device system, according to an embodiment of the present invention;

FIG. 53 is a side view of the handle (upper housing removed), illustrating the handle in a first position, according to one embodiment of the present invention;

FIG. 53A is a cross-sectional view of the handle at section 53A of FIG. 53, illustrating a first mode switch position of a mode switch, according to an embodiment of the present invention;

FIG. 53B is a cross-sectional view of the handle at section 53B of FIG. 53, illustrating a first position of a latch, according to an embodiment of the present invention;

FIG. 54 is an end view of the handle depicted in FIG. 53, according to the present invention;

FIG. 54A is a cross-sectional view of the handle taken along section line 54A of FIG. 54, according to the present invention;

FIG. 54B is an enlarged partial view of the handle taken from section 54B of FIG. 54A, according to an embodiment of the present invention;

DETAILED DESCRIPTION OF THE INVENTION

Figure 1:
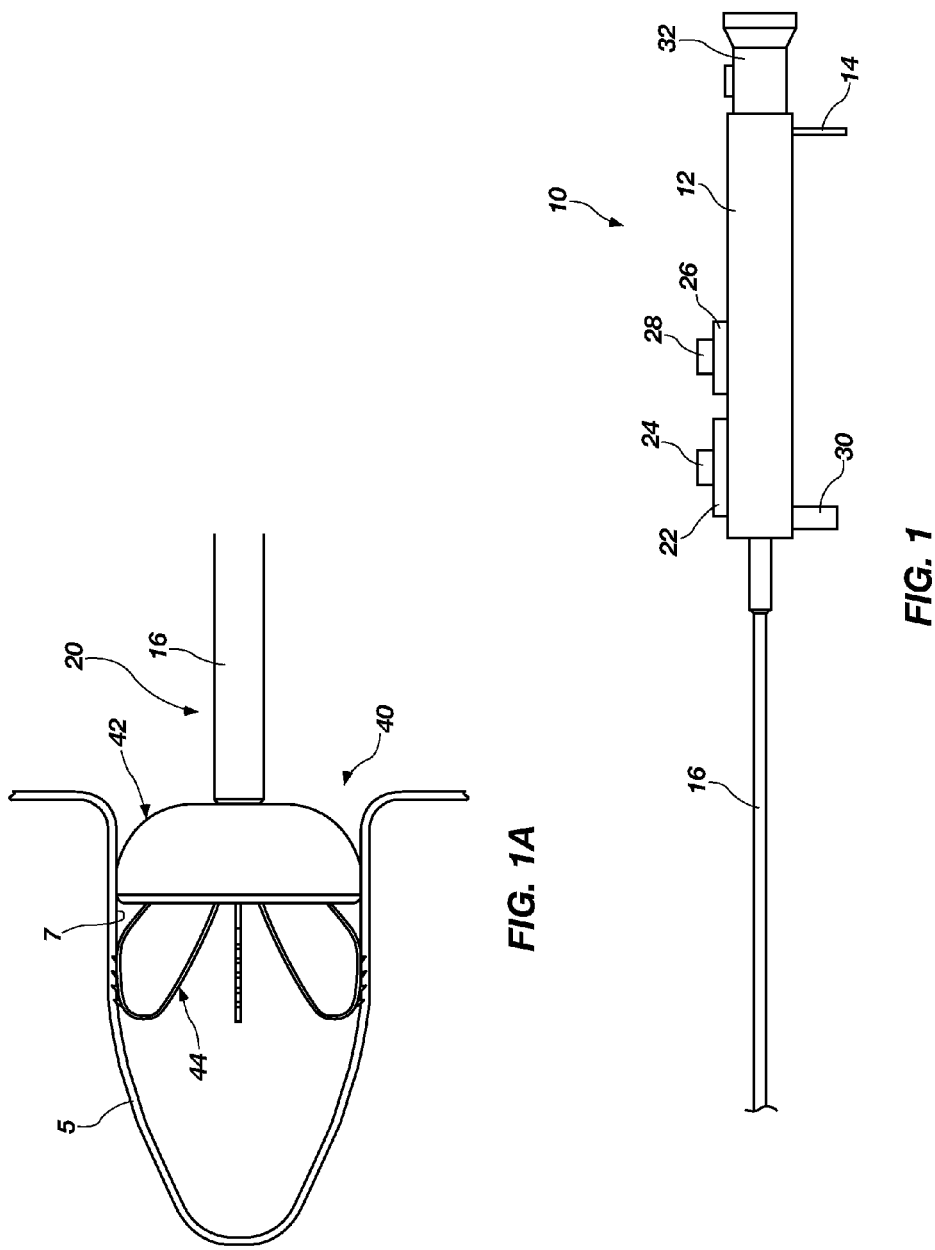
FIG. 1 is a side view of a medical device delivery system, according to an embodiment of the present invention.

Referring to FIGS. 1 and 1A, a medical device system 10 is disclosed that may be used to occlude or modify an opening or cavity 5 such as, for example, a left atrial appendage (LAA). In one embodiment, the medical device system 10 may include a handle 12 with one or more actuators and a fluid port 14. In addition, the system 10 may include a catheter 16 with a catheter lumen extending longitudinally therethrough and attached to a distal end of the handle 12. Such a catheter lumen may coincide and communicate with a handle lumen as well as communicate with the fluid port 14.

The actuators associated with the handle may be configured to actuate or move a medical device 40 disposed within a distal portion 20 of the catheter 16 to deploy the medical device 40 from or within the distal portion 20 of the catheter 16, to capture (or recapture) the medical device 40 within the distal portion 20 of the catheter, or to do both. Such a medical device 40 can be interconnected to the handle 12 via tethers coils or other structures or elements (generally referred to as tethers herein for convenience) extending through the catheter 16 (tethers not shown in FIGS. 1 and 1A). For example, the tethers can have a proximal end connected to the handle 12 and a distal end thereof connected to the medical device 40. The medical device 40 can be manipulated to be deployed and recaptured at different stages by controlling movement of the tether/coils (via the actuators) and controlling movement of the catheter 16.

The medical device 40, shown in deployed position in FIG. 1A (wherein the device is fully or at least substantially expanded), may include an occluder system 42 and an anchor system 44. As briefly noted above, the medical device 40 can be controlled to deploy in discrete stages with one stage being the deployment of the occluder system 42 and another, discrete stage being deployment of the anchor system 44. In this manner, a physician can first deploy the occluder system 42, locate a preferable position and orientation for the occluder system 42 in the LAA 5 and, once positioned and oriented satisfactorily, the physician can maintain such position while independently deploying the anchor system 44. As such, the occluder system 42 and the anchor system 44 are configured to be deployed independent of one another as discrete, affirmative acts by a physician or operator of the system 10.

As previously noted, the handle 12 may include multiple actuators including a release mechanism 32. The release mechanism 32 is configured to release the medical device 40 from the tethers once the medical device 40 is anchored in the LAA 5 as will be described in further detail below. Other actuators may include a first actuator 22, a second actuator 24, a third actuator 26, a fourth actuator 28 and a fifth actuator 30 as shown in FIG. 1. For example, the first actuator 22 and the second actuator 24 may be configured to control movement of the occluder system 42 while the third actuator 26 and the fourth actuator 28 may be configured to control movement of the anchor system 44. The fifth actuator 30 may be configured to control maneuverability of the distal portion 20 of the catheter 16 to negotiate tight corners and facilitate orientation when placing the medical device 40 in the LAA 5. It should be noted that, for example, the first actuator 22 and the second actuator 24 can be configured as, or to act as, a single actuator for the occluder system 42. Likewise, the third actuator 26 and the fourth actuator 28 can be configured as, or to act as, a single actuator for the anchor system 44.

Figure 2:
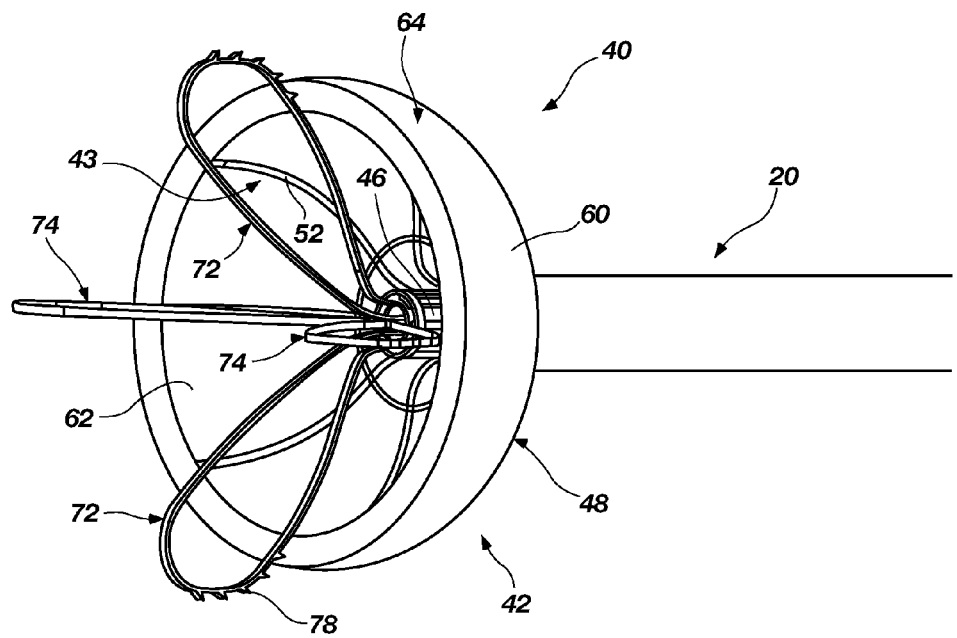
FIG. 2 is a perspective view of the medical device of FIG. 1A, depicting the medical device in a fully expanded position, according to an embodiment of the present invention.
Figure 3:
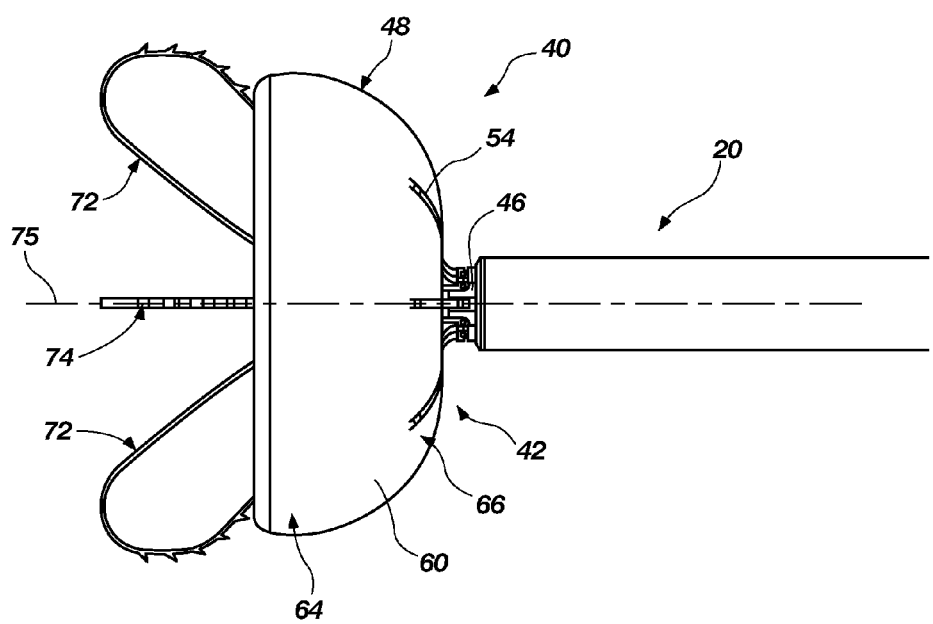
FIG. 3 is a side view of the medical device of FIG. 2.
Figure 3A:
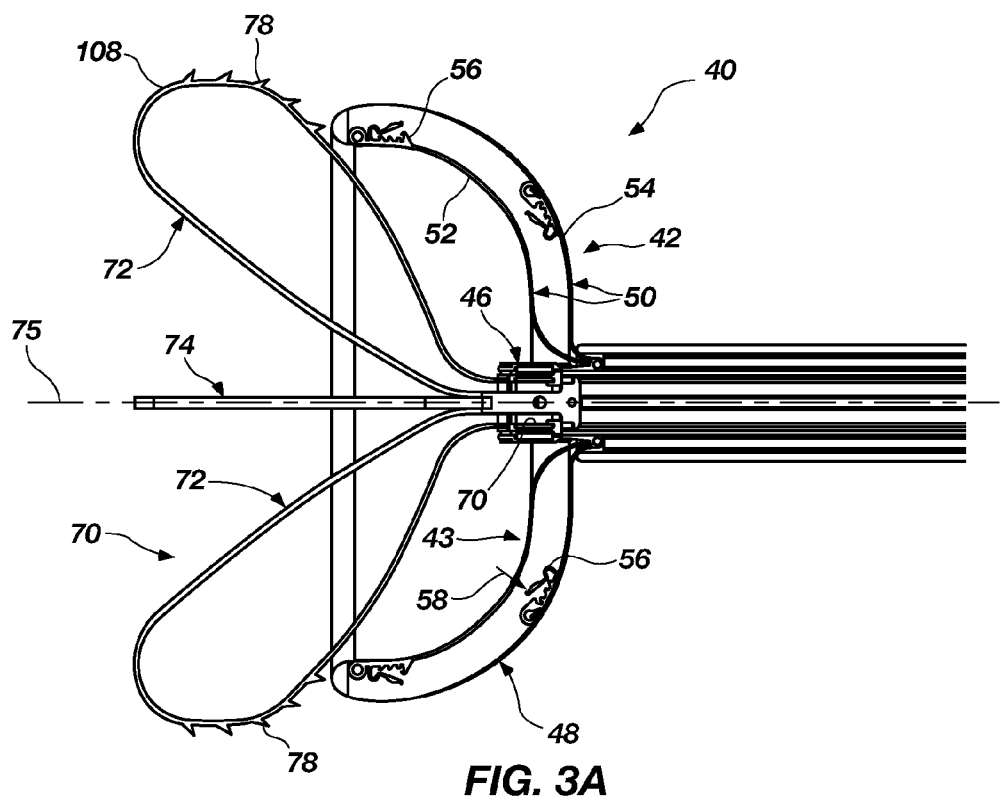
FIG. 3A is a cross-sectional view of the medical device of FIG. 3.

With reference to FIGS. 2, 3 and 3A, the occluder system 42 may include an occluder frame 43 coupled to an occluder hub system 46 and a tissue growth member 48. The occluder frame 43 includes multiple occluder frame segments 50 extending radially and distally from the occluder hub system 46 generally in a spoke-like configuration. Such an occluder frame 43 is configured to assist in both expanding the tissue growth member 48 and in collapsing the tissue growth member 48. As such, each frame segment 50 may include an expander portion 52 and a collapser portion 54, wherein the expander portion 52 can include an overall length greater than that of the collapser portion 54. For example, each expander portion 52 may extend further radially, further distally, or both, as compared to a collapser portion 54.

Further, each frame segment 50 may include a clip 56 on each of the expander portion 52 and collapser portion 54. The clips 56 may be utilized to attach the tissue growth member 48 between the expander portion 52 and the collapser portion 54. Such clips 56 are each shown in an open position (FIG. 3A), but when attaching the tissue growth member 48 to the occluder frame 43, the clips 56 are moved to a closed position, as indicated by arrow 58. In this manner, the tissue growth member 48 can be readily attached to the occluder frame 43.

The tissue growth member 48 may include a porous structure configured to induce or promote tissue in-growth, or any other suitable structure configured to promote tissue in-growth. The tissue growth member 48 can include, for example, a body or a structure exhibiting a cup-like shape having an outer surface 60 and an inner surface 62. The outer surface 60 may include a distal surface portion 64 and a proximal surface portion 66. The outer surface distal surface portion 64 of the tissue growth member 48 can be sized and configured to be in direct contact with a tissue wall 7 within the LAA 5 (see FIG. 1A). In one embodiment, the tissue growth member 48 may be configured to self expand from a confined or constricted configuration to an expanded or deployed configuration. In one embodiment, the tissue growth member 48 may include a polymeric material, such as polyurethane foam. Other materials with desired porosity can also be used, such as felt, fabric, Dacron®, Nitinol braided wire, or polymeric or Nitinol felt. In the case of foam, such foam may be a reticulated foam, typically undergoing a chemical or heating process to open the pores within the foam as known by those of ordinary skill in the art. The foam may also be a non-reticulated foam. In one embodiment, the foam may include graded density or a graded porosity, as desired, and manipulated to expand in a desired shape when the frame member is moved to the expanded configuration.

In another embodiment, the tissue growth member 48 may include polyurethane foam with a skin structure on the inner surface 62, on the outer surface 60, or on both surfaces. For example, a skin structure may be formed on the inner surface 62 and be configured to inhibit blood from flowing through the tissue growth member 48, while the outer surface 60 of the tissue growth member may be configured to receive blood cells within its pores and induce tissue in-growth. In one embodiment, such a skin structure can include a layer of material, such as tantalum, sputtered to a surface of the tissue growth member 48. In another embodiment, the skin structure can include a polyurethane foam skin. Another example includes attaching expanded polytetrafluoroethylene (ePTFE) to the outer surface 60 or inner surface 62 of the tissue growth member 48, the ePTFE having minimal porosity to substantially inhibit blood flow while still allowing endothealization thereto.

In one embodiment, the anchor system 44 may include a plurality of anchor components and an anchor hub system 70. The anchor hub system 70 may be configured to be positioned and disposed within or adjacent to the occluder hub system 46. The plurality of anchor components can include, for example, a first anchor component 72 and a second anchor component 74. Each of the first anchor component 72 and the second anchor component 74 may include a pedal or loop configuration (shown in FIGS. 2, 3, 3A, 6A and 6B in an expanded configuration), with, for example, two loop configurations for each of the first and second anchor components 72 and 74, that are interconnected together via the anchor hub system 70 (discussed in more detail below). Each loop may be substantially oriented orthogonally with respect to an adjacent loop (i.e., in the embodiment shown in FIGS. 2 and 3, each loop of anchor component 72 being orthogonal to adjacent loops of anchor component 74). It is noted that, as used herein, the term "loop" does not require that a closed curve be formed of the component, but rather that a substantially closed curved or an open curve having a portion of the curve return on itself may also be considered as a "loop."

While in the expanded configuration, each loop may extend distally of the occluder system 42 and radially outward to a larger configuration than the anchor hub system 70. In other words, at least a portion of the anchor components 72 and 74 extend distally beyond the distal-most portion of the occluder system 42 and radially beyond the radial-most portion of the occluder system as taken from a longitudinal axis 75 extending through the hub system 70. Each loop of an anchor component 72 and 74 may also include engagement members or traction nubs 78 on an outer periphery of a loop configuration, the traction nubs 78 being sized and configured to engage and grab a tissue wall 7 within the LAA 5 (see FIG. 1A). In one embodiment, the traction nubs 78 may be configured to aggressively engage the tissue wall 7 without piercing or penetrating the tissue. As such, such traction nubs may be configured as atraumatic structures.

Each of the loop configurations of the first anchor component 72, while in an expanded configuration, are substantially co-planar with each other and in a substantially flat configuration. Likewise, each of the loop configurations of the second anchor component 74, while in an expanded configuration, are substantially co-planar with each other and in a substantially flat configuration. In one embodiment, the first anchor component 72 may be attached to the second anchor component 74 such that the loop configuration between the first and second anchor components 72 and 74 are oriented substantially orthogonal with respect to each other. In other words, the plane in which the first anchor component 72 is positioned or oriented is substantially orthogonal with respect to the plane of the second anchor component 74. In other embodiments, there may be more than two anchor components, in which case such anchor components may or may not be oriented in a substantially orthogonal manner relative to each other.

Figure 3B:
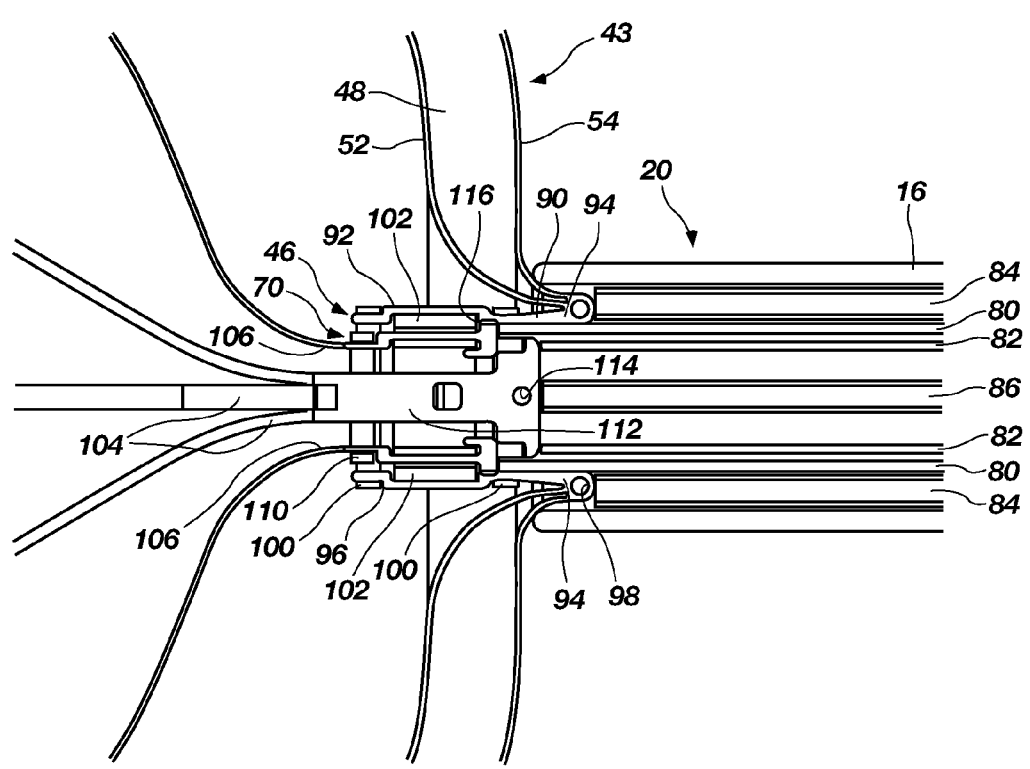
FIG. 3B is an enlarged view of a hub system of FIG. 3A.

With reference to FIGS. 3A and 3B, the medical device system 10 includes multiple catheters or tubular members and tether systems to manipulate movement and deployment of the occluder system 42 as well as the anchor system 44. For example, the primary catheter 16 or outer catheter may include a first tubular member 80 and a second tubular member 82 positioned therein and extending substantially the longitudinal length thereof. Such tubular members can be catheter components, coiled components or any other suitable tubular member known in the art. Further, as previously noted, the medical device system 10 may include a first tether system 84 and a second tether system 86, the first tether system 84 configured to be tethered to the occluder system 42 and the second tether system 86 configured to be tethered to the anchor system 44. The tether systems 84 and 86 may include, for example, one or more wires extending through a coiled component. In one embodiment, heat-shrink polymeric material may also be formed over the coiled component.

As previously noted, the occluder system 42 may include, multiple occluder frame segments 50, an occluder hub system 46 and a tissue growth member 48. Each occluder frame segment 50 may include a base portion 90, an expander portion 52 and a collapser portion 54. The base portion 90 may include a distal base portion 92 and a proximal base portion 94. The proximal base portion 94 may include an attachment point such as, for example, a tether eyelet 98. Further, the expander portion 52 and the collapser portion 54 may extend radially from the proximal base portion 94 of each occluder frame segment 50 and may also extend distally from the proximal base portion 94 of each occluder frame segment.

The distal base portion 92 may include notches 96 sized and configured to receive rings to form the occluder hub system 46. In one embodiment, the rings may include, for example, two outer rings 100 and one or more intermediate inner rings 102, each positioned and interconnected with each base portion of the occluder frame segments 50 to form the occluder hub system 46. With this arrangement, the occluder system 42 may be deployed from the primary catheter 16 with the first tether system 84 having a portion thereof attached to the tether eyelet 98 at the proximal base portion 94. Although not shown in FIG. 3B, deployment of the occluder system 42 can be effected while the anchor system 44 is still retracted within the first tubular member 80 so that only the occluder system 42 is deployed. The occluder system 42 may also be retracted back into the distal portion 20 of the primary catheter 16 if desired, for example, to enable repositioning of the occluder system 42 within the LAA 5. In this manner, a physician can deploy the occluder system 42 at a desired location and orientation within the LAA 5 while also maintaining access to the occluder system 42 via the first tethering system 84.

The anchor system 44, as previously indicated, may include an anchor hub system 70, a first anchor segment 72 and a second anchor segment 74, with each anchor segment 72 and 74 including two loop configurations when in an expanded configuration. Each of the loops may include a first end portion 104 and a second end portion 106 with an intermediate portion 108 therebetween. The intermediate portion 108 includes the engagement nubs or traction nubs 78, such as previously set forth. When the anchor system 44 is in a deployed state, the first end portion 104 of the loop can extend from a base portion 112 and the second end portion 106 can interlock with the anchor hub system 70 including multiple rings 110 disposed within or adjacent to the occluder hub system 46. The first end portion 104 of each loop of the first anchor segment 72 can each extend from the base portion 112 thereof. Likewise, the first end portion 104 of each loop of the second anchor segment 74 can each extend from the base portion 112 of the second anchor segment 74.

The base portion 112 of each of the first and second anchor segments 72 and 74 can be interlocked or coupled together and configured to be positioned within or adjacent to the rings 110 (when in the deployed configuration) and moveable to a proximal position within the first tubular member 80 toward a retracted or un-deployed position. Such base portion 112 is configured to be tethered to the second tethering system 86 via an eyelet 114 or other structure in the base portion 112. Further, the base portion 112 can be moved within the first tubular member 80 between a retracted position and a deployed position. In the retracted position, the base portion 112 is positioned proximally in the first tubular member 80, in which a substantial portion of each of the first and second anchor segments 72 and 74 are rolled within the first tubular member 80 such that the "loop" portion of the anchor segments 72 and 74 exhibit a relatively tighter curve or smaller radius. Further, in the retracted position, the anchor hub system 70 can also be moved proximal the occluder hub system 46 because both systems can act independent of each other. When moving the anchor system 44 to the deployed position, the anchor hub system 70 may be moved distally to engage or abut a portion of the occluder hub system 46 via a stopper 116 defined on the second end portion 106 of the anchor segments 72 and 74, after which, the base portion 112 of anchor segments 72 and 74 can be moved distally with respect to the first tubular member 80 or primary catheter, from which the anchoring system 44 rolls out of the primary catheter 16 to expand the loops into the deployed position. In another embodiment, the second end portion of anchor segments 72 and 74 may remain adjacent to the occluder hub system in both the deployed and retracted states while the base portion is displaced relative to the occluder hub system 46 for deployment of the anchor system 44. In either configuration, the physician maintains access and control of the anchoring system 44 via the second tethering system 86 and can, therefore, determine if the medical device 40 is properly placed or, if not, can readily retract the anchor system 44 by moving the base portion 112 of the anchor segments proximally to roll a substantial portion of the anchor segments 72 and 74 within the first tubular member 80.

Figure 4A:
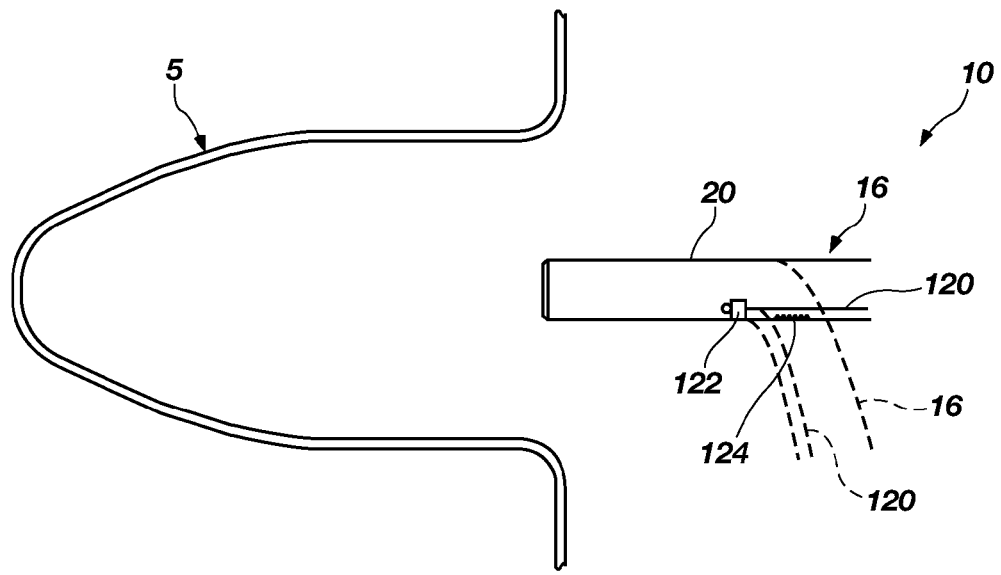
FIGS. 4A through 4D are side views of the medical device of FIGS. 2 and 3, depicting various stages of deploying the medical device from the medical device delivery system in a left atrial appendage of the heart, according to an embodiment of the present invention.

With respect to FIGS. 4A through 4D, the medical device 40 is shown while being deployed in an LAA 5, primarily employing a two stage deployment method, in which an occluder system 42 is deployed and then an anchoring system 44 is deployed. With reference to FIG. 4A, the distal portion 20 of the catheter 16 of the medical device system 10 is advanced to the LAA 5. As shown by dashed lines, the distal portion 20 may be manipulated and maneuvered to make sharp turns as needed in order to access the LAA 5 or an area adjacent thereto. This can be employed, for example, by actuation of the fifth actuator 30 (FIG. 1) which may be configured to properly orient and obtain favorable initial position of the distal portion 20 of the catheter 16. For example, the fifth actuator 30 may be coupled to a line 120 that is, in turn, coupled to a fixed point or block 122 that is distal of a region 124 in which a bend would be desired within the distal portion 20 of the catheter 16. In one embodiment, the material at the bend region 124 of the primary catheter 16 can be softened or thinned so that when the line 120 is pulled via the fifth actuator 30, the primary catheter 16 will bend at the region of softened or thinned material. This can also be accomplished via a pull line and/or a push line, the push line having, for example, a coil employed therewith.

Figure 4B:
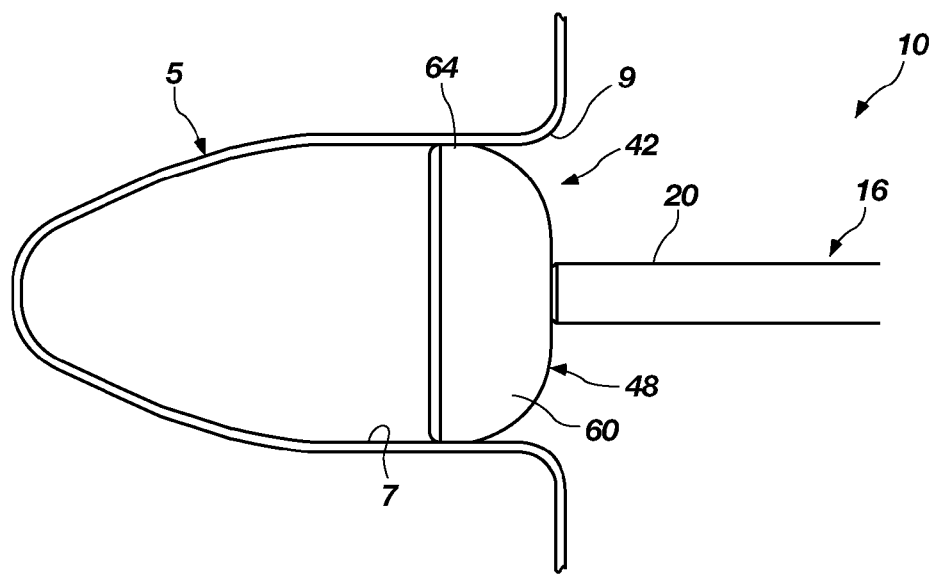

With respect to FIG. 4B, the occluder system 42 is shown being deployed from the distal portion 20 of the medical device delivery system 10 (though the anchor system 44 is not yet deployed). Before deploying the occluder system 42, the physician may initially manipulate the distal portion 20 of the delivery system 10 distal of the ostium 9 of the LAA 5. Once in a favorable position, the physician can deploy the occluder system 42 and then move the occluder system proximally within the LAA 5 until a desired orientation and position of the occluder system 42 is obtained in the LAA 5. With reference to FIG. 3B, the occluder system 42 can be deployed, for example, by maintaining position of the occluder system 42 via the first tethering system 84 and retracting the primary catheter 16 relative to the occluder system 42. The occluder frame, which may be formed of, for example, a shape memory material as discussed in further detail below, can then self expand as it is unsheathed from the primary catheter 16. In this manner, the distal surface portion 64 of the outer surface 60 of the tissue growth member 48 is radially expanded to come in contact with the tissue wall 7 of the LAA 5.

Figure 4C:
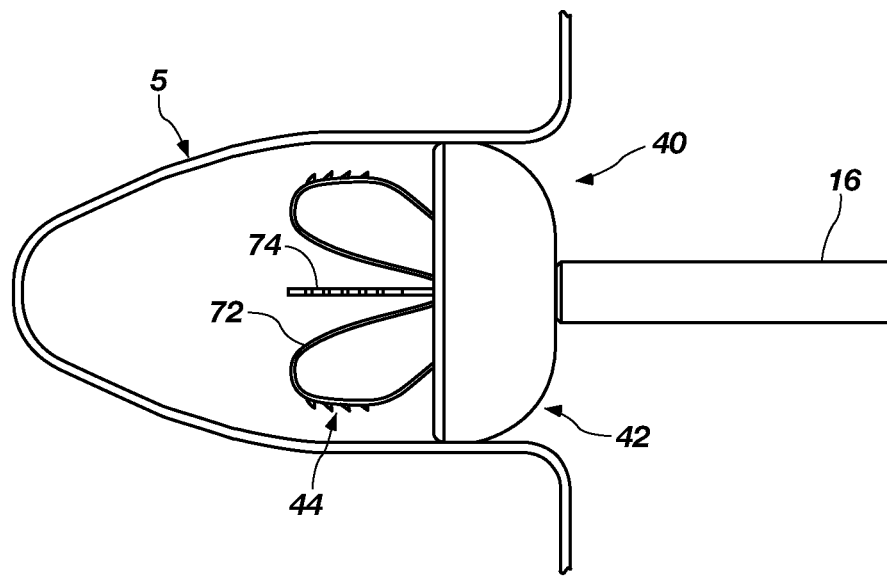

With respect to FIG. 4C, once the physician obtains a desired position in the LAA 5, (which may be at a position and orientation other than that shown), the physician can then begin to deploy the anchor system 44 while holding the position of the occluder system 42 in the LAA 5. With the occluder system 42 maintaining the selected position in the LAA 5, the anchor system 44 can begin to be deployed by moving the anchor hub system 70 relative to the occluder hub system 46 and pushing the base portion 112 of the anchor system 44 distally via the second tethering system 86 to, thereby, roll the anchor segments 72 and 74 out of the primary catheter 16 or first tubular member 80 into the expanded loop configurations (see FIG. 3B).

Figure 4D:
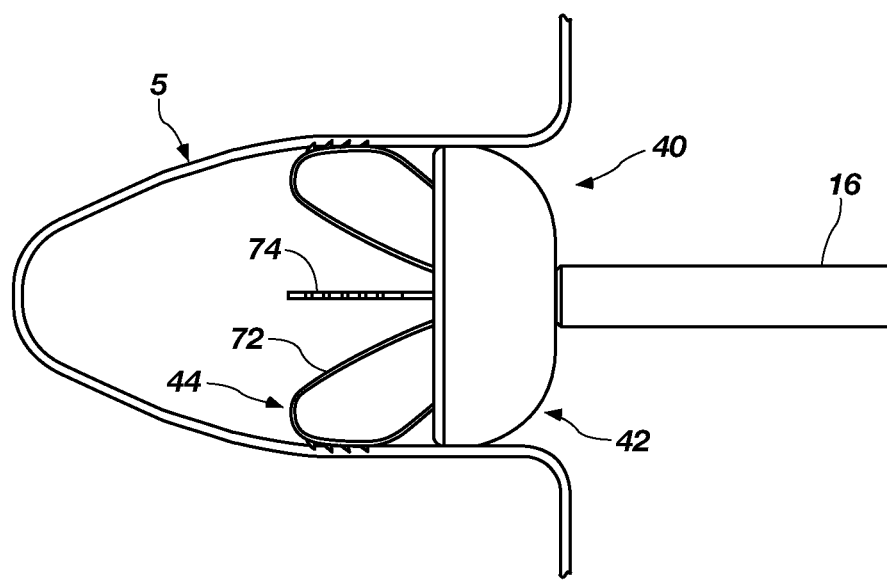

Once the base portions 112 of the first and second anchor segments 72 and 74 are moved to a fully distal position, i.e., adjacent the anchor hub system 70, the anchor system 44 is then fully deployed, as depicted in FIGS. 3, 3A and 4D. In this position, the primary catheter 16 and first and second tubular members 80 and 82 can be retracted and only the first and second tethering systems 84 and 86 maintain connection with or access to the respective occluder system 42 and anchor system 44. If the physician is satisfied with the orientation and position of the medical device 40 in the LAA, the medical device 40 can then be released via the release mechanism 32 (FIG. 1). However, if the physician is not satisfied, the anchoring system 44 and the occluder system 42 can then be respectively re-sheathed in the distal portion 20 of the catheter 16. The physician can then undergo another attempt using the same medical device 40 and delivery system 10 again following the process described above. It is noted that the physician may use various imaging techniques to monitor the placement and deployment of the medical device 40. For example, a physician may advance contrast in the LAA to view the position of the medical device 40 via imaging techniques known in the art.

Figure 5A:
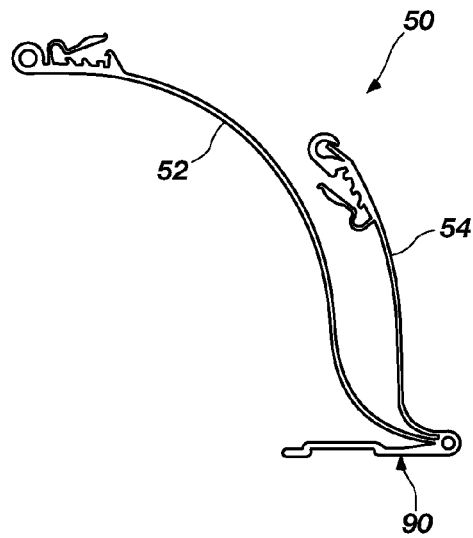
FIG. 5A is a side view of an occluder frame segment of the medical device, according to an embodiment of the present invention.
Figure 5B:
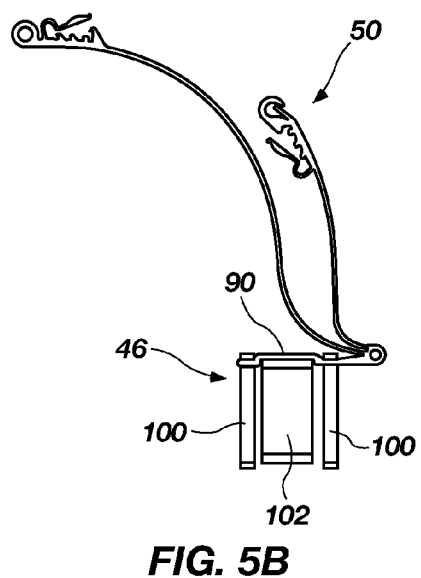
FIG. 5B is a side view of the occluder frame segment of FIG. 5A coupled to a ring system, according to another embodiment of the present invention.
Figure 5C:
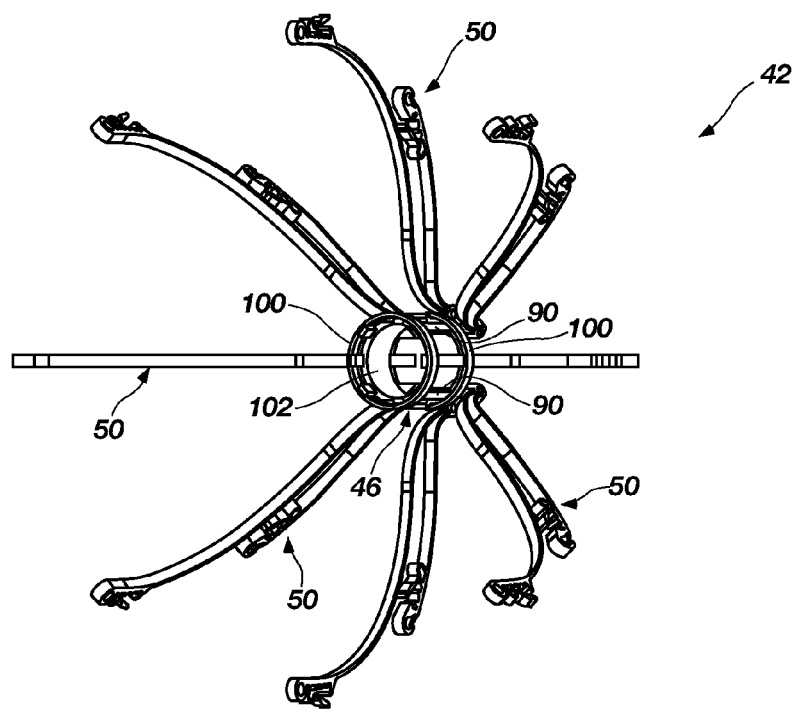
FIG. 5C is a perspective view of an occluder frame, according to an embodiment of the present invention.

Referring now to FIGS. 5A through 5C, various components of the occluder system 42 are shown in FIGS. 5A and 5B, while the assembly of the occluder system 42 is shown in FIG. 5C according to an embodiment of the present invention. With respect to FIG. 5A, one occluder frame segment 50 is shown including each of the base portion 90, expander portion 52 and collapser portion 54. The occluder system 42 may include, for example, four frame segments, but may include more or fewer than four in other embodiments. In one particular embodiment, eight frame segments 50 may be employed. Each frame segment 50 may be, for example, laser cut from a sheet of Nitinol with the shape and design of the preferred fully expanded position as shown, for example, in FIG. 5A. In such an embodiment, each frame segment may be formed as a substantially planar member or, stated otherwise, exhibit a substantially planar configuration. As depicted in FIGS. 5B and 5C, each occluder frame segment 50 is assembled in a ring or hub assembly 46 which may include, for example, two outer rings 100 and one inner ring 102. The rings 100 and 102 may include notches (not shown in FIG. 5B or 5C) to orient and position each of the occluder frame segments 50 at desired radial positions along an inner and/or outer periphery of the rings.

For simplification purposes, only one frame segment is shown in cross-section with the ring assembly in FIG. 5B, however, as shown in FIG. 5C, the occluder system 42 can include multiple frame segments 50 positioned radially about the rings 100 and 102 in a desired pattern or geometric configuration. The combination of the multiple base portions 90 of each occluder frame segment 50 and the rings 100 and 102 form the occluder hub system 46. Further, the occluder hub system 46 is sized and configured to facilitate at least a portion of the anchor system (not shown in FIGS. 5A-5C) through an opening (e.g., through the rings) of the occluder hub system 46. With this arrangement, each component of the occluder system 42 can be laser cut from sheet of shape memory alloy (e.g., a nickel-titanium alloy, also know as Nitinol) if desired, including the rings 100 and 102. In other embodiments, the various components of the hub system can be formed employing polymers or other metallic materials and machined using typical techniques and methods. Additionally, not all of the components need be formed from the same material or using the same manufacturing process. For example, in one embodiment, the frame segments 50 may be formed by laser cutting them from Nitinol sheets as noted above, while the rings 100 and 102 are formed of a polymer material through a molding process.

Turning now to FIGS. 6A through 6C, the components of the anchor frame segments of the anchoring system 44 are shown. The first anchor segment 72 (FIG. 6A) and the second anchor segment 74 (FIG. 6B) each include a first end portion 104 and a second end portion 106, the first end portion 104 extending from the base portion 112 with an intermediate portion 108 between the first end portion 104 and the second end portion 106. When in the expanded position (as shown in FIGS. 6A and 6B), each anchor segment 72 and 74 can define one or more loop configurations. For example, the embodiment shown in FIGS. 6A and 6B each include two loops.

The base portion 112 of the first anchor segment 72 includes an opening or hole 118 extending therethrough. The hole 118 is sized and configured to receive inner edge portions 120 of the second anchor segment 74. With this arrangement, the first anchor segment 72 is oriented and positioned in an orthogonal orientation with respect to the second anchor segment 74 (see FIG. 6C) such that inner edge portions 120 of the second anchor segment 74 engage the hole 118 of the first anchor segment 72.

It is also noted that the first end portion 104 tapers in thickness along its length extending toward the second end portion 106, or at least partially along the curvilinear length thereof. Such taper provides the resilience and expansion characteristics to maintain an anchored position (i.e., the deployed position of the anchor segments 72 and 74). Further, the second end portion 106 includes a notched configuration sized and configured to receive the rings 110 to form the anchor hub system 70. As previously set forth, the anchor hub system 70 is sized and configured to be positioned within or adjacent to the occluder hub system (not shown in FIGS. 6A-6C) when fully deployed. The base portion 112 of the second anchor segment 74 is further sized and configured to receive a ring member 122 around its proximal end. As with the occluder system 40, the anchor segments 72 and 74 and the rings 110 may be laser cut from a sheet of Nitinol material in the shape of the intended fully expanded configuration. In such an embodiment, each frame segment 72 and 74 may be formed as a substantially planar member or, stated otherwise, exhibit a substantially planar configuration. In this manner, the anchor system 44 can be made and assembled. Of course, the components of the anchor system 44 may be formed of other materials, using other manufacturing processes, as has been discussed previously with respect to the occluder system 40.

Referring now to FIGS. 7A, 7B, 7C, 8 and 8A, another embodiment of a medical device used for occluding an opening, such as an LAA, is shown. This embodiment is similar to the previously described embodiment, except in this embodiment, anchor segments are extensions of a base portion of occluder frame segments. In other words, anchor frame segments and occluder frame segments are integral with one another, although independent deployment and retraction of the occluder system and the anchor system is retained.

Figures 7A, 7B:
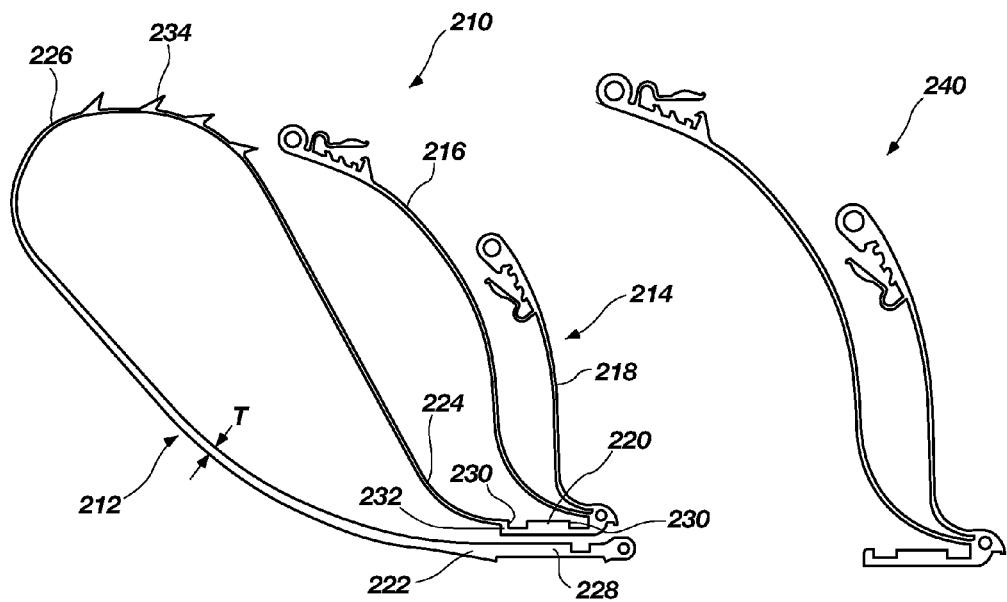
FIGS. 7A and 7B are side views of anchor frame segments and occluder frame segments, respectively, according to another embodiment of the present invention.

With initial reference to FIG. 7A, a frame segment 210 is shown that includes both an anchor segment 212 and occluder segment 214 that are integral with one another. The anchor segment 212 and the occluder segment 214 are unitary or monolithic and, for example, may be laser cut as a single frame segment from a sheet of desired material such as, for example, a Nitinol material. The anchor segment 212 includes a first end portion 222, a second end portion 224 and an intermediate portion 226 therebetween. The first end portion 222 extends from an anchor base 228 and tapers in thickness as it extends toward the second end portion 224 at least partially along a curvilinear length thereof. The intermediate portion 226 may include engagement or traction nubs 234 configured to engage (but not necessarily pierce) the tissue wall of an LAA, when in an expanded, deployed configuration. The second end portion 224 extends from a distal end 232 of a base portion 220 of the occluder segment 214.

An expander portion 216 and a collapser portion 218 both extend distally and radially outward from a proximal end 236 of the base portion 220 of the occluder segment 214. The expander portion 216 may extend further, both distally and radially, than its associated collapser portion 218. As in the previous embodiment, the expander portion 216 and the collapser portion 218 are configured to receive a tissue growth member (not shown in FIG. 7A-7C, 8 or 8A) therebetween. Further, the base portion 220 includes notches 230 sized and configured to receive rings to couple the multiple frame components, as described hereafter.

Figures 7C, 8:
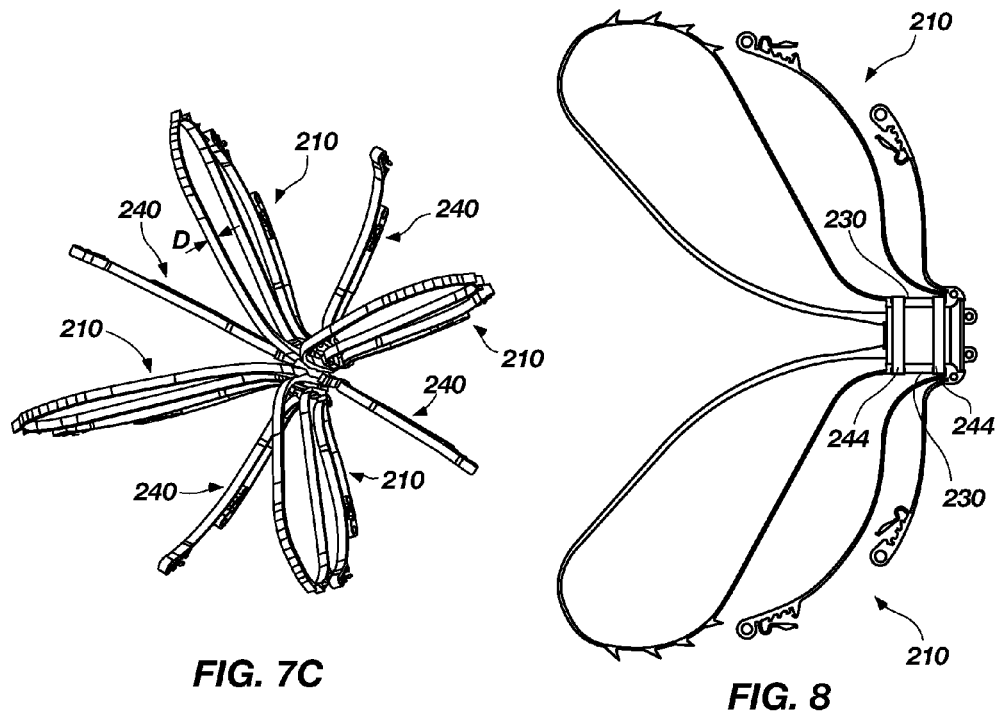
FIG. 7C is a perspective view of a frame of a medical device, depicting multiple anchor frame segments and occluder frame segments shown in FIGS. 7A and 7B, respectively, according to an embodiment of the present invention.
FIG. 8 is a cross-sectional view of the medical device of FIG. 7C.

With respect to FIG. 7B, a discrete occluder frame segment 240 is shown. This discrete occluder frame segment 240 may be configured generally similar to the occluder segment 214 of FIG. 7A (as well as the occluder frame segments 50 of the previous embodiment), except this discrete occluder frame segment 240 does not include the anchor frame segment 212 extending from the base portion 220 thereof as with the frame segment 210 shown in FIG. 7A. As depicted in FIG. 7C, the frame of the medical device includes multiple frame segments 210 (FIG. 7A) and multiple discrete occluder segments 240 (FIG. 7B) radially oriented and positioned in an alternating fashion with, for example, four frame segments 210 and four discrete occluder frame segments 240.

As previously set forth, the frame segments 210 include both an occluder segment 214 and an anchor frame segment 212. As such, in the embodiment shown in FIGS. 7C and 8, there is a total of eight occluder frame segments (four of them being the discrete occluder segments 240). However, the medical device may include fewer or more occluder frame segments. As depicted in the cross-sectional view of the frame of the medical device shown in FIG. 8, such frame segments 210 and discrete occluder frame segments 240 (not shown in FIG. 8) can be coupled together via rings 244 positioned within notches 230 of the base portion 220 of the occluder segments 214 to form an occluder hub. Likewise the base portions 222 of the frame segment 212 may be coupled together via one or more rings 272 (see FIG. 8A) to form an anchor hub.

Figure 8A:
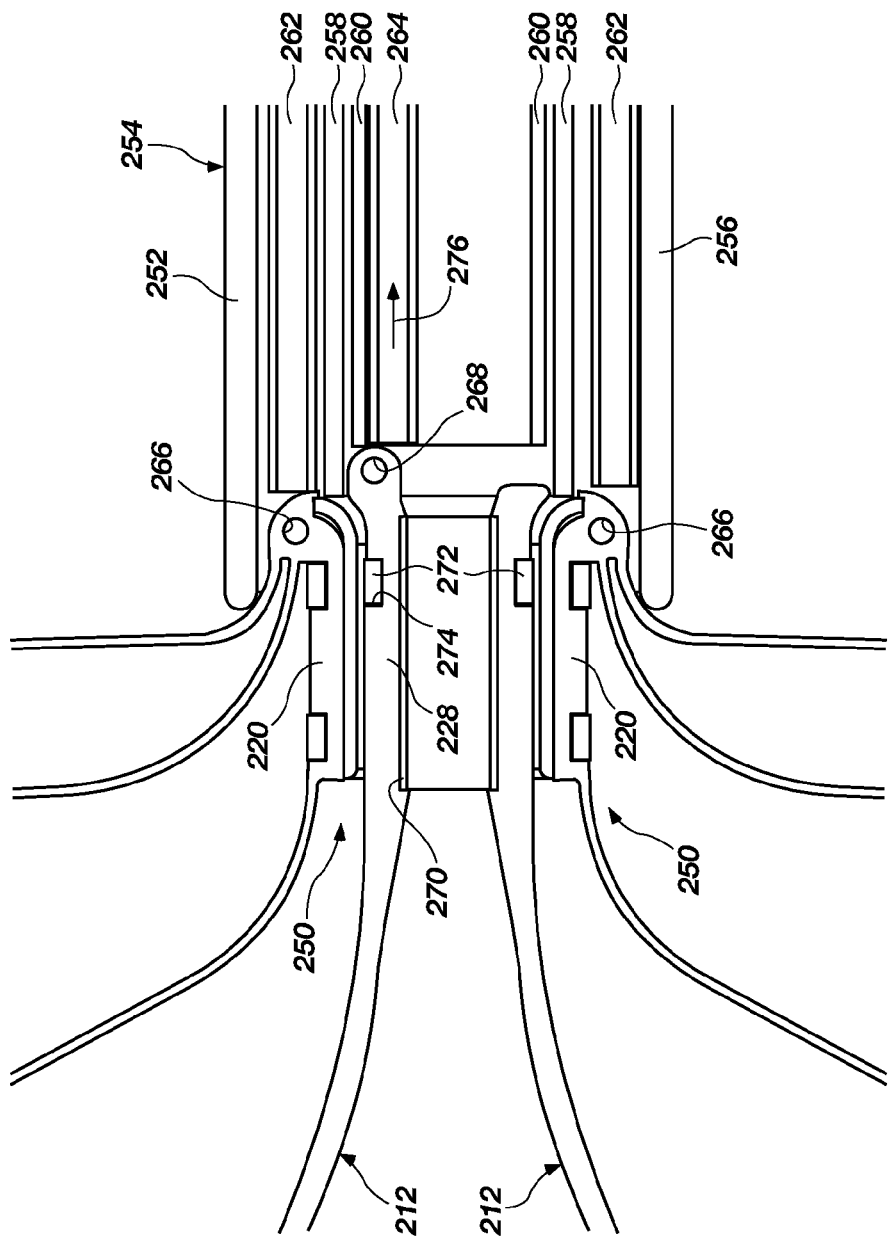
FIG. 8A is an enlarged cross-sectional view of the hub system of the medical device of FIG. 8 also depicting a distal portion of the delivery system, according to an embodiment of the present invention.

With respect to FIG. 8A, an enlarged view of a hub system 250 and a distal portion 252 of the delivery system 254 is shown. The delivery system 254 may be similar to the previously described embodiment and include a primary catheter 256, a first tubular member 258 and a second tubular member 260 and a first tethering system 262 and a second tethering system 264. The first tethering system 262 is configured to connect to the occluder system at a first eyelet 266 of the base portion 220. The second tethering system 264 is configured to connect to the anchor base 228 at a second eyelet 268 defined therein. Further, the anchor base 228 can be interconnected with a hub member 270. The hub member 270 may be configured to enable advancement of a wire, such as a guide wire, therethrough (not shown).

The hub system 250 may also include a ring member 272 configured to be received in a notch 274 defined in the anchor base 228 of each anchor segment 212. Similar to the previous embodiment, the anchor system—or at least significant portions thereof—can be retracted within the first tubular member 258 by pulling the anchor base 228 proximally via the second tethering system 264, as indicated by arrow 276. The anchor system can also be deployed from the delivery system 254 by moving the anchor base 228 distally from a proximal position to, thereby, roll the anchor segments 212 from the delivery system 254 forming expanded loops, similar to the previous embodiment. It should also be noted that the medical device of this embodiment may be deployed in two ordered or consecutive stages, similar to that which was described with respect to the previous embodiment. In other words, the occluder system may deployed and placed in desired position and orientation within the LAA independent of the anchor system. The anchor system may be deployed subsequent to the occluder system in order to secure the occluder system in its desired position.

Figure 9A:
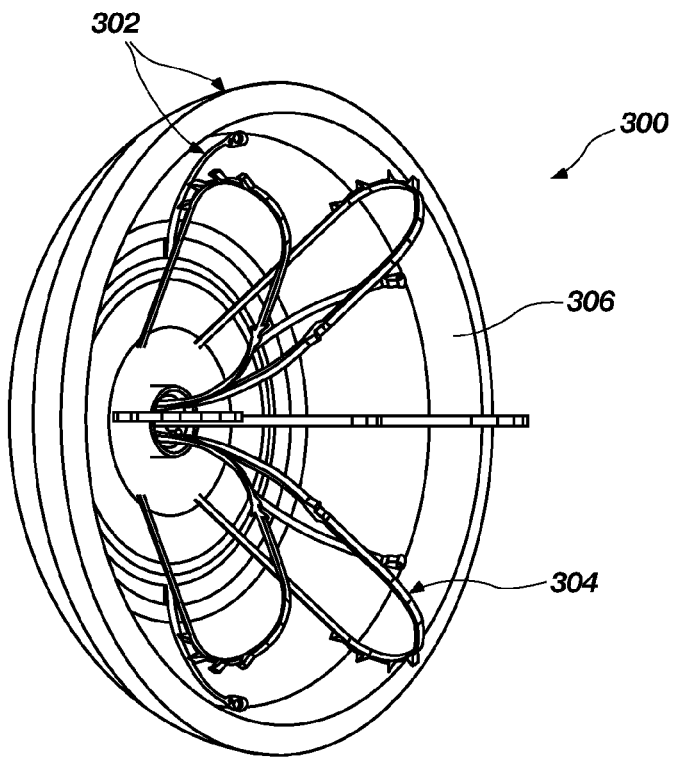
FIGS. 9A and 9B are distal and proximal perspective views of a medical device, according to another embodiment of the present invention.
Figure 9B:
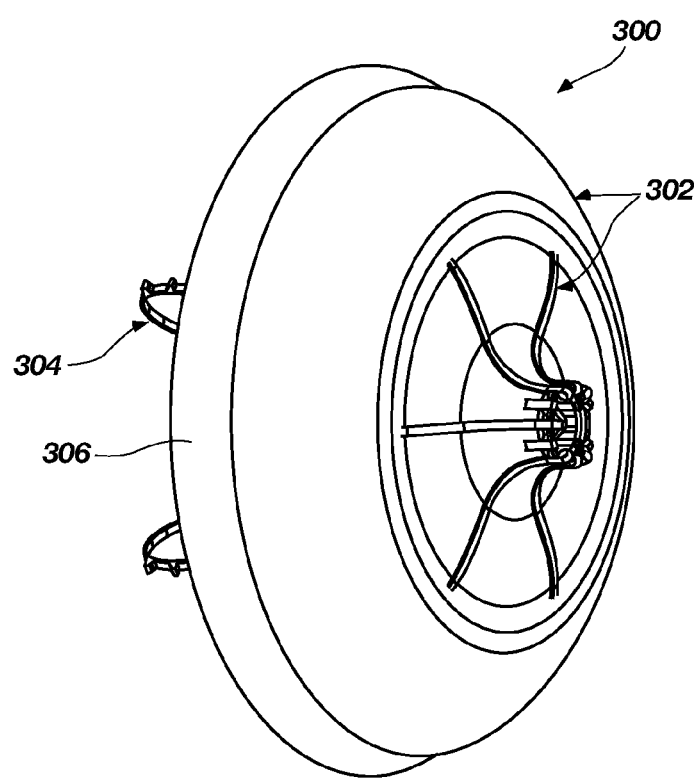

FIGS. 9A and 9B show distal and proximal perspective views of another embodiment of a medical device 300 according to the present invention. Similar to the previously described embodiments, in this embodiment, the medical device 300 includes an occluder system 302 with a tissue growth member 306 and an anchor system 304. The occluder system 302 and the anchor system 304 are separately deployable from an associated medical device delivery system, such as that described in FIG. 1 and FIGS. 4A through 4D. However, in this embodiment, the occluder system 302 and the anchor system 304 may include various additional features, as described in detail hereafter. Further, in this embodiment, the occluder system 302 is shown as including six occluder frame segments 310 (as opposed to, for example, four or eight that have been described with respect to other embodiments or, in another embodiment, even up to twelve, or, in the case of employing a wire weave, the number of frame segments could be much greater) and the anchor system 304 is shown as including three anchor frame segments 350 (each anchor frame segment having two roll-out or loop portions). Again, the number of anchor frame segments and occluder frame segments is merely another example and other numbers of frame segments are contemplated as being used with the various medical devices described herein. The anchor frame segments 350 and the occluder frame segments 310 may be positioned and oriented to alternate relative to each other. Furthermore, in this embodiment, the occluder frame segments 310 do not include the before described front and rear collapser and expander portions, but rather, each occluder frame segment may include a single frame member to which the tissue growth member 306 attaches and which facilitates both collapsing and expanding of the tissue growth member 306.

Figure 10A:
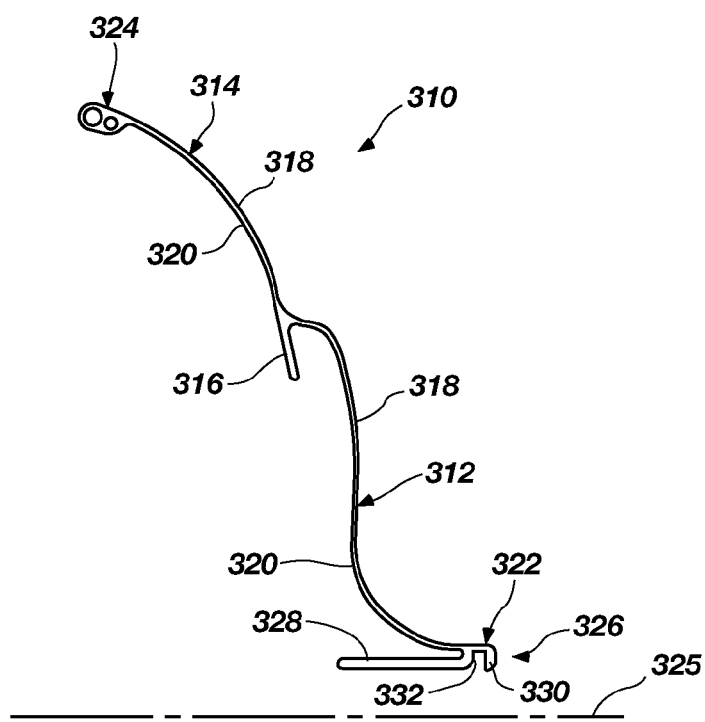
FIG. 10A is a side view of an occluder frame segment of the medical device shown in FIGS. 9A and 9B, according to the present invention.

With respect to FIG. 10A, for purposes of clarity, a side view of a single occluder frame segment 310 is shown. As noted above, the occluder system 302 (FIG. 9B) may include a plurality of occluder frame segments 310, such as six occluder frame segments that form, at least in part, the occluder system. The occluder frame segment 310 of this embodiment may include a collapser portion 312, an expander portion 314, and an intermediate extension 316. Further, the occluder frame segment 310 may include an outer surface 318 and an inner surface 320. The collapser portion 312 extends radially outward, relative to axis 325, from a proximal end portion 322 of the occluder frame segment 310 to the expander portion 314. The expander portion 314 likewise extends radially outward relative to the axis 325 from an end of the collapser portion 312 to a distal end 324 of the occluder frame segment 310. The intermediate extension 316 may extend radially inward from a location that is generally at, or adjacent to, a proximal end of the expander portion 314 and may extend in a spaced relationship with an adjacent portion of the collapser portion 312 such that the inner surface 320 of the adjacent portion of the collapser portion 312 generally faces the intermediate extension 316. Further, the occluder frame segment 310 also may include an occluder base portion 326. The occluder base portion 326 may include an occluder leg extension 328 and a protrusion 330 defining a notch 332 configured to interlock with a hub system as will be described in further detail hereafter.

Figure 10B:
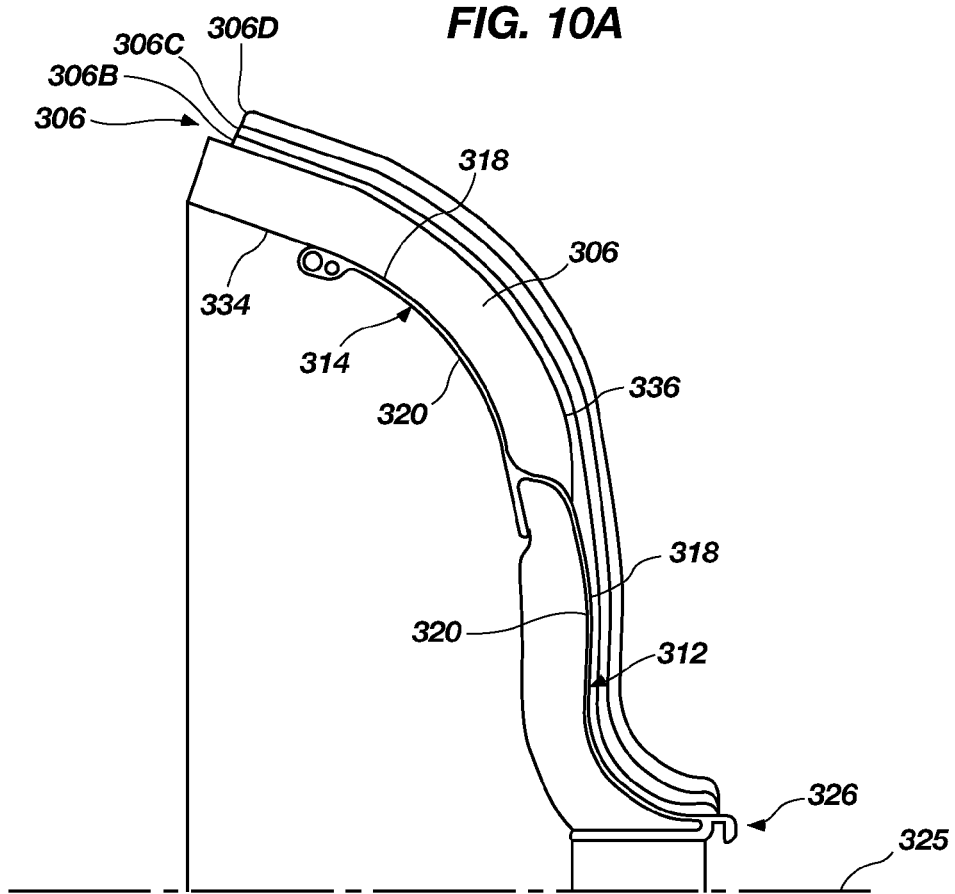
FIG. 10B is a side view of the occluder frame segment, depicting a portion of a tissue growth member attached to the occluder frame segment, according to the present invention.

With respect to FIG. 10B, a side view of the single occluder frame segment 310 with the tissue growth member 306 attached thereto is shown. The tissue growth member 306 may include an inner surface 334 and an outer surface 336, the inner surface 334 and outer surface 336, at least partially, in contact with the collapser portion 312 and the expander portion 314 of the occluder frame segment 310. The tissue growth member 306 may extend from the base portion 326 of the occluder frame segment 310 such that an outer surface 336 of the tissue growth member 306 is in contact with the inner surface 320 of the collapser portion 312 of the occluder frame segment 310. Further, the occluder frame segment 310 may extend through the tissue growth member 306 so that the outer surface 318 of the expander portion 314 may contact the inner surface 334 of the tissue growth member 306.

With this arrangement, the intermediate extension 316 extends radially inward such that the tissue growth member 306 is positioned between a portion of the collapser portion 312 and the intermediate extension 316. Thus, the intermediate extension 316 may assist in holding or attaching the tissue growth member 306 to the occluder frame segment 310. As the occluder system 302 is drawn in a catheter, the outer surface 318 of the collapser portion 312 may contact an inner surface of a catheter lumen and assist in collapsing the tissue growth member 306. Likewise, as the occluder system 302 is deployed from a catheter, the outer surface 318 of the expander portion 314 is configured to assist in expanding the tissue growth member 306 to a position similar to that depicted (it is noted that only the upper half of the tissue growth member 316 is shown in cross-sectional view in FIG. 10B).

The tissue growth member 306 may also include a plurality of layers of material. In various embodiments, such layers may include similar or dissimilar materials bonded together by adhesive or by heat processes or other appropriate processes known in the art. Such additional layers may include, for example, an expanded polytetrafluoroethylene (ePTFE) attached to the outer surface of a primary layer of the tissue growth member. In one embodiment, the tissue growth member 306 may include a primary layer 306A formed of a polyurethane foam, as set forth in the previous embodiments. The tissue growth member may further include additional layers 306B-306D of materials such as ePTFE thermally bonded with each other. In one particular example, the outer-most or proximal-most layers 306C and 306D may be formed of an ePTFE material having an internodal distance (sometimes referred to as pore size) of approximately 70 µm to approximately 90 µm. The layer of material (306B) adjacent the primary layer 306A may be formed of an ePTFE material having a reduced internodal distance relative to one or more of the outer layers 306C and 306D. For example, the internodal distance of this layer 306B may be approximately 10 µm. This layer 306B may be bonded or adhered to the primary layer using an adhesive material. Any other suitable sized layers of ePTFE may be employed, such as ePTFE having an internodal distance up to about 250 µm.

Such a configuration effectively prevents the passage of blood, due to the small internodal distance and pore size of layer 306B, while the larger internodal distance of other layers (e.g., 306C and 306D) enable tissue in-growth and endothealization to occur. Additionally, the primary layer, being formed of a polyurethane foam, enables aggressive growth of tissue from the LAA wall into the tissue growth member 306. It is noted that the use of appropriate adhesive materials between the primary layer 306A and the next adjacent layer 306B may also serve to fill in the pores of the next adjacent layer 306B and further inhibit possible flow of blood through the tissue growth member 306.

With reference now to FIGS. 11A, 11B and 11C, components of the anchor system 304 are shown including a first anchor segment 350a (FIG. 11A), a second anchor segment 350b (FIG. 11B) and a third anchor segment 350c (FIG. 11C), each shown in an expanded configuration. Each anchor segment 350a-350c may include a first anchor portion 352 and a second anchor portion 354, each of which may be substantially similar. Each of the first and second anchor portions 352 and 354 extend between a first outer end 356 and a second inner end 358, the first outer end 356 extending from a location that is adjacent an anchor leg extension 360. The second inner end 358 extends from an anchor hub base 362. The anchor leg extension 360 may extend slightly radially inward (toward a longitudinal axis 325 of the device) and distally to a free end 364. The first outer end 356 of the anchor segment portions 352 and 354 may also include a proximal protrusion 366. The proximal protrusion 366, on its own or together with a portion of the leg extension 360, may define a notch 368. The notch 368 and the anchor leg extension 360, and their relationship with other components, will be discussed in further detail hereafter.

The anchor hub base 362 may vary in structure between each of the first anchor segment 350a, the second anchor segment 350b, and the third anchor segment 350c to include a first anchor hub base 362a, a second anchor hub base 362b, and a third anchor hub base 362c, respectively. Such structural variation between each anchor hub base may be employed to facilitate interconnection between the individual anchor hub bases 362a-362c to form, at least in part, the anchor hub system 370 (best shown in FIG. 13), described in further detail hereafter.

As set forth, each anchor frame segment 350-350c may include a first anchor portion 352 and a second anchor portion 354, which, when in the expanded configuration, may form a first loop configuration and a second loop configuration, respectively. As in the previous embodiments, the first and second anchor portions each include engaging members 372 or protruding nubs sized and configured to be positioned at a distal side and on an outer surface of each of the first and second anchor portions 352 and 354 when the anchor frame segments 350 are fully expanded so that the first and second anchor portions 352 and 354 are positioned against tissue in the LAA.

Figure 12A:
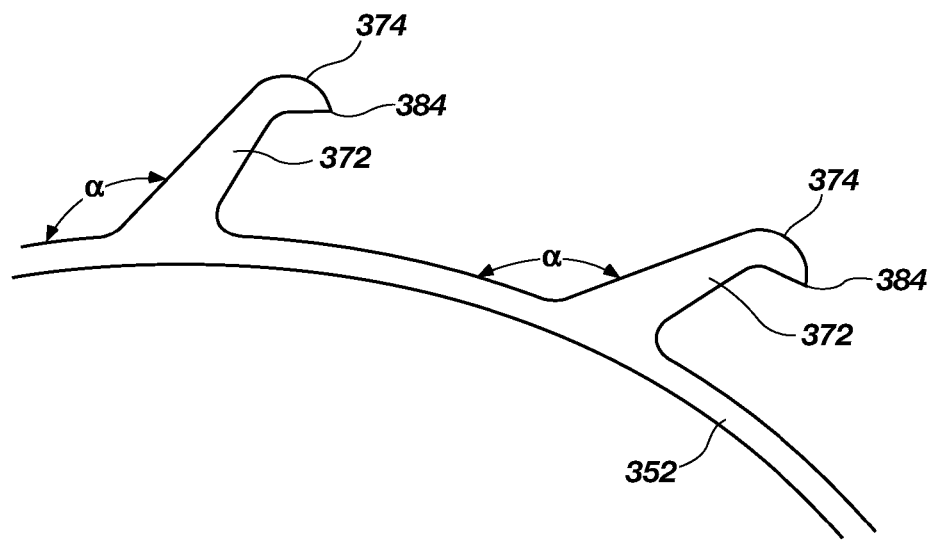
FIG. 12A is an enlarged view of detail "12A" taken from FIG. 11A, depicting engaging members extending from the anchor frame segments, according to one embodiment of the present invention.

With reference to FIG. 12A, the engaging members 372 may include what may be termed a wave-crest configuration such that the engaging members 372 are oriented and configured to provide traction or engagement with tissue via a tapered edge 384 and such that the engaging members 372 only aggressively engage tissue when the medical device experiences a displacing force in a proximal direction, or otherwise said, in the direction toward the opening or ostium of the LAA. Further, such wave-crest configuration of the engaging members may include a peak portion 374 that transitions to the edge 384. The peak portion 374 or outer surface of the engaging members may be blunt or obtuse. As shown in FIG. 12A, the peak portion may be generally rounded to substantially prevent the engaging members 372 from piercing or penetrating the tissue of the LAA. In addition, the engaging members 372 may be oriented such that the engaging members 372 may extend at an angle α of about one hundred thirty-five degrees from a distal side of the engaging member 372 relative to a tangent of a surface of the anchor portion 352 to, thereby, further prevent the engaging members 372 from piercing tissue while also preventing proximal movement of the medical device.

Figure 12B:
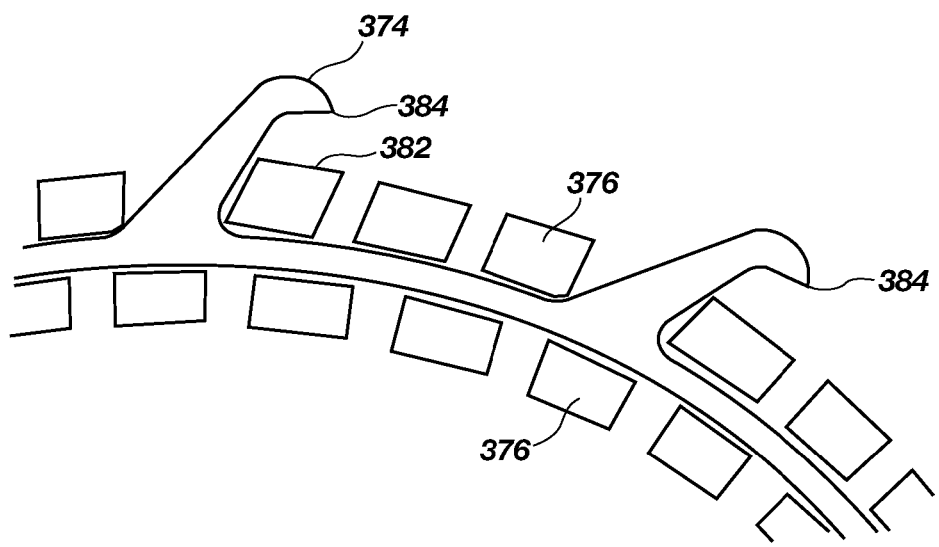
FIG. 12B is another embodiment of an anchor frame segment, depicting a wire wrapped around the anchor frame segment, according to an embodiment of the present invention.

With reference to FIG. 12B, in another embodiment, each anchor portion 352, 354 of each of the respective anchor frame segments 350-350c may include a wire 376 or other elongated structure wrapped therearound to form a coil configuration. The wire 376 may extend in the coil configuration between a first wire-connect portion 378 and a second wire-connect portion 380 (see FIG. 11A). The wire 376 may be configured such that an radially outer surface 382 is radially inward of the height of the peak portion 374 of the engaging members 372 and also radially inward (or below) the edge 384 of the engaging members 372. In one embodiment, the wire 376 may be made of a metal or a metal alloy such as stainless steel or titanium, but is not limited to such, and may be formed of other suitable materials, such as Nitinol, a polymeric material, a filamentary member or other metals and alloys. Such wire 376 may be employed to enhance engaging with the tissue in the LAA as well as provide a safety feature in the event that the anchor portions 352 or 354 of the anchor frame segments 350a-350c ever become fatigued and fracture.

Figure 13:
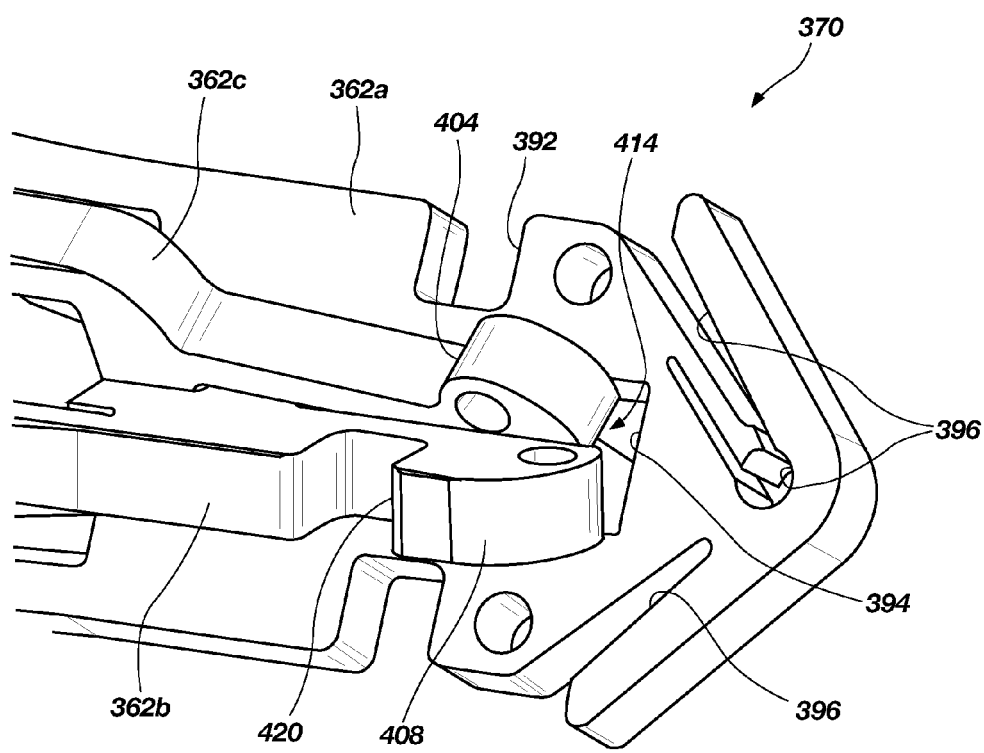
FIG. 13 is a perspective view of an anchor hub system, according to an embodiment of the present invention.

Referring back to FIGS. 11A, 11B and 11C, discussion relating to the anchor hub base will now be provided. As set forth, the anchor hub base 362a-362c for each anchor frame segment 350a-350c may include varying structure such as differently sized and configured notches and slots that may facilitate interconnection of the hub bases 362a-362c to form the anchor hub system 370 (FIG. 13). For example, referring specifically to FIG. 11A, the first anchor hub base 362a may define, among other things, a first rear notch 390, first retaining notches 392, a first hole 394 and first slots 396. The first rear notch 390 may be defined between the two second inner ends 358 extending from the first and second anchor portions 352 and 354. The first retaining notches 392 may be defined within an intermediate portion of the first anchor hub base 362a at opposite sides thereof. The first hole 394 may be defined proximal of the first retaining notches 392 and the first slots 396 may be defined at a proximal end portion 398 of the first anchor hub base 362a and, as shown in FIG. 11A, may be formed at angles relative to the longitudinal axis 325 that extends through the first rear notch 390 and the first hole 394.

With respect to FIG. 11B, similar to the first anchor hub base 362a, the second anchor hub base 362b may define a second rear notch 402 and second retaining notches 404. (It is noted that the use of the terms "first," "second" and "third" in the present discussion are for convenience in associating the notches, holes or other features with a given hub base 362a-362c and not to denote a particular number of notches associated with a particular hub base 362a-362c). In addition, the second anchor hub base 362b may define a deep second proximal notch 406. As such, the second rear notch 402 may similarly be defined between the two second inner ends 358 extending from the first and second anchor portions 352 and 354 of the second anchor segment 350b. The second retaining notches 404 may be defined within an intermediate portion of the second anchor hub base 362b disposed at opposite sides thereof. The second proximal notch 406 may be defined and extend from a proximal end of the second anchor hub base 362b between oppositely extending second protrusions 408 that at least partially define the second retaining notch 404. Further, the second proximal notch 406 may be sized and configured to be positioned over the first rear notch 390 of the first anchor hub base 362a such that the second retaining notches 404 substantially correspond and align with the first retaining notches 392 and so that the second rear notch 402 associates and corresponds with the first rear notch 390 (see FIG. 11A).

Referring now to FIG. 11C, the third anchor hub base 362c may include a base 410 with two base extensions 412. The base 410 may extend transverse relative to the two second inner ends 358 of the first and second anchor portions 352 and 354 of the third anchor segment 350c. The two base extensions 412 may extend proximally from the base 410 to provide two opposing pawls 414 facing each other such that, when in a relaxed condition, the pawls may be in contact with one another. The two base extensions 412 and pawls 414 may be displaced radially outwardly, as shown by arrows 416, to collectively define a third proximal notch 418. The third proximal notch 418 may be sized and configured to receive the first rear notch 390 of the first hub base 362a and the second rear notch 402 of the second hub base 362b so that the two base extensions 412 extend over the first anchor hub base 362a and the pawls 414 latch into the first hole 394 of the first anchor hub base 362a (see FIGS. 11A and 13). The third anchor hub base 362c also may define third retaining notches 420 defined by a back-side of the pawls 414 (i.e., the opposing, radially outer surface of the extensions) and a proximal side of the base 410 of the third anchor hub base 362c.

With reference now to FIG. 13, the anchor hub system 370 with each of the first anchor hub base 362a, the second anchor hub base 362b and the third anchor hub base 362c interconnected together is shown. As depicted, the second anchor hub base 362b and the third anchor hub base 362c are sized and configured to interconnect to the first anchor hub base 362a to form the anchor hub system 370. The second anchor hub base 362b and the third anchor hub base 362c may each be positioned and oriented desired angles relative to the first anchor hub base 362a such that the orientation of each hub base may substantially corresponds with the orientation of each of the anchor portions (not shown). Further, the pawls 414 of the third anchor hub base 362c are positioned to extend into the first hole 394 defined in the first anchor hub base 362a with the protrusions 408 of the second anchor hub base 362b adjacent to the pawls 414 and the first hole 394 of the first anchor hub base 362a. In this manner, the first, second and third retaining notches 392, 404, 420 may be substantially aligned such that a band, wire or other retaining device (not shown) may be wrapped therearound to ensure each of the first, second and third anchor hub bases 362a-362c remain interconnected to maintain the assembly of the anchor hub system 370. As depicted, the first anchor hub base 362a includes the first slots 396 defined in a proximal portion thereof. Such first slots 396 may be sized and configured to interconnect to a release line or tether (not shown) positioned within a coil or pusher member (not shown) similar to that described previously with respect to FIGS. 3B and 8A. As such, when appropriate, the anchoring hub system 370 can be released, along with other lines attached to other portions of the medical device (discussed in further detail below), to facilitate release of the medical device in the LAA.

Figure 14A:
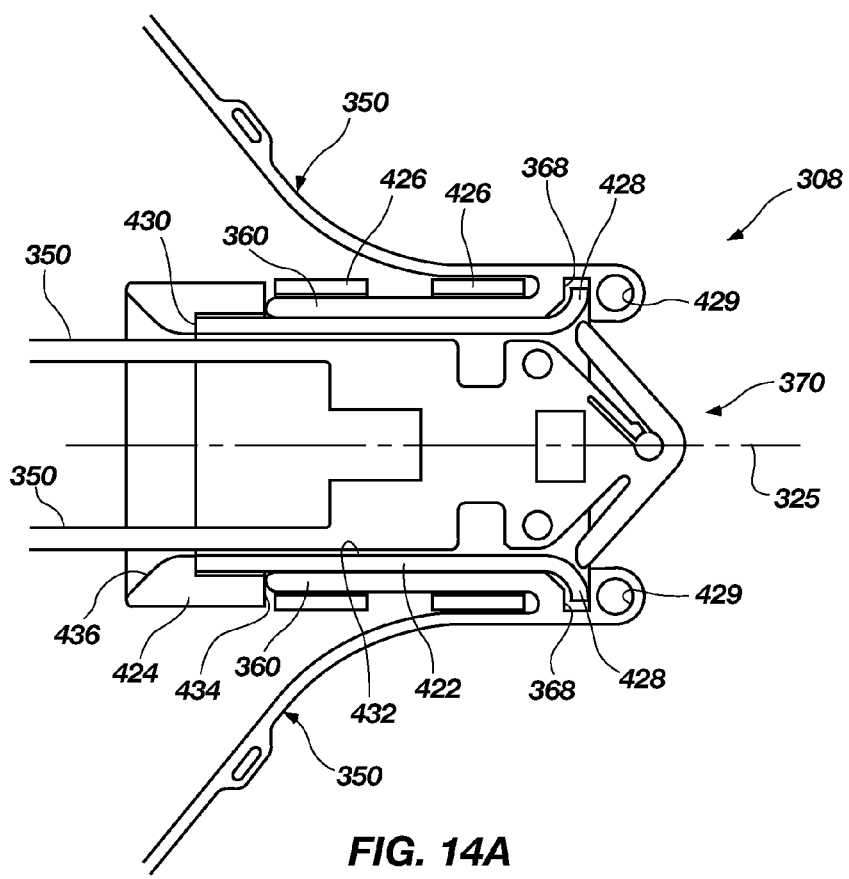
FIGS. 14A and 14B are cross-sectional side views of respective anchor frame segments and occluder frame segments interconnected to a hub system of a medical device according to one embodiment of the present invention.
Figure 14B:
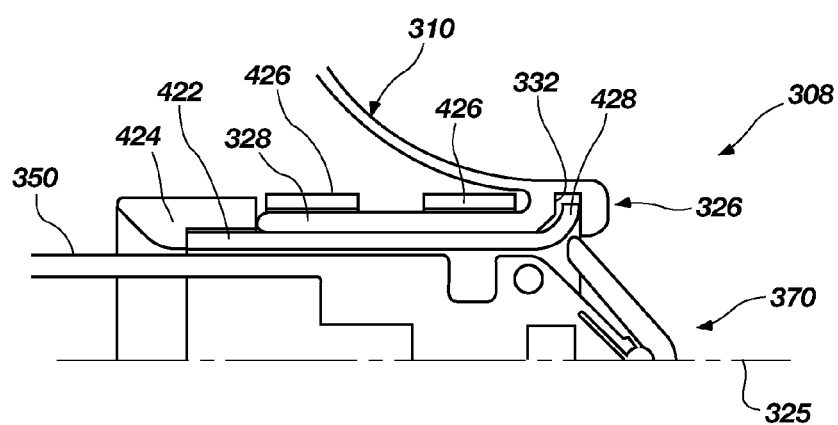

With reference now to FIGS. 14A and 14B, cross-sections of a hub system 308, including anchor leg extensions 360 and occluder leg extensions 328, respectively, are shown. For clarity purposes, the anchor hub system 370 is simplified and only partially shown. Further, attachment of the hub system 308 to a catheter system is not shown, but may be similar to that previously described with respect to FIGS. 3B and 8A.

With respect to FIGS. 11A and 14A, the hub system 308 or primary hub system may include, among other things, a hub member 422, a distal end cap 424 and one or more rings 426. The hub member 422 may include a proximal flared portion 428 and a distal end portion 430 to define a bore 432 having axis 325 extending therethrough. The distal end cap 424 may include a proximal end 434 and a funnel portion 436. The proximal end 434 may slide over a distal end portion 430 of the hub member 422 to interconnect with the hub member 422 so that each end of the bore 432 of the hub system 308 exhibits a flared surface. In another embodiment, the distal end of hub member 422 may be flared after the installation of rings 426 to exhibit a flared surface, similar to that provided by the distal end cap 424. Such process would eliminate the distal end cap 424 and a weld.

The funnel portion 436 of the distal end cap 424 may act as a guide to facilitate the anchor portions (not shown) of the anchor segments to easily invert or pull into a catheter by pulling on the anchor hub system 370. Likewise, the proximal flared portion 428 of the hub member 422 facilitates the anchor portions (not shown) of the anchor segments to evert or push out of the hub system 308. It is also contemplated that the funnel portion 436 of the distal end cap 424 and/or the proximal flared portion 428 of the hub member 422 may include grooves or the like that may be defined therein to associate and correspond with the anchor portions of the anchor segments to further act as a guide to assist in maintaining precise alignment of, and substantially preventing overlap between, the anchor portions as they are being respectively pulled or pushed through the hub system 308. As with previously described embodiments, one or more openings 429 may be located at a proximal end of the anchor frame segment 350 for reversibly attaching a release line (not shown) or tether to facilitate release of the medical device.

Figure 15:
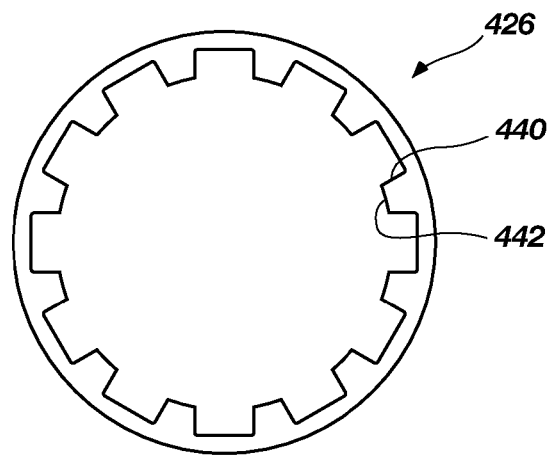
FIG. 15 is an end view of a ring utilized in the hub system of FIG. 14A, according to one embodiment of the present invention.

The flared portion 428 of the hub member 422 may be sized and configured to be disposed within the notch 368 defined adjacent the first outer ends 356 of the anchor frame segments 350 so that the anchor leg extensions 360 of the anchor segments 350 extend distally along an outer surface of the hub member 422. The one or more rings 426 may then be positioned over the anchor leg extensions 360. As depicted in FIG. 15, the one or more rings 426 may have multiple notches 440 defined an inner surface 442 of the ring, each notch 440 being sized and configured to receive a corresponding anchor leg extension 360 (FIG. 14A) or an occluder leg extension 328 (FIG. 14B) in an alternating arrangement. With this arrangement, the one or more rings 426 with the notches 440, may be employed to hold the anchor segments 350 and the occluder frame segments 310 to the hub system 308 in a desired pattern or arrangement. Further, the outer surface of the leg extensions 360 and the leg extensions 328 (FIG. 14B) may include ramps (not shown) that facilitate the rings 426 to slide over the leg extensions 360 and 328 and snap/lock the rings 426 into position.

With reference now to FIGS. 10A and 14B, the hub system 308 is shown to illustrate the occluder frame segment 310 attached to the hub system 308. Similar to the leg extensions 360 of the anchor frame segment 350 (FIG. 14A), the occluder frame segments 310 also each may include an occluder base portion 326 defining a notch 332 to receive the proximal flared portion 428 of the hub member 422 and occluder leg extensions 328 to be captured within a corresponding notch 440 (FIG. 15) of the one or more rings 426. It is noted that a portion of only one occluder frame segment 310 and the upper half of the hub system 308 is shown in FIG. 14B for purposes of convenience and clarity.

Figure 16:
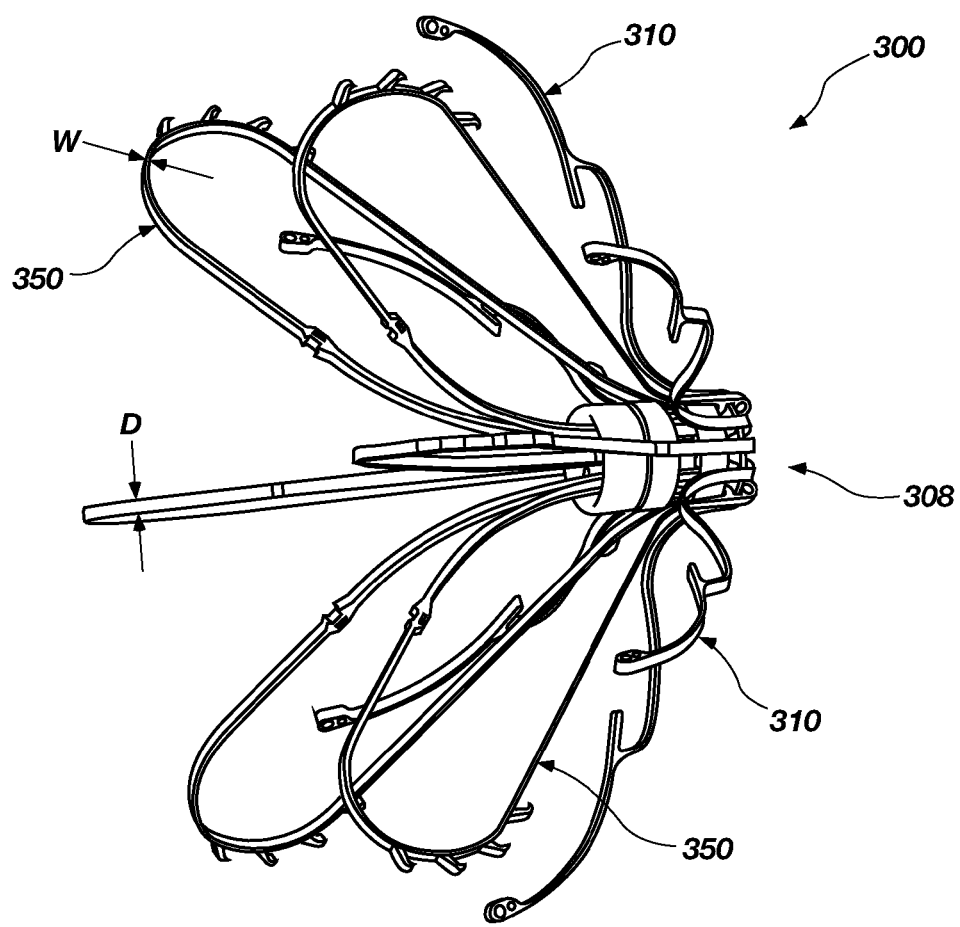
FIG. 16 is a perspective side view of the medical device (without a tissue growth member) of FIGS. 9A and 9B, according to the present invention.

FIG. 16 is a perspective view of the medical device 300 (with out the tissue growth member), illustrating the hub system 308 interconnected with the occluder frame segments 310 and the anchor frame segments 350, with the one or rings 426 positioned to capture each of the occluder and anchor frame segments 310 and 350. Further, it should be noted that the occluder frame segments 310 and anchor frame segments 350 are positioned around the hub system 308 in an alternating arrangement (i.e., each occluder frame segment 310 is disposed between two anchor frame segments 350 and vice versa).

Also, it is noted that the occluder frame segments 310 and the anchor frame segments 352 are separate and discrete components of the medical device 300. Further, such occluder frame segments 310 and anchor frame segments 352, as in the previous embodiments, deploy separately, wherein the occluder frame segments 310 may deploy first so that a physician can readily determine the best position and orientation of the medical device 300 within the LAA and, once appropriately positioned and oriented, the physician can then deploy the anchoring frame segments 352 from the catheter (not shown), as set forth with respect to the previously described embodiments. Furthermore, as in previous embodiments, each of the occluder frame segments and the anchor frame segments may be laser cut from a Nitinol sheet, cut with structure and features to employ ready assembly of the medical device and with structural features to facilitate delivery and release of the medical device through a catheter system or medical device system. Of course other materials and methods of manufacture may also be used.

Figure 17A:
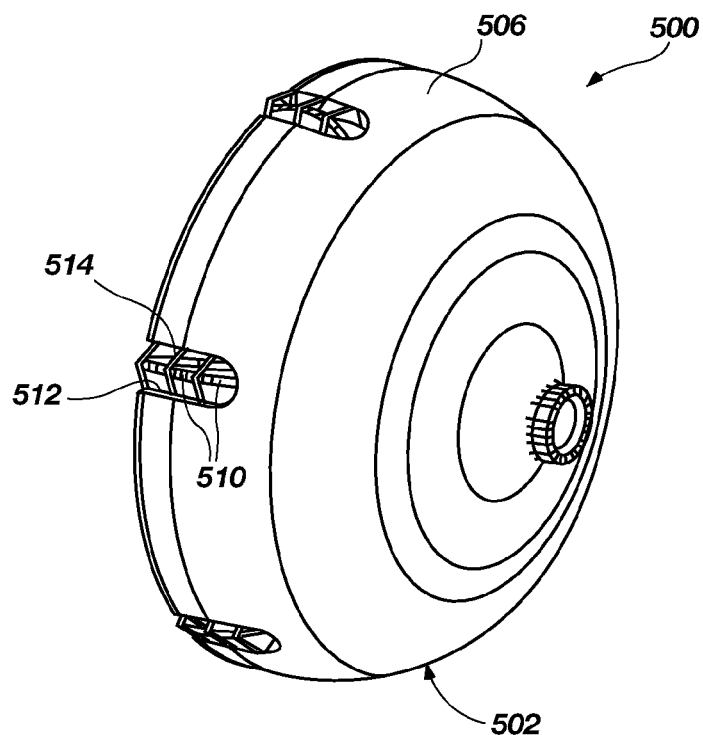
FIGS. 17A and 17B are proximal and distal perspective views of a medical device, according to another embodiment of the present invention.
Figure 17B:
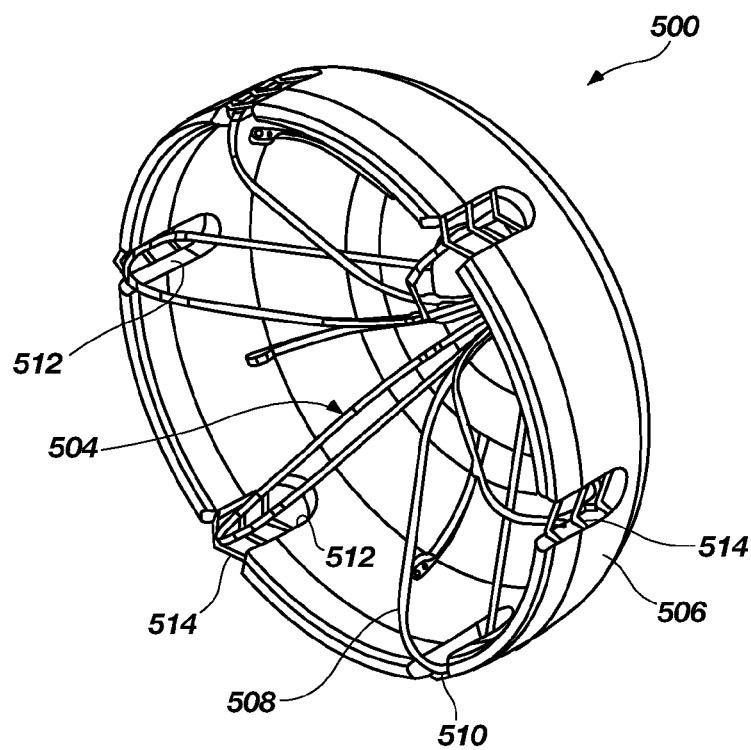

With respect to FIGS. 17A and 17B, proximal and distal views of another embodiment of a medical device 500 are shown. In this embodiment, the frame structure of the occluder system 502 and the anchor system 504 may be substantially similar to the previous embodiments set forth, but the tissue growth member 506 may include additional features. For example, the tissue growth member 506 may extend further distally such that the tissue growth member 506 extends a distal distance or extent similar to the distal distance or extent of the expanded configuration of the anchor system 504. Further, the tissue growth member 506 may include gaps 512 or open sections defined within a distal portion of the tissue growth member 506. Such gaps 512 may be areas where portions of the tissue growth member 506 have been removed. The gaps 512 defined in the tissue growth member 506 may be positioned to correspond or align with the anchor portions 508 or anchor loops of the anchor system 504. In this manner, as the anchor system 504 is expanded to an in-use state or expanded position, the anchor portions 508, including any engagement members 510 or nubs, will bias against tissue in the LAA without the material of the tissue growth member 506 obstructing the anchor portions 508. Additionally, the increased length of the tissue growth member 506 may abut the tissue in the LAA (not shown) and provide increased surface area contact therewith.

Furthermore, one or more reinforcement lines 514 may extend across the gaps 512 defined in the tissue growth member 506. The reinforcement lines 514 may extend generally laterally or transverse relative to the expanded anchor portion 508. In one embodiment, the reinforcement lines 514 may be a polymer thread or line attached to the tissue growth member 506 employing a heat process. With this arrangement, the expanded anchor portion 508 may abut or bias an inner surface of the reinforcement lines 514 with the engaging members 510 extending beyond the reinforcement lines 514 to engage the tissue in the LAA. In the currently described embodiment, the lines 514 extending across the gaps 512 are spaced apart to help ensure that the engaging members 510 extend beyond the lines 514 while also providing a radial expansion limit to the anchor portions 508 (i.e., a limit regarding how far the anchor portions may radially extend when in the deployed state). Such reinforcement lines 514 may provide a safety mechanism in preventing, for example, the expanded anchor portions 508 from over expansion over time as tissue remodeling occurs in the tissues surrounding the implanted medical device 500.

Figure 18A:
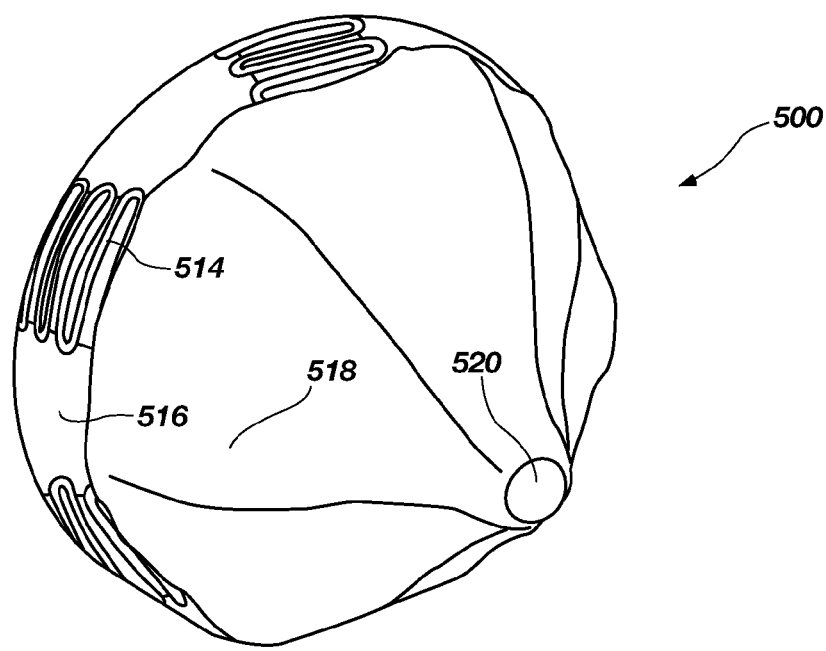
FIGS. 18A and 18B are proximal and distal perspective views of a medical device depicting multiple tissue growth members and layers, according to an embodiment of the present invention.
Figure 18B:
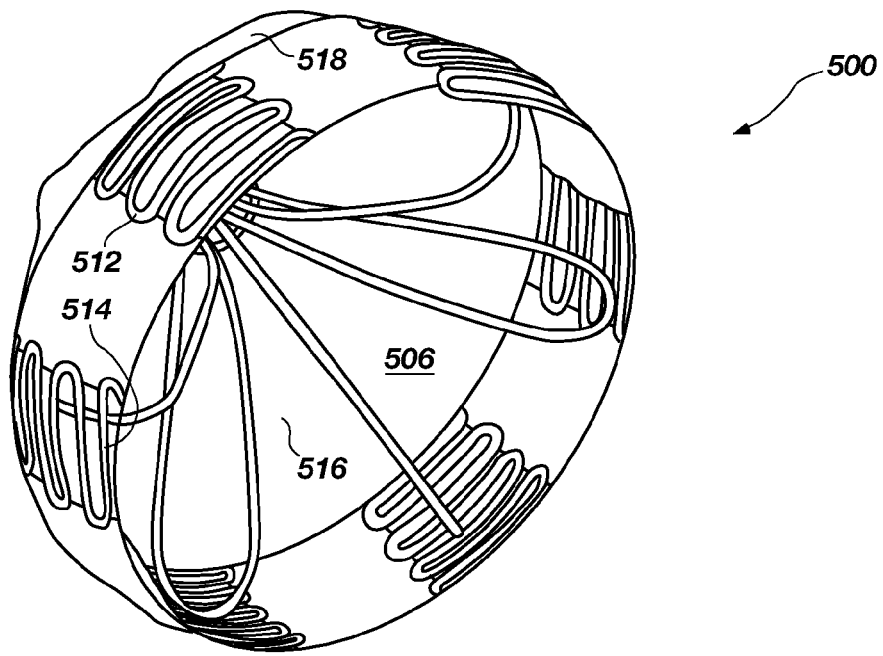

FIGS. 18A and 18B are distal and proximal views (photographed) of the medical device 500 with the gaps defined in the distally lengthened tissue growth member 506 with the reinforcement lines 514 extending across such gaps 512, according to another embodiment of the invention. In this embodiment, the tissue growth member 506 may include multiple material layers. In one embodiment, the material layers of the tissue growth member 506 may include one or more first layers 516 and one or more second layers 518. The one or more first layers 516 may include foam, such as polyurethane foam, and the one or more second layers 518 may include ePTFE, similar to that described in earlier embodiments.

The ePTFE may include multiple layers, such as two to four layers, or more. Such ePTFE layers may also include different thicknesses and/or internodal distances, as previously described. The multiple layers of ePTFE may be sized to substantially prevent blood and thrombi from passing therethough. The ePTFE layers may be attached to each other employing a thermal or sintering process or any other known process in the art, such as with an adhesive. The one or more layers of ePTFE may be adhesively attached to the foam layer. In one embodiment, the adhesive layer provided to attach the ePTFE layer to a foam layer also fills the pores on one side of the ePTFE to further provide a tissue growth member that substantially prevents blood and thrombi from passing therethrough. Further, the surface of the ePTFE on the proximal side of the tissue growth member 506 provides a porous surface that readily facilitates blood cell lodging and attachment to promote tissue growth and endothealization as this is the surface that is exposed to the left atrium ("LA") of the heart (not shown).

In another embodiment, as shown in FIG. 18A, the medical device 500 may include a hub tissue growth member 520. In this embodiment, the hub tissue growth member 520 may be sized and configured to cover the proximal side of the hub (see FIGS. 14A and 14B) of the medical device 500. As depicted, with both the tissue growth member 506 and the hub tissue growth member 520, there is substantially no exposure of the frame structure of the medical device 500 at the proximal face of the medical device 500. This feature is advantageous since when the medical device 500 is positioned in the LAA, the proximal face is the surface that is exposed to the LA, thereby substantially eliminating the potential of emboli or thrombus escaping from the LAA to the LA and/or migrating from exposed frame structure surfaces. In one embodiment, the hub tissue growth member 520 may be formed from multiple layers of ePTFE and/or foam, similar to the tissue growth member 506, previously set forth.

Figure 19:
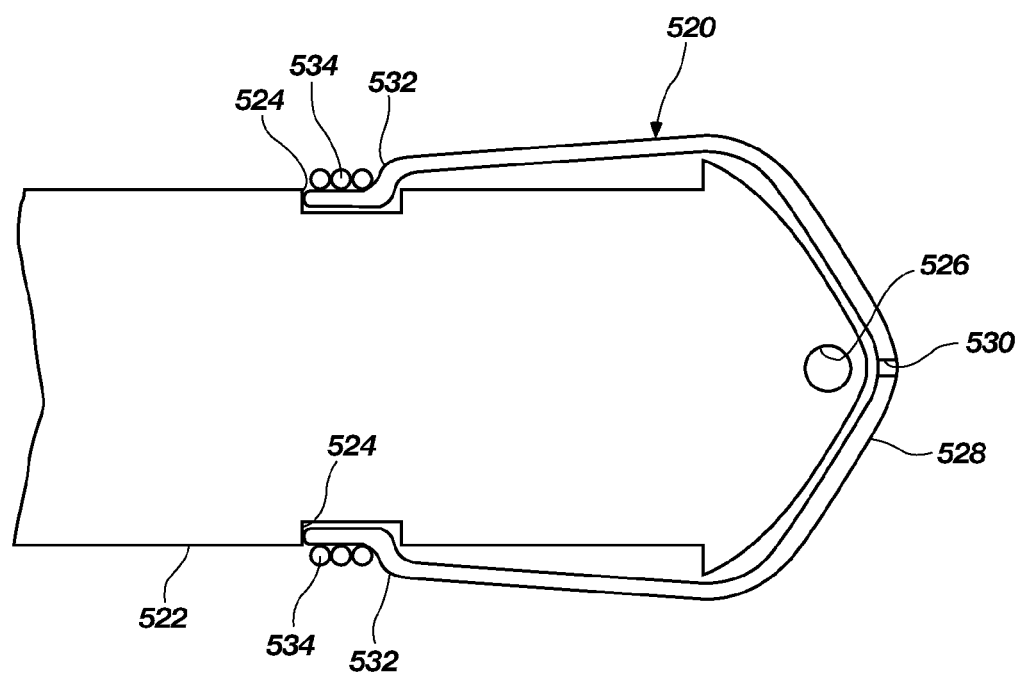
FIG. 19 is a cross-sectional view of a portion of the medical device, depicting an anchor hub with a hub tissue growth member attached thereto, according to an embodiment of the present invention.

FIG. 19 is a partial cross-sectional view of the anchor hub 522 (in simplified form), depicting the hub tissue growth member 520 attached to the anchor hub 522. One embodiment of an anchor hub is previously described in detail and shown with respect to FIG. 13. The anchor hub 522 may include notches 524 defined in an outer surface of the hub (including one or more components of the hub). A hole or an eyelet 526 may also be formed in a proximal end of the hub 522. The hub tissue growth member 520 may include a sock-like member with a proximal face 528 and a distal end portion 532. The proximal face 528 of the hub tissue growth member 520 may include a pin hole 530 configured to be generally aligned with the eyelet 526 of the anchor hub 522. The pin hole 530 is sized and configured to allow a tether (not shown in FIG. 19) to extend therethrough for removable attachment to the eyelet 526 of the anchor hub 522. The hub tissue growth member 520 may be sized and configured to fit over the anchor hub 522 to extend at least to the notches 524 of the anchor hub 522. The hub tissue growth member 520 may be attached to the anchor hub 522, for example, with one or more rings 534 or ring-like members (including helical type rings) that may be readily expanded over the anchor hub 522 and tightened over the hub tissue growth member 520 within the notches 524 formed in the anchor hub 522. In other embodiments, a thread or filamentary member may be wrapped around the hub tissue growth member 520 and cinched within the notches to retain the hub tissue growth member 520 over the anchor hub 522. Other means may also be used to keep the hub tissue growth member 520 in a desired position. With this arrangement, the anchor hub 522 and, more importantly, the proximal face 528 of the anchor hub 522 may be covered with the hub tissue growth member 520 to optimize the surface exposed to the LA for endothealization and to prevent emboli or thrombus from migrating between the LAA and the LA.

Figure 20:
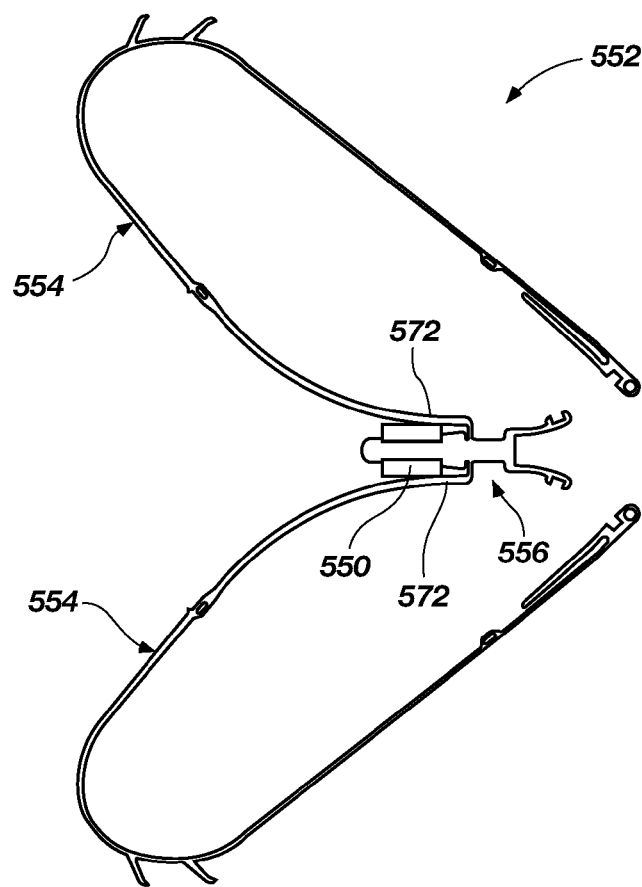
FIG. 20 is a side view of a single anchor segment of the anchoring system, depicting a dissolving member providing support to anchor portions of the anchor segment, according to one embodiment of the present invention.

In another embodiment, the medical device may include a dissolving member 550 configured to provide a limited period in which the loop portions 554 of the anchor segments 552 in the anchor system are biased or provide outward expansion against tissue within an LAA (not shown). For example, FIG. 20 depicts the dissolving member 550 interconnected to the anchor hub base 556. For simplification purposes, only one anchor segment 552 is shown with the dissolving member 550. Such a dissolving member 550 may be made of a bio-absorbable material, but may also be made from a bio-resorbable material or a bio-degradable material or combinations thereof. As depicted, the dissolving member 550 may positioned circumferentially about and distally adjacent the anchor hub base 556 such that the loop portions 554 of the anchor segments 554 are biased by, or may be supported by or against, the dissolving member 550 adjacent the proximal inner end 572 of the loop portions 554.

With this embodiment, the anchoring system can perform and function similar to that described in the previous embodiments when implanted in the LAA and for a sufficient time while the occluder system (not shown) endothelialized with the tissue in the LAA. After a predetermined time period, the dissolving member 550 degrades or dissolves into the body such that the dissolving member 550 is no longer a component of the medical device. As such, it is no longer present to provide support to the loop portions 554 of the anchor segments previously provided. Thus, the loop portions 554 of the anchor segments 552 will not provide the same biasing force against the tissue of the LAA and, instead, will fold or bend (or otherwise be displaced) inward due to structural features in the anchor hub base 556, described below.

Figure 20A:
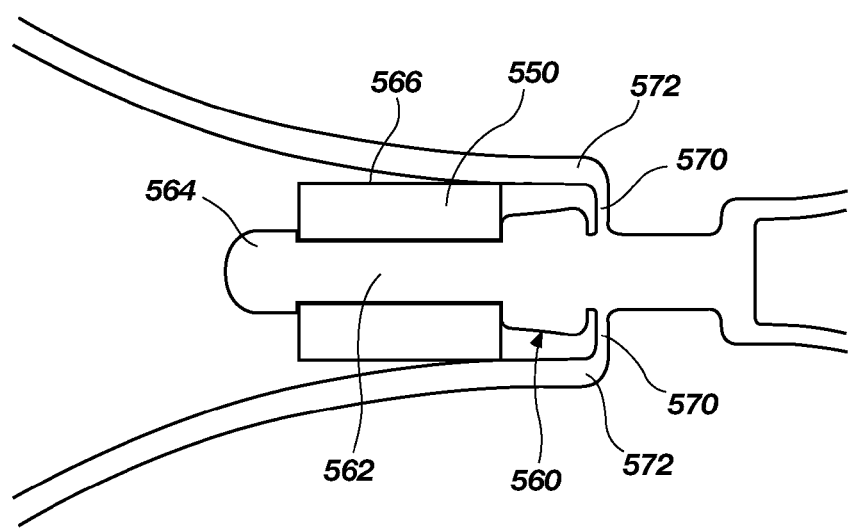
FIG. 20A is an enlarged view of the dissolving member coupled to the anchor segment of FIG. 20, according to an embodiment of the present invention.

FIG. 20A is an enlarged view of the dissolving member 550 connected to the anchor hub base 556, as depicted in FIG. 20. The dissolving member 550 may be, for example, a cylindrically shaped member, or any other suitable shape, sized and configured to slide over or otherwise surround a distal hub extension 560. The distal hub extension 560 may extend distally and centrally from one of the anchor hub bases 556 of the anchor segments 552. Further, the distal hub extension 560 may include a recessed central region 562 and an enlarged distal portion 564. The recessed central region 562 may be sized and configured to receive the dissolving member 550 and the enlarged distal portion 564 may be sized and configured to prevent the dissolving member 550 from disengaging or self-migrating from the distal hub extension 560.

As depicted, the loop portions 554 are disposed against or supported by the dissolving member 550 on an outer surface 566 of the dissolving member 550. The proximal inner end 572 of the loop portions 554 are interconnected to the anchor hub base 556 with a relatively thin extension 570 disposed therebetween. Such thin extension 570 may be sized and configured to limit the outward force of the loop portions 554 against the tissue of the LAA by facilitating collapse of the loop portions 554 once the dissolving member 550 has dissolved into the body. In other words, once the dissolving member 550 is dissolved, the thin extension 570, being configured to be relatively non-supportive and flexible, will not provide adequate support for the loop portions 554 to remain biased against the tissue, thereby, allowing collapse (or radially inward displacement) of the loop portions 554. In this manner, the combination of the dissolving member 550 and the thin extension 570 employ means by which the medical device may be anchored in the LAA and, after a predetermined period of time in which the dissolving member 550 dissolves, the loop portions 554 of the anchoring system may collapse or become limp with respect to the tissue in the LAA. As noted above, the dissolving member may be designed to dissolve within a desired time period. For example, the dissolving member 550 may be configured such that it dissolves within approximately the same time period as it is anticipated that endothealization will occur, or within a time period that correlates with a desired percentage or amount of endothealization to occur.

Now referring to FIG. 21, a medical device delivery system 600 is shown, according to another embodiment of the present invention. The medical device delivery system 600 may include a medical device 602, a sheath 604 and catheter system 608 coupled to a handle system 610. For purposes of reference, an axis 601 is defined as extending through the medical device delivery system 600. The medical device 602 may include any medical device configured to be interventionally implanted within the human anatomy including any one of the medical devices, or combinations thereof, described herein, such as the medical device that will be described in association with this embodiment. The sheath 604 may be an elongated member defining a sheath lumen 606 extending axially therethrough between a proximal end and a distal end of the sheath 604. The sheath may be a discreet, independent member (not permanently coupled to the delivery system) sized and configured to receive the catheter system 608 through the lumen 606 of the sheath 604. It is also contemplated that the sheath 604 be incorporated with a sheath handle system, which is separate from the handle system 610 described in conjunction with the present embodiment, that may be configured to articulate a distal end portion of the sheath.

With respect to FIGS. 21 and 21C, the catheter system 608 may include a catheter 622, such as an elongated extruded catheter or member, with multiple lumens extending along an axial length between a distal end and a proximal end of the catheter 622. For example, the multiple lumens may include a central lumen 624 and one or more peripheral lumens 626, such as the two peripheral lumens shown in FIG. 21C. Further, the catheter system 608 may include multiple tethers extending through the multiple lumens defined in the catheter, the tethers extending and interconnected to and between the medical device 602 and the handle system 610.

For example, the catheter system 608 may include one or more occluder tethers 628 and one or more anchor tethers 630. The central lumen 624 may be sized and configured to receive the anchor tether 630 and the one or more peripheral lumens 626 may be sized and configured to receive the occluder tethers 628. The anchor tether 630 may include an anchor pusher 632, such as a coil or other generally tubular member, with the anchor pusher 632 defining an anchor pusher lumen 634 extending longitudinally therethrough and multiple wires extending through the anchor pusher lumen 634. Similarly, the occluder tether 628 may include an occluder pusher 636, such as a coil or other generally tubular member, defining an occluder pusher lumen 638 extending longitudinally therethrough and multiple wires extending through the occluder pusher lumen 638. Each of the anchor pusher 632 and the occluder pusher 636 may include a polymeric layer formed therearound.

The occluder tethers 628 and the anchor tether 630 may be connected to the medical device 602 via the multiple wires, the multiple wires extending through the respective occluder pushers 636 and anchor pusher 632 and extending into and interconnected to the handle system 610. Distal ends of each of the occluder pushers 636 and the anchor pusher 632 may not be directly connected to the medical device 602. The multiple wires may include, for example, a first wire 640 and a second wire 642, the first wire 640 being a pull wire and the second wire 642 being a pin wire. The first wire 640 and second wire 642, acting together, may facilitate interconnection and release of the medical device 602 as discussed in further detail herein. With this arrangement, the catheter system 608 may be configured to navigate the vasculature of a patient and push the medical device 602 through the sheath 604 to the LAA and facilitate manipulation and control of the medical device 602 at a distal portion 621 of the catheter system 608 via the handle system 610. Manipulation and control of the medical device 602 may include separating out and independently controlling various functions including, for example, the deployment functions of an anchor portion 603 (FIG. 21A) and an occluder portion 605 of the medical device 602, optimal positioning and repositioning of medical device 602 in the LAA, re-deployment after fully anchoring the device in LAA, and withdrawing of the medical device 602 from the LAA after fully anchoring the medical device within the LAA.

Referring back to FIG. 21, the handle system 610 may include one or more handle portions, such as an occluder handle portion 612, an anchor handle portion 614 and a float handle portion 616, each of which may be utilized to employ different functions to control and manipulate the medical device 602 at the distal portion 621 of the catheter system 608. For example, by retracting the sheath 604, the occluder portion 605 may be deployed while the handle system 610 is in a first handle position. As depicted in FIGS. 21 and 21A, by distally moving the anchor handle portion 614 forward to a second handle position, as depicted by arrow 618, the anchor portion 603 of the medical device 602 may be deployed by everting or moving one or more anchors distally to a rolled-out position or an anchor deployed position. Also, as depicted in FIGS. 21 and 21B, by proximally moving the float handle portion 616 to a third handle position, as depicted by arrow 620, the catheter 622 may also retract to expose and deploy the occluder tethers 628 and the anchor tether 630 connected to the medical device 602 to enable determination of whether the medical device 602 is properly seated and positioned in the LAA.

With reference to FIGS. 21, 23 and 24, a more detailed description of the handle system 610 will now be provided. FIGS. 23 and 24 are cross-sectional views of the handle system 610, taken along section lines 23 and 24 shown in FIG. 22, FIG. 22. illustrating an end view of the proximal side of the handle system 610. Beginning on a distal side of the handle system 610, the float handle portion 616 may include an outer housing 644 defining a bore 646 extending axially through the outer housing 644 between a distal end and a proximal end thereof. The proximal end of the catheter 622 may be coupled to the distal end of the outer housing 644, such as by being inserted and secured within the bore 646 of the float handle portion 616. The proximal end of the float handle portion 616 may be slidably coupled to an inner extension 652 of the occluder handle portion 612, the inner extension 652 being sized and configured to slide within the bore 646 of the float handle portion 616. The float handle portion 616 may be limited to linear translation over the inner extension 652 such as by way of interaction between a groove 648 defined in the inner surface (within the bore) of the outer housing 644 and a guide 654 formed on the inner extension 652. The outer housing 644 of the float handle portion 616 may also be coupled to a float rod 650 extending proximally from the float handle portion 616 and through the occluder handle portion 612 as will be discussed in more detail hereafter. With this arrangement, the float handle portion 616 is linearly slideable over the inner extension 652 of the occluder handle portion 612. Since the proximal end of the catheter 622 is fixed within the bore 646 of the float handle portion 616, proximal movement, as indicated by arrow 620, of the float handle portion 616 will retract the catheter 622 of the catheter system 608 to, thereby, enable the float feature for the medical device 602, as previously discussed.

With respect to FIG. 24A, an enlarged view of a portion of the float handle portion, taken from detail "24A" of FIG. 24, is shown. To maintain the integrity of the occluder pusher 636 and associated wires (not shown in FIG. 24A) extending through the catheter system 608 and the handle system 610 when proximally moving the float handle portion 616, tubing 653, such as hypo-tubes, may be co-axially secured with the lumens defined in the inner extension 652 that, in turn, correspond co-axially with, and slidably extend toward, the peripheral lumens 626 defined in the catheter 622 (see FIG. 21). The lumens defined in the inner extension 652 may include a catheter portion corresponding to the configuration of the catheter 622 or may include an associated housing portion positioned within a bore defined in the inner extension 652. In this manner, as the float handle portion 616 is moved proximally, the occluder pusher (coils) and wires maintain a substantially straightened position while the catheter 622 is retracted. During the proximal movement of the catheter 622, the tubing 653 may be fixed within the inner extension 652 and slides within the peripheral lumens 626 defined in the proximal end of the catheter 622. The tubing 653 arrangement may therefore substantially prevent buckling of the coils and wires during proximal movement of the float handle portion 616 toward the inner extension 652.

Referring back to FIGS. 23 and 24, the occluder handle portion 612, or middle portion of the handle system 610, may include an outer housing 658, the above-identified inner extension 652 and an occluder-release slider 660. The outer housing 658 may define a bore 662 extending axially between a proximal end and a distal of the outer housing 658. Such outer housing 658 may be sized and configured to house the inner extension 652, the occluder-release slider 660 and a mode switch 664. The mode switch 664 may be secured in the outer housing 658 at the proximal end with mode support structure 666.

The inner extension 652 may extend axially through the bore 662 of the outer housing 658, coupled at one end to the mode support structure 666. The other end of the inner extension 652 extends axially and distally from the outer housing 658 of the occluder handle portion 612 and is slidably coupled with, and extends through a portion of, the float handle portion 616. The inner extension 652 may also extend through a slider bore 661 defined in the occluder-release slider 660. In the position depicted, the occluder-release slider 660 is fixed to the inner extension 652 via a notch 668 and a spring-loaded pawl 670 arrangement such that the pawl 670 may be moved from the notch 668 defined in the inner extension 652 to enable the occluder-release slider 660 to be moved proximally as will be discussed in more detail hereafter. The spring-loaded pawl 670 may be configured, for example, as a partial ring-type clip that may be positioned around the occluder-release slider 660 with the pawl 670 extending through a hole or slit 672 in the occluder-release slider 660 and further extending into the notch 668 of the inner extension 652.

With reference to FIGS. 24 and 24B, FIG. 24B depicts an enlarged portion of the occluder-release slider 660 coupled to occluder tether wires (shown as dashed lines). In one embodiment, the occluder-release slider 660 may define two holes 674 extending transverse relative to the axis 601 of the medical device delivery system 600 and which may be axially aligned with each other. Further, the occluder-release slider 660 may define a primary groove 676 formed in an outer surface of the occluder-release slider 660 that is sized and configured to secure the occluder tether wires thereto. Also, the inner extension 652 may define two opposing notched openings 678 extending generally between the bore of the inner extension 652 and the outer surface of the inner extension 652. The proximal ends of the notched openings 678 may extend to, and correspond with, the holes 674 of the occluder-release slider 660. The distal ends of the notched openings 678 extend to longitudinal guide grooves 680 defined in the inner surface of the occluder-release slider 660.

In one embodiment, there can be two sets of occluder tether wires. As previously set forth, each set of occluder tether wires may include the first wire 640 and the second wire 642, the first wire 640 being the pull wire and the second wire 642 being the pin wire (see also FIG. 21C). In regard to one set of the occluder tether wires, the first wire 640 may extend from the peripheral lumen 626, through one notched opening 678 of the inner extension 652, along the guide groove 680 defined in the occluder-release slider 660, around the distal end of the occluder-release slider 660 and toward the primary groove 676 to be circumferentially wrapped around and secured within the groove 676 The second wire 642 or pin wire may also extend through the notched opening 678 of the inner extension 652, through the hole 674 and around an outer surface of the occluder-release slider 660, and into the primary groove 676 to be wrapped and secured therein. The other set of occluder tether wires may be similarly secured to the occluder-release slider 660 by extending through the inner extension 652 on the opposite side thereof and wrapped around the primary groove 676 of the occluder-release slider 660, as depicted. It is also noted that the anchor tether 630 (shown as dashed line) axially extends through the occluder handle portion 612 toward the anchor handle portion 614.

With respect to FIGS. 23 and 23A, the mode switch 664 will now be discussed. As previously set forth, the occluder handle portion 612 may include the mode switch 664 at a proximal side thereof. The mode switch 664 may include a switch that is moveable, for example, between a first position and a second position. The mode switch 664 may be secured to the occluder handle portion 612 via the mode support structure 666. For example, as best depicted in FIG. 24, the mode support structure 666 may include a proximal end of the inner extension 652 or an inner disc member 667 secured to an outer disc member 669 with at least a portion of the mode switch 664 sandwiched therebetween. The inner disc member 667 may be sized to fit snugly within the outer housing 658 and the outer disc member 669 sized to cap-off the proximal end of the outer housing 658 of the occluder handle portion 612. The proximal end of the inner extension 652 may be fixed to the inner disc member 667. Such a configuration may be employed to sufficiently hold the mode switch 664 in position and facilitate translation of the mode switch 664 to multiple positions.

Referring again to FIGS. 23 and 23A, the mode switch 664 may include one or more key holes defined therein, such as a first key hole 682, a second key hole 684 and a third key hole 686. Each of the one or more key holes 682, 684 and 686 may be sized and configured to correspond with different portions of the handle system 610, such as a release rod 688, an anchor rod 690 and the float rod 650, respectively. Each of these rods may act as a key relative to the position of the mode switch 664 and their corresponding key holes. The release rod 688 and anchor rod 690 are fixed to the anchor handle portion 614 and extend distally therefrom, extending through the one or more key holes and into the occluder handle portion 612. The release rod 688 and anchor rod 690 may be selectively slideable through the occluder handle portion 612 relative to the mode switch 664. For example, the first key hole 682 may be sized and configured to receive a flattened section of the release rod 688 such that the release rod 688 may slide to different positions (or rotate) depending on the position of the mode switch 664. Likewise, the second key hole 684 may be sized and configured to receive the anchor rod 690, slideable therethrough depending on the position of the mode switch 664. Similarly, the third key hole 686 may be sized and configured to receive the float rod 650 such that the float rod 650 may be slidably displaced therethrough depending on the relative position of the mode switch 664. Additional detail regarding the mode switch 664, its positioning and the control and functionality it provides to the medical device delivery system 600 (FIG. 21), will be discussed in further detail below.

Referring back to FIGS. 21, 23 and 24, the anchor handle portion 614 may include an outer housing 692, an anchor handle fixed member 694 and an anchor-release slider 696, each defining axially extending stepped bores therein. Further, the anchor handle portion 614 may include a release-enable switch 698 disposed at a proximal end thereof (also see FIG. 22). Such structural components of the anchor handle portion 614 may be positioned relative to each other in a variety of ways. For example, the anchor handle fixed member 694 may be fixed to the anchor rod 690 such that the anchor rod 690 sealingly extends through the distal end of the anchor handle fixed member 694 into a larger portion of the bore defined in the anchor handle fixed member 694. The anchor-release slider 696 may be positioned over the proximal end of the anchor rod 690 and within the proximal side of the bore defined in the anchor handle fixed member 694.

The proximal side of the outer housing 692 may be positioned over both the anchor handle fixed member 694 and the anchor-release slider 696 with a fluid port 702 extending axially through the proximal side of the outer housing 692 and through the proximal portion of the anchor-release slider 696 to interconnect with the anchor rod 690 to facilitate fluid communication through the handle system 610 and to the catheter system 608. One or more sealing rings 704 may be employed for sealing interconnection between the fluid port 702 and the anchor rod 690. Further, the anchor handle fixed member 694 includes a longitudinal extending bore, off-set from a longitudinal axis of the anchor handle fixed member 694, that may be sized and configured to receive the release rod 688. The release rod 688 may be linearly fixed and selectively rotatable relative to the outer housing 692, extending through the anchor handle fixed member 694 and extending through the occluder handle portion 612. With this arrangement, the outer housing 692 and the anchor-release slider 696 may be fixed to each other. Further, the anchor fixed member 694 and the outer housing 692 may be fixed in the position depicted. However, once the anchor handle portion 614 is moved distally to the occluder handle portion 612 and the mode switch 664 is moved to an "anchors locked—float enabled" position, the release-enable switch 698 may be actuated or rotated, which allows each of the anchor-release slider 696, the outer housing 692 and the release rod 688 to be slidably movable relative to the anchor fixed member 694 as will be described in greater detail when discussing the releasing of the medical device hereafter.

With respect to FIG. 24C, an enlarged view of the anchor handle portion 614 taken from detail "24C" of FIG. 24 is shown, depicting the anchor handle portion 614 interconnected with the anchor tether wires (shown in dashed lines). The anchor tether wires may extend axially through the anchor rod 690 and through a portion of the anchor handle portion 614. Similar to the occluder tether wires, the anchor tether wires may include the first wire 640 and the second wire 642, the first wire 640 being a pull wire and the second wire 642 being a pin wire. The first wire 640 may be configured to extend out of the anchor rod 690 and between an outer surface of the anchor rod 690 and an inner surface of the anchor-release slider 696. The first wire 640 may further extend around the distal end of the anchor-release slider 696 and along an outer surface of the anchor-release slider 696. As depicted, there may be a descending groove along a longitudinal length of the outer surface of the anchor-release slider 696 for the first wire 640 to extend along. The descending groove may extend to a radial groove 706 formed in a proximal portion of the anchor-release slider 696. As such, the first wire 640 can extend to the radial groove 706 and be circumferentially wrapped around and secured within the groove 706. With respect to the second wire 642, such second wire 642 may extend axially from the anchor rod 690, through a bore 708 of the anchor-release slider 696, over a proximal end of the anchor-release slider 696, through a groove formed in a proximal portion of the anchor-release slider 696, and into the radial groove 706 formed in the proximal portion to be wrapped and secured within the radial groove 706 of the anchor-release slider 696. With this arrangement, upon releasing the medical device within an LAA (not shown in FIG. 24C), the anchor-release slider 696 may move proximally, thereby pulling the second wire 642 before pulling the first wire 640 due to the slack of the first wire being wrapped around the distal end of the anchor-release slider 696. Additional detail relating to release of the tether wires will be provided hereinbelow.

Now referring to FIGS. 25 and 25A the handle system 610 is shown depicting the anchor handle portion 614 moved distally forward to a second handle position as associated with an anchor-deployed position of a medical device 602. Note that FIG. 25 is the same cross-sectional view as FIG. 23, but in the second handle position. In the anchor-deployed position, the anchor handle portion 614 may move to abut the occluder handle portion 612. With such movement, the anchor rod 690 and the release rod 688 also move distally the same linear distance toward, and within, the occluder handle portion 612. Movement of the anchor rod 690 in a distal direction also moves the anchor tether 630 (FIG. 21C) forward a substantially similar distance to deploy the anchor portion 603 of the medical device 602 (see, e.g., FIG. 21A) due to being axially coupled together. Movement of the release rod 688 in the proximal direction positions an abutment edge 710 (FIG. 34B) of the release rod 688 through a release rod hole 712 (FIG. 34A) defined in the occluder-release slider 660 and adjacent the pawl 670 of the occluder-release slider 660.

Placing the mode switch 664 in the first position enables movement of the anchor handle portion 614, and thus movement of an anchor portion of a medical device. With the mode switch in the first position or "down position," as depicted in FIGS. 25 and 25A, the anchor handle portion 614 can move freely between the anchor-deployed position and the anchor-retracted position. Such control over deployment and retraction of the anchors, independent of other components, such as the occluder, is advantageous for a physician to obtain optimal placement and positioning of a medical device within the LAA.

With respect to FIGS. 26 and 26A, the handle system 610 is shown depicting the float handle portion 616 retracted proximally to a third handle position associated with a tether-deployed position for a medical device 602. In order to enable movement to the third handle position, the mode switch 664 has been moved from the first position (described above) to a second position or "upward position," as depicted in FIGS. 26 and 26A. Such upward movement changes the configuration of each of the key holes, or at least a portion of the key holes that respectively correspond with the release rod 688, the anchor rod 690 and the float road 650. Further, as previously set forth, each of the release rod 688, the anchor rod 690 and the float rod 650 include a key configuration along a selective portion of their respective lengths that can act as a key. These key portions will facilitate actuation, or prevent actuation, of each of the anchor handle portion 614, float handle portion 616 or actuation of the release-enable switch 698.

For example, with the mode switch 664 in the second position, actuation of the anchor handle portion 614 may be prevented by engagement with an anchor rod notch 714 (FIG. 24) defined in the anchor rod 690. For example, when the anchor handle portion 614 has been moved and the mode switch 664 is placed in the second position, the narrowed portion of the second key hole 684 engages the anchor rod notch 714 of the anchor rod 690 to, thereby, prevent the anchor handle portion 614 from further movement. Similarly, the float rod 650 may also define a float rod notch 716 (FIG. 23) corresponding with the third key hole 686 and configured to prevent movement of the float handle portion 616 until the anchor handle portion 614 is moved to the second handle position and the mode switch 664 is moved to its second position. Further, the release rod 688, with the mode switch 664 in the second position, is keyed to allow rotational movement, whereas in the first position the release rod 688 is keyed to prevent rotational movement. More specifically, the first key hole 682 includes a square-like or rectangular portion 718 that corresponds with the release rod 688 while the mode switch 664 is in the first position (see FIG. 25A) to prevent rotational movement. However, when the mode switch 664 is placed in the second position, the first key hole 682 includes a round portion 720 that corresponds with the release rod 688 to enable rotational movement. (also see FIG. 25A).

With the mode switch 664 in the second position, the float handle portion 616 may be retracted proximally and axially a defined distance. For example, the float handle portion 616 may be displaced until it is positioned against the occluder handle portion 612. With such proximal movement, the float rod 650 also moves proximally into a portion of the anchor handle portion 614. Further, movement of the float handle portion 616 proximally moves the catheter 622 proximally since the proximal end of the catheter 622 is fixed to the float handle portion 616. In this manner, the tethers, such as the occluder tethers 628 and the anchor tethers 630 maintain their axial position and are deployed from the catheter 622 (see FIG. 21B), thereby, limiting the resistance or biasing force placed on the implanted medical device by the still-attached delivery system. If desired, the tethers may be re-sheathed within the catheter 622 by simply moving the float handle portion 616 distally to its earlier position. Further, if desired, the anchor portion of the medical device may be retracted by simply moving the mode switch 664 back to the first position and then moving the anchor handle portion 614 proximally.

With reference to FIGS. 27-29, the handle system 610 is shown in a release position to release a medical device 602 from the delivery system 600. The release-enable switch 698 is moved to a release position, best shown in FIG. 27 (as compared to the non-released position shown in FIG. 22), which may be rotated about a release-enable switch pivot 722 in a clock-wise manner. In addition, release-enable switch 698 may define a radial opening 724 extending a distance in which the release-enable switch 698 travels to be placed in the release position. The fluid port 702 extends proximally through the radial opening 724 defined in the release-enable switch 698.

FIGS. 28 and 29 are cross-sectional views of the handle system 610 taken along section lines 28 and 29 of FIG. 27, respectively, depicting some of the components of the handle system 610 in the release position. It is noted that the outer housing 692 (FIG. 23) of the anchor handle portion 614 not shown for purposes of convenience and clarity. However, it is also noted that such outer housing, as previously set forth, is fixed to the anchor-release slider 696 and, therefore, the outer housing may move with the anchor-release slider 696 when moved to the release position.

In the release position, the release rod 688 is retracted proximally. In one embodiment, such retraction of the release rod 688 also moves the anchor-release slider 696 and the occluder-release slider 660 proximally, but leaves or maintains the anchor handle fixed member 694 against the occluder handle portion 612. Note that the pawl 670 of the occluder-release slider 660 is moved from the notch 668 of the inner extension member 652, thereby, enabling the occluder-release slider 660 to be moved by the release rod 688 to the released position, as will be shown and described in greater detail with respect FIGS. 34-35. In this manner, the occluder-release slider 660 and the anchor-release slider 696 can be moved proximally in a simultaneous arrangement.

As previously set forth, with respect to FIGS. 24B, 24C and 28, the first wire 640 and the second wire 642 of each of the occluder tethers 628 and the anchor tether 630 are fixed to the respective occluder-release slider 660 and the anchor-release slider 696. In particular, the first wires 640 of the occluder tethers 628 and anchor tether 630 may be wrapped distally and then proximally around a proximal portion of the respective occluder-release slider 660 and the anchor-release slider 696. Further, the second wires 642 of the occluder tethers 628 and the anchor tether 630 may extend proximally to the respective occluder-release slider 660 and anchor-release slider 696. In this manner, once the occluder-release slider 660 and the anchor-release slider 696 are retracted proximally, the distal end of the second wire 642 is displaced proximally before the distal end of the first wire 640 is displaced proximally due to a slack distance 726 provided by the proximal wrapping of the first wire 640. In other words, the first wire 640 is not moved proximally, along its length, until the slack distance 726 is overcome by the moved distance the occluder-release slider 660 and the anchor-release slider 696 has moved proximally. In this embodiment, the distance the sliders move to overcome the slack distance 726 is about twice the slack distance 726 for the respective occluder-release slider 660 and the anchor-release slider 696. With this arrangement, as depicted in FIG. 39, the second wire 642 may be pulled first as indicated by arrow 732, moving from a loop 728 formed by the first wire 640 that extends through an eyelet 730 of the medical device 602 and, once the slack distance 726 (FIGS. 24B and 24C) is overcome, the first wire 640 is pulled from the eyelet 730, thereby releasing the occluder tethers 628 and the anchor tether 630 from the medical device 602.

As depicted in FIGS. 26A and 28A, the mode switch 664 is in the second position or upward position. The second position of the mode switch 664 enables the release rod 688 to rotate within the round portion 720 of the first key hole 682, which movement of the mode switch 664 to the second position may be employed at anytime subsequent to deploying the anchor portion of the medical device 602. In other words, it is not necessary to employ the float feature by retracting the float handle portion 616 in order to move the mode switch 664 to the second position to enable rotation or actuation of the release-enable switch 698. In this manner, movement of the float handle portion 616 and/or movement of the release-enable switch 698 may be employed with the mode switch 664 in the second position or the upward position as depicted in FIGS. 26A and 28A.

Figure 31:
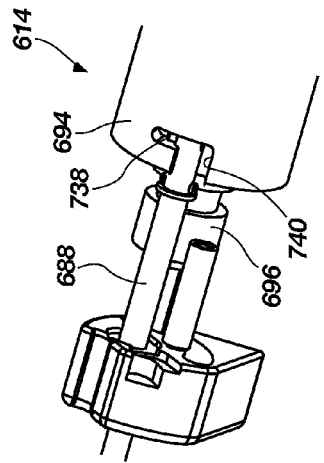
FIG. 31 is an enlarged perspective view of the proximal end portion of the handle system, depicting the handle system before the released position and without an outer housing of the handle system shown.
Figure 30:
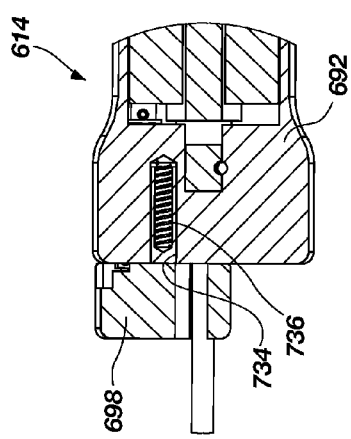
FIG. 30 is an enlarged cross-sectional side view of a proximal end portion of the handle system, taken along section line "30" of FIG. 22, depicting the end portion of the handle system before the released position.

Now referring to FIGS. 30-33, additional details relating to the release feature of the anchor handle portion 614 will now be discussed. It is noted that FIGS. 31-33 do not show the outer housing 692 of the anchor handle portion 614 for purposes of clarity in showing the various components and features of the anchor handle portion. FIG. 30 shows an enlarged cross-sectional proximal portion of the anchor handle portion 614, taken along section line "30" of FIG. 22, and depicts the release-enable switch 698 in a first position or non-released position. The outer housing 692 of the anchor handle portion 614 may define a cavity 734 therein. The cavity 734 may have a spring-loaded pin 736 positioned therein. While the release-enable switch 698 is in the first position, the spring-loaded pin 736 may be in a restrained position (i.e., as shown in FIG. 30). Further, while the release-enable switch 698 is in the first position, a release rod projection 738 of the release rod 688 is positioned in an elbow groove 740 defined in the anchor handle fixed member 694, as depicted in FIG. 31. In this manner, the anchor fixed member 694 may be operatively coupled or fixed to the anchor-release slider 696 and directly coupled to the release rod 688.

Figure 33:
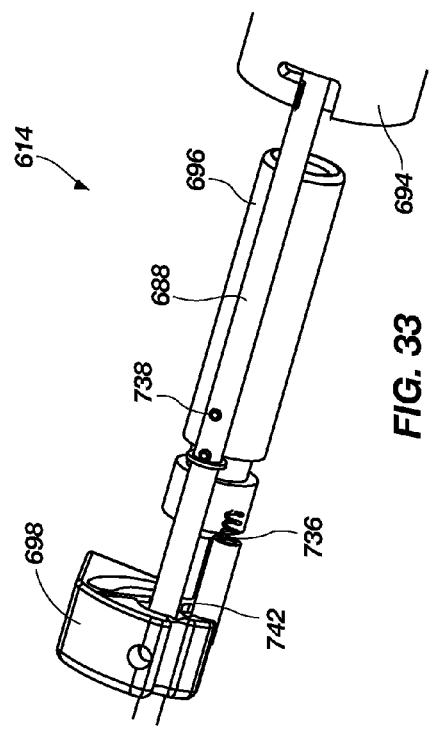
FIG. 33 is an enlarged perspective view of a proximal portion of anchor handle portion of the handle system, depicting the handle system in the released position and without an outer housing of the anchor handle portion shown.
Figure 32:
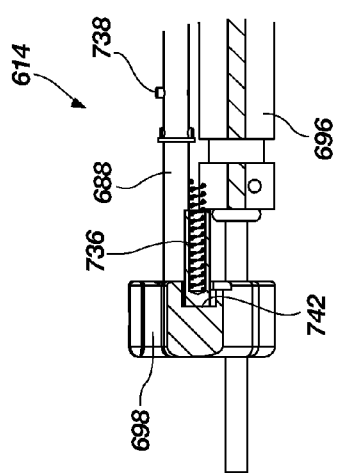
FIG. 32 is an enlarged cross-sectional side view of a proximal end portion of the handle system, taken along section line "32" of FIG. 27, depicting the handle system in the released position and without an outer housing of the handle system shown.

As depicted in FIGS. 32 and 33, once the release-enable switch 698 is rotated to the second position (the second position best shown in FIG. 27), the spring loaded pin 736 moves or springs to an exposed recess 742 defined in the release-enable switch 698, which may irreversibly fix the release-enable switch 698 in the second position. Also, when the release-enable switch 698 is rotated to the second position, the release rod 688 also rotates, thereby, rotating the release rod projection 738 extending from the release rod 688 out of a coupled position relative to the anchor fixed member 694. As depicted in FIG. 33, with the release rod projection 738 being positioned to enable linear movement, the release rod 688 and a portion of the anchor handle portion 614, namely, the anchor-release slider 696 and outer housing (not shown), may be linearly retracted in a proximal direction.

Figure 34B:
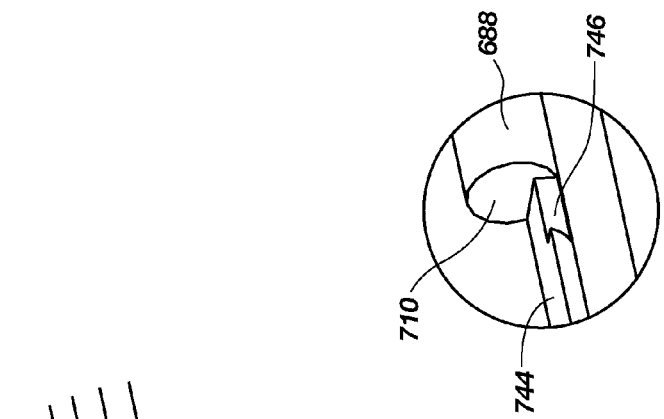
FIG. 34B is an enlarged perspective view of a portion of a release rod, taken from detail "34B" of FIG. 34.
Figure 34:
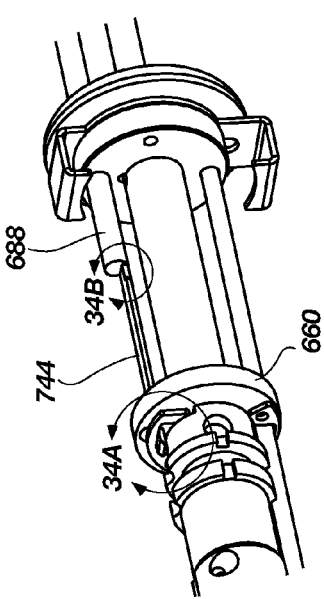
FIG. 34 is an enlarged perspective view of the occluder handle portion of the handle system (without showing the handle outer housing for purposes of clarity and convenience), depicting the occluder handle portion in the non-released position.
Figure 34A:
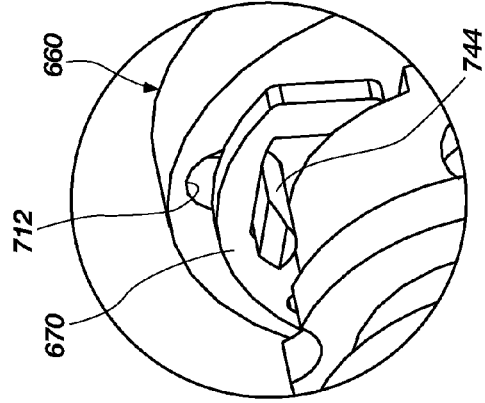
FIG. 34A is an enlarged perspective view of a portion of an occluder-release slider and release rod, taken from detail "34A" of FIG. 34.

Now referring to FIGS. 34, 34A, 34B and 35, additional description will now be provided for the release rod 688 employing movement of the occluder-release slider 660. Again, the outer housing of the occluder handle portion is not shown for purposes of clarity. With reference to FIGS. 34, 34A and 34B, the release rod 688 is configured to act as a key defining multiple structural features that assist in controlling the functionality of the handle system 610. For example, the release rod 688 may have an elongated narrow portion 744 defined on a distal portion of the release rod 688 that is sized and configured to slide or linearly move under the pawl 670 of the occluder-release slider 660. The elongated narrow portion 744 may be formed by removing, for example, about one-half to two thirds of an upper elongated portion of the release rod 688 so that when the release rod 688 is oriented in a first position, as depicted, the elongated narrow portion 744 is oriented so as to easily slide under the pawl 670 when moved distally. The proximal end of the elongated narrow portion 744 may include a release rod notch 746 defined therein, as best depicted in FIG. 34B. The release rod notch 746 may be sized and configured to catch or couple to the occluder-release slider 660 so that the release rod 688 can retract the occluder-release slider 660.

Figure 35:
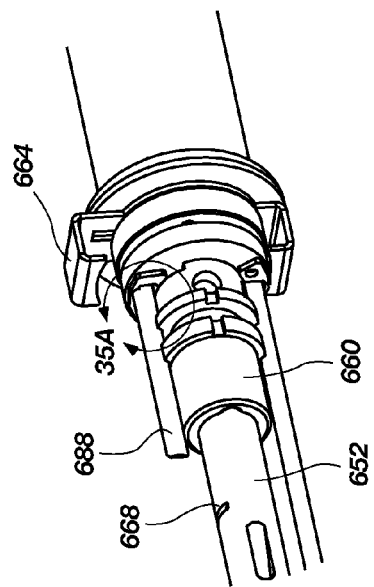
FIG. 35 is an enlarged perspective view of the occluder-release slider and release rod (without showing the handle outer housing for purposes of clarity and convenience), depicting the occluder-release slider and release rod in the released position.
Figure 35A:
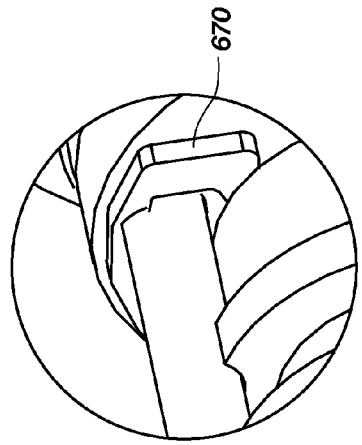
FIG. 35A is an enlarged perspective view of a release rod and a pawl of the occluder-release slider, taken from detail "35A" of FIG. 35, according to an embodiment of the present invention.

As depicted in FIGS. 35 and 35A, the mode switch 664 is moved to the second position or upward position. As previously set forth, the second position of the mode switch 664 allows rotational movement of the release rod 688. As shown in FIGS. 35 and 35A, the release rod 688 is in a rotated position. However, before such rotation of the release rod 688 and movement of the mode switch 664 to the second position, the release rod 688 is moved forward to deploy the anchor portion of the medical device 602. In the rotated position, the release rod 688, via the release rod notch 746 (FIG. 34B) in the release rod 688, can catch the occluder-release slider 660. Further, in the rotated position, the pawl 670 is moved upward via such rotation, the pawl 670 moving out of engagement with the notch 668 defined in the inner extension 652 of the occluder handle portion 612, thereby, decoupling the occluder-release slider 660 from the inner extension 652. The proximal movement of the release rod 688 can then proximally retract the occluder-release slider 660 such that it is adjacent the mode switch 664. As previously set forth, such proximal movement of the release rod 688 simultaneously retracts the occluder-release slider 660 and the anchor-release slider 696 (not shown in FIGS. 35 and 35A) for substantially simultaneously detaching the occluder tethers and the anchor tether from the medical device.

Referring now to FIGS. 36-40, a cross-sectional view of a medical device 602 coupled with a medical delivery device (e.g., delivery device 600 in FIG. 21) is shown in accordance with another embodiment of the present invention. The medical device 602 includes an occluder portion 605 and an anchor portion 603. The medical device 602 depicted herein is similar to the medical device depicted in FIGS. 9A and 9B, with three anchor segments having six anchor loops 748 (two anchor loops 748 per anchor segment) and six occluder frame segments 750 each positioned and oriented around a hub 752 in an alternating fashion. For simplistic purposes, the cross-sectional views in FIGS. 36-40 depict the anchor loops 748 and occluder frame segments 750 as being rotated into the same plane, though in this embodiment they may be oriented around the hub 752 in the alternating arrangement set forth in the above-noted embodiment.

Description of the various positions of the medical device 602, relative to the medical device delivery system, will now be set forth. Before introducing the medical device 602 to the LAA (not shown in FIGS. 36-40) the sheath 604 may first be introduced to the LAA. As known by one of ordinary skill in the art, the sheath may be introduced into the vasculature extending toward and into the right atrium of the heart. For example, access into the right atrium may be gained through the femoral vein. The sheath 604 may then be introduced into the left atrium, via a trans-septal puncture, and then positioned within an LAA, preferably, in this embodiment, positioning a distal end of the sheath at a rear location relatively deep within the LAA, located and positioned through conventional procedures and imaging techniques.

Once the sheath 604 is positioned in the LAA, the medical device 602 may be pushed through the sheath 604, beginning at the proximal end of the sheath 604, toward the LAA, as depicted in FIG. 36. The medical device 602 may be introduced into the sheath 604 via a loader 754 (see FIG. 21) positioned around the catheter 622. The loader 754 may be moved to a distal end 758 of the catheter 622 against the deployed occluder portion 605 and pulled within the loader 754. The end of the loader 754 may then be inserted into the proximal end of the sheath 604 so that the catheter 622 can be manually advanced through the sheath 604 thereby, advancing the medical device 602 to a distal portion of the sheath 604 and into the LAA. As depicted, having been advanced by the catheter 622 toward the distal end of the sheath 604, the anchor portion 603 of the medical device 602 is retracted within a distal portion 756 of the catheter 622 with the occluder portion 605 positioned distally relative to a distal end 758 of the catheter 622. Once the medical device 602 is positioned at a distal portion of the sheath 604 within the LAA, the occluder portion 605 may then be deployed by manually retracting the sheath 604, as depicted by arrow 760, which facilitates deployment of the occluder portion 605 of the medical device 602.

As depicted in FIG. 37, the sheath 604 is in a retracted position with the occluder portion 603 in a deployed position. Such occluder portion 605 may automatically deploy by retracting the sheath 604 due to the self expanding characteristics of the occluder frame segments 750. The occluder portion 605, in this embodiment, may not have any anchoring function, but rather, as previously described, includes a tissue growth promoting member 762 with one or more layers that provide a soft and supple occluder portion 605. Through imaging techniques, a physician can slowly pull the occluder portion 605 of the medical device 602 from a rear position within the LAA toward a desired position, stopping and analyzing multiple different positions and orientations within the LAA until determining an optimal or preferred position, for example, adjacent to the ostium and within the LAA. If the physician at any time believes that the occluder portion 605 has been pulled beyond the optimum location in the LAA or from the LAA, the physician can readily re-capture the occluder portion 605 by simply moving the sheath 604 distally. The sheath 604 can then be advanced again deep within the LAA and the occluder portion 605 re-deployed and then retracted to an optimal position for the occluder portion 605 to be positioned. Once the optimal position is located in the LAA, the physician may deploy the anchor portion 603 of the medical device 602 by moving the anchor handle portion 614 in a distal direction to the second handle position (see FIG. 21). Such movement of the anchor handle portion 614 to the second handle position moves the anchor pusher 632 distally, as indicated by arrow 764, to, thereby, move the anchor portion 603 of the medical device 602 distally from a retracted position to a deployed or expanded position (FIG. 38) Likewise, the anchor portion 603 can be moved back from the deployed position to the retracted position.

As shown in FIG. 37 and described in detail in previous embodiments, the anchor portion 603 may include multiple anchor loops 748, each including a first end 749 and a second end 751. The first end 749 of each anchor loop 748 being coupled to the hub 752 and each second end 751 being coupled together to form the anchor hub. When the anchor portion 603 is in the retracted position, the first end 749 and second end 751 of each anchor loop 748 may be proximal to a distal end of the occluder portion 605. Further, the second ends 751 of the anchor portion 603 may be proximal to the hub 752. Also, when the anchors are in the retracted position, the distal end of the anchor portion 603, e.g., the distal end of anchor loops 748, are proximal to the distal end of the occluder portion 605. With this arrangement, the anchor portion 603 may independently move between the retracted position and the deployed position when the occluder portion 605 is deployed, thereby, providing the physician the ability to selectively anchor the occluder portion 605 at a preferred location and orientation within the LAA.

As depicted in FIG. 38, the anchor pusher 632 is moved to the distal end 758 of the catheter 622 to, thereby, deploy and move the anchor portion 603 of the medical device 602 from the retracted position to the deployed position. In the deployed position, the first end 749 and second end 751 of each of the anchor loops 748 remain proximal to the distal end of the occluder portion 605 with a portion of the anchor loops 748 extending distal to the distal end of the occluder portion 605.

As previously described with respect to the other embodiments, the anchor loops 748 or a portion of the anchor portion 603 may roll-out through the hub 752, having been pushed by the anchor pusher 632, in an everting type arrangement. In this manner, the anchor portion 603 can be moved between the retracted position and the deployed position, as depicted in respective FIGS. 37 and 38, with an intermediate portion of the anchor portion 603 being moveable or displaceable through a bore of the hub 752. In one embodiment, the anchor portion 603 can roll-inward to the retracted position and roll-outward to the deployed position. In another embodiment, the anchor portion 603 can be moved to a retracted position by at least partially inverting the anchor portion 603 through the hub 752. In another embodiment, the anchor portion can be moved to a deployed position by at least partially everting the anchor portion 603 through the hub 752.

Referring to FIG. 38, the anchor portion 603 may include multiple anchor loop portions, such as six anchor loops 748 in this embodiment, with engaging members 766 sized and configured to engage tissue in the LAA. In this embodiment, the anchor loops 748 may include an anchor contact portion 768 proximal to the most proximal engaging member 766 of a given anchor loop 748. The anchor contact portion 768 includes an outer surface of the anchor loop 748 that may abut against an underside portion 770 of the occluder portion 605. The underside portion 770 of the occluder portion 605 may include a ribbon portion 772 of the tissue growth member 762, which may be more firm and unyielding (having less elasticity) than other portions of the tissue growth member 762. The ribbon portion 772 may be sewn to the occluder portion 605 and/or adhesively attached. Further, the ribbon portion 772 may be generally circular in shape to cover the underside of the distal end of the occluder portion 605. The ribbon portion 772 may be formed of, for example, a biocompatible woven fabric, or any other suitable material that also will promote tissue in-growth and provide a more firm and unyielding surface area than the other portions of the tissue growth member 762. Also, it is noted that although FIG. 38 depicts the occluder portion 605 and anchor portion 603 in their fully expanded positions, such that the anchor portion may be pre-loaded (or slightly constrained) to provide force against the ribbon portion 772 of the occluder portion 605. Further, such anchor and occluder portions 603 and 605 may be somewhat compressed within the LAA such that the anchor portion 603 and occluder portion 605 may provide a radially outward force against the tissue of the LAA. As such, as the anchor portion 603 is deployed, the anchor contact portion 768 of the anchor loops 748 may be configured to bias and push outward against the ribbon portion 772 or underside portion 770 of the occluder portion 605 so that the occluder portion 605 is pushed against the tissue with the engaging members 766 engaging tissue distal the occluder portion 605 in the LAA.

In one embodiment, when the anchor portion 603 is in the deployed position (FIG. 38), the engaging members 766 may be oriented to extend proximally and, when the anchor portion 603 is in the retracted position the engaging members 766 may be oriented to extend distally (FIG. 37). The change in orientation of the engaging members 766 may occur, in one embodiment, due to inverting and everting the anchor portion 603 when moving the anchor portion between the retracted position and the deployed position. For example, when the anchor portion is moved from the deployed position to the retracted position, an outer surface of the anchor loops 748 adjacent the engaging members may be rolled-inward or inverted such that the outer surface is moved to become an inner surface of the anchor loops 748.

Figure 45:
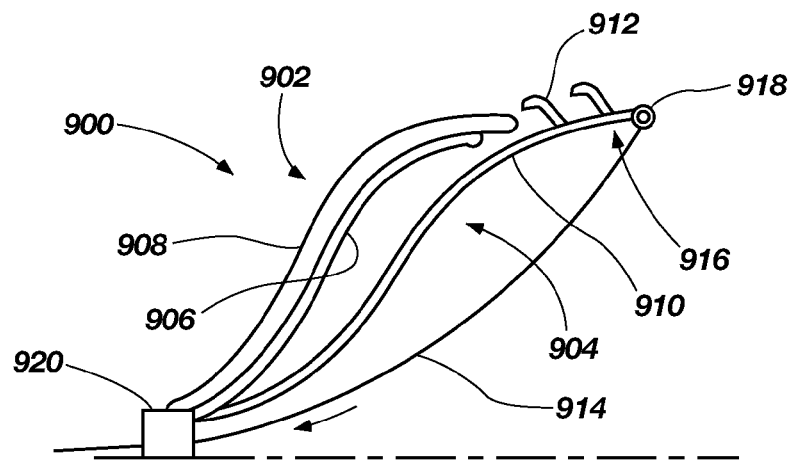
FIG. 45 is a partial cross-sectional view of a medical device according to another embodiment of the present invention.
Figure 46:
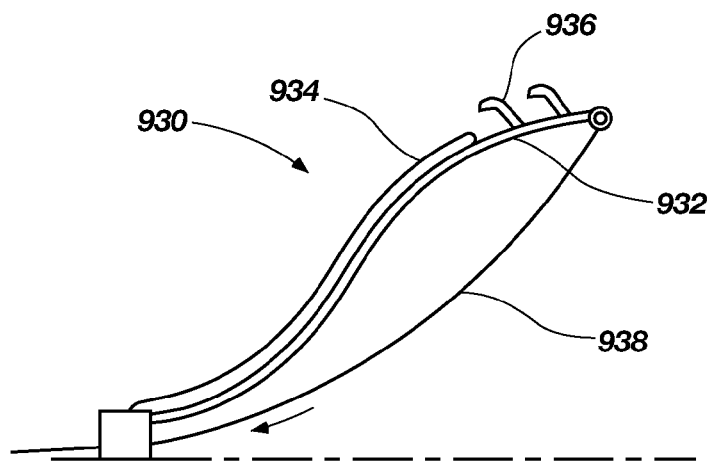
FIG. 46 is a partial cross-sectional view of a medical device according to yet another embodiment of the present invention.
Figure 47:
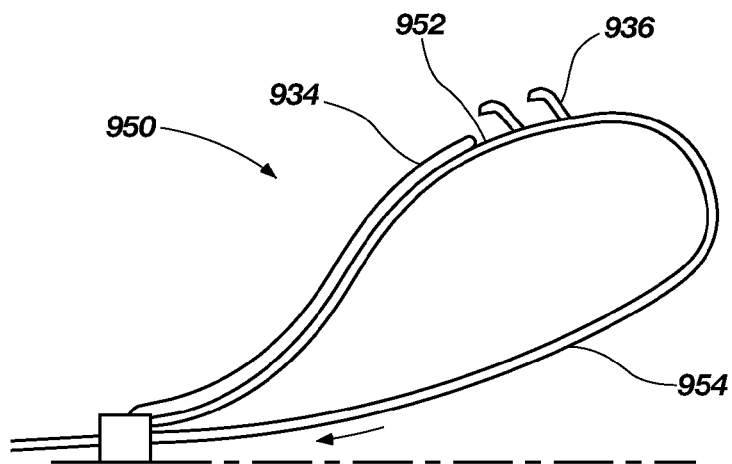
FIG. 47 is a partial cross-sectional view of a medical device according to yet a further embodiment of the present invention.

In other embodiments, the position of the engaging members 766 may change by moving the engaging members between a tissue-engaging position and a tissue-non engaging position such that the engaging members 766 are moved away from the tissue surface to, thereby, allow positioning or repositioning of the occluder portion 605. Such may be employed with an extension portion, which may be defined as the portion of the anchor loops 748 extending inwardly and proximally from adjacent the engaging members 766 and configured to be pulled proximally to move the engaging members 766 from the tissue-engaging position to the tissue-nonengaging position while the occluder portion 605 remains in a deployed position. Other embodiments including an extension portion or extension member as a portion of the anchor portion extending inwardly and proximally of the engaging members of the medical device are depicted in FIGS. 45-47.

In another embodiment, an anchor hub 774 may include a second tissue growth member 776 formed as a sock-like structure. Such a sock-like structure was previously described with respect to an embodiment shown in FIG. 19. The sock like structure effectively provides a covering at the proximal end of the anchor hub 774 and hub 752 to promote tissue growth and to assist in preventing emboli from migrating from the hub 752. The second tissue growth member 776 may be pulled over the proximal end of the anchor hub 774 and maintained at that position with a spring 778, the spring being held within a notch (not shown) in the anchor hub 774. The second tissue growth member 776 can be formed of similar materials as the tissue growth member 762 of the occluder portion 605 such as, for example, polyurethane foam and/or ePTFE.

In another embodiment, the hub 752 may include multiple guides 780 extending longitudinally within an inner surface of the hub 752. The guides 780 may be sized and configured in a spaced arrangement so that, as the anchor hub 774 is moved between an anchor-retracted position and an anchor-deployed position the anchor loops 748 may be relatively aligned and substantially maintained from snagging each other or otherwise becoming tangled and intertwined. The guides 780, in one embodiment, may include elongated nubs each extending longitudinally between a proximal opening and a distal opening of the hub. In another embodiment, one or more nubs (not shown) extending along the anchor loops 748 may be employed as a guide to properly align the anchor loops 748 as they are displaced through the hub 752. Further, in another embodiment, a loop arrangement (not shown) may be utilized as a guide to allow the anchor loops 748 to slide through the loop arrangement for proper alignment when moving through the hub 752. In another embodiment, the anchor loops 748 are individually configured to maintain a generally planar configuration or a substantially flat configuration such that the anchor loops 748 may be configured to resist movement out of plane of the generally planar configuration. Such resistance from movement out of plane also may assist in proper alignment of the anchor loops 748 moving through the hub 752.

As in previous embodiments, the anchor loops 748 may include a coiled wire 782 or other member. The coiled wire 782 may include a wire wrapped around a portion of the anchor loops 748 in a coil configuration. Such a coiled wire 782 may provide additional traction with tissue in the LAA as well as provide additional surface area contact with tissue in the LAA and promote tissue growth thereto. Further, the coiled wire 782 provides a safety mechanism in the event an anchor loop 748 fractures from the anchor loop undergoing unpredictable stress/strain between the retracted and deployed configurations. Such a coiled wire 782 can substantially contain any fracture of a given anchor loop 748 within the coiled wire 782 itself. In an embodiment that includes the coiled wire 782, the engaging members 766 may extend a longer length for proper clearance beyond the coiled wire 782 as previously discussed. As in previous embodiments, the engaging members 766 extend at an angle and with a blunt peak so as to substantially inhibit puncturing or piercing of the tissue, though they may be configured to aggressively engage tissue when the medical device 602 is deployed and moved or tugged proximally or toward the ostium of the LAA to substantially prevent migration therefrom.

As previously noted, the medical device 602 may be coupled to the handle system 610 (FIG. 21) via the occluder tethers 628 and the anchor tether 630 (see FIG. 21C). The occluder tethers 628 and the anchor tethers 630 may be coupled to the eyelets 730 of the medical device 602 with tether wires (shown as dashed line), the tether wires being the direct interconnection to the medical device 602.

The catheter system 608, as previously described and set forth with respect to FIG. 21C, may extend through the sheath 604, as depicted in FIGS. 38 and 38A. The catheter system 608, as previously described, may include the catheter 622 with the central lumen 624 and peripheral lumens 626 configured to house the respective anchor tether 630 and the occluder tethers 628, the anchor tethers 630 including the anchor pusher 632 and the occluder tethers 628 including occluder pushers 636. The anchor pusher 632 or anchor coil may be configured so as to exhibit sufficient axial compressive strength to push the anchor portion 603 from the anchor-retracted position (see FIG. 37) to the anchor-deployed position. The catheter 622 and the occluder pushers 636 may be configured to provide axial strength or compressive strength to push the medical device 602 through the sheath 604. The occluder pushers 636 may provide axial strength or compressive strength when deploying the occluder tethers 628 from the catheter 622 or, otherwise, employing the float feature. As previously set forth, each of the occluder tethers 628 and the anchor tether 630 may include tether wires (shown as dashed lines in FIG. 38 and as the first wire 640 and second wire 642 in FIG. 38A) that are directly connected to the medical device 602. The tether wires may be configured to facilitate pulling or retracting of the medical device 602 and are in tension when employed for such retraction. For example, when pulling the occluder portion 605 into the loader 754 (FIG. 21) or into the sheath 604, the tether wires for the occluder tether 628 maintain the position of the medical device 602 while the loader 754 or the sheath 604 are displaced relative to the medical device 602 to enable the medical device 602 to become constrained within the sheath 604. Similarly, the tether wires for the anchor tether 630 are configured to pull the anchor portion 603 from the anchor-deployed position to the anchor-retracted position (FIG. 37), within the catheter 622, as depicted with arrow 784.

Referring briefly to FIG. 39, a cross-sectional view of one eyelet 730 of the medical device 602 is shown, to which a tether may be connected. As depicted, the tether (which may be the occluder tether 628 or the anchor tether 630) may only be coupled to the medical device via the tether wires. The tether wires may include a first wire 640 and a second wire 642. In one embodiment, the first wire 640 may be stainless steel and the second wire 642 may be Nitinol, however, other suitable biocompatible materials for the wires may be employed. The first wire 640 may be utilized as a pull wire and the second wire 642 may be utilized as a pin wire. The first wire 640 may be folded over at a mid portion, the mid portion defining a loop 728 that extends through the eyelet 730. The second wire 642 may be positioned to extend through the loop 728 depicted as being under the eyelet 730. The first wire 640 may then be cinched somewhat tight to thereby couple the first wire 640 and the second wire 642 to the medical device 602. Release of the tether wires from the medical device 602 may be employed by first pulling on the second wire 642, as indicated by arrow 732, until the second wire has retracted through the loop 728 of the first wire 640, after which, the first wire 640 may then be pulled from the eyelet 730, thereby, disconnecting the tether wires from the medical device 602. Additional description of releasing the medical device by pulling the second wire 642 before the first wire 640 is set forth above with respect to FIGS. 24B and 24C.

Figure 40:
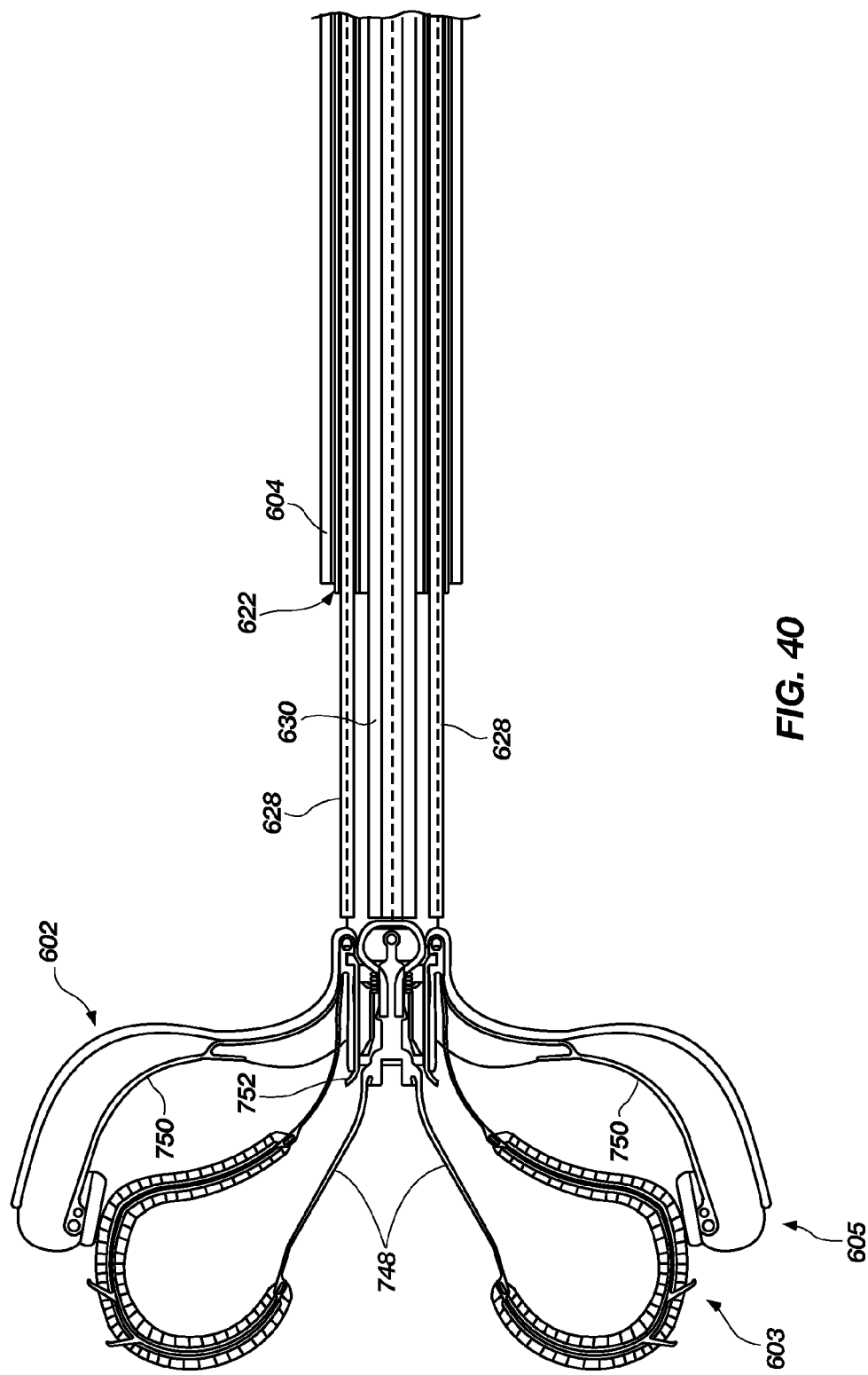
FIG. 40 is an enlarged cross-sectional view of the medical device and tethers deployed from the catheter system, according to an embodiment of the present invention.

With reference now to FIG. 40, the medical device 602 is shown with the catheter 622 (and the sheath 604) retracted to expose and deploy distal portions of the occluder tethers 628 and the anchor tether 630, previously set forth as the float feature and enabled by moving the float handle portion 616 to the third handle position of the handle system (see FIGS. 21 and 21B). This float feature may be employed to enable a physician to assess the position and stability of the medical device 602 in the LAA without placing unnecessary torque or lateral forces on the medical device 602 and potentially damaging the tissue in the LAA. For example, once the anchor portion 603 is deployed, the physician may retract the catheter 622 from the medical device 602 while maintaining interconnection to the medical device 602 via the tethers 628, 630. The physician can then observe the medical device in a position that is closer to that which will occur when the device is released and can also conduct a push/pull test on the medical device 602 and view, through imaging techniques, the tethers 628, 630 bowing and the medical device 602 slightly contorting. If the medical device 602 is dislodged from the LAA, the device may easily be recaptured by advancing the catheter 622, retracting the anchor portion 603 and advancing the sheath 604 over the occluder portion 605 by employing the previously described handle system functions. The medical device 602 can then readily be re-positioned and anchored following the steps previously set forth. If the physician finds the device 602 is properly seated in the LAA after conducting a push/pull test, the physician can then release the tether wires from the medical device 602, as described herein.

As previously discussed, the frame segments of the medical device 602 may include tapers or changes in cross-section to provide desired structural characteristics and performance. For example, as seen in FIG. 38, the width of the anchor loops 748 may taper along their lengths. It is noted that the width is indicated as "W" in various drawing figures herein and may also be referred to as a radial width due to its dimension having a radial directional component. In the embodiment shown in FIG. 38, the anchor loops exhibit a relatively thick width at their radially inner ends or second end 751 and taper to a thinner width as they extend to the curved portion (i.e., near the location where the coils 768 terminate at a radially inner position), such as at the second wire-connect portion 380 (FIG. 11A). In one embodiment, this taper may be gradual from a width of approximately 0.015 inch to a width of approximately 0.008 inch. Extending past the second wire-connect portion, the anchor loop 748 may step up its width again at this location and then vary its width throughout the curved portion of the loop 748 (i.e., throughout the length to which the coil 768 is attached). In one example, the smallest width throughout the curved portion may be approximately 0.003 inch at a location approximately midway through the length of the curved portion. The anchor loop 748 may then taper back to a thicker width as extends back toward the hub from its thinnest section. In such an embodiment, the depth of the anchor loop (i.e., the dimension measured into the plane of the page) may remain constant. It is noted that the depth is indicated as "D" in various drawing figures included herein and is also referred to as a circumferential depth due to its dimension in a generally circumferential direction about the medical device. In one embodiment, for example, the depth may be approximately 0.017 inch. In other words, if the anchor loop 748 is cut from a sheet of material (e.g., Nitinol), the sheet of material may be 0.017 inch thick in this example embodiment.

Further, for example, the occluder frame segments 750 may also include at least one taper along a portion of the length thereof. In one embodiment, the width may taper from the proximal end coupled to the hub toward the distal end along at least a portion of the occluder frame segment. By tapering portions of the frame segments of the occluder portion 605 and the anchor portion 603 minimize predictable and unpredictable stresses that may be placed on such frame segments, thereby, limiting potential for fractures in the frame segments. Of course, as known by one of ordinary skill in the art, the above-noted dimensions may vary slightly, for example within acceptable tolerances, through the electro-polishing processes conducted on the frame segments. Such electro-polishing of the frame segments further minimizes potential fractures in the frame segments.

It is also noted that the anchor loops 748 may be defined to exhibit desired aspect ratios (i.e., depth (measured into the page in FIG. 40) vs. width (measured substantially transversely to depth). In one embodiment, the anchor loops 748 may include a portion that exhibits a depth-to-width aspect ratio of at least approximately 2:1. In another embodiment, the anchor loops 748 may include portions that exhibit a depth-to-width aspect ratio of between approximately 1.1:1 and approximately 5.7 to one. However, in other embodiments, the anchor loops 748 may include portions having depth-to-width aspect ratios between approximately 1:1 and approximately 12:1. Further, the depth-to-width aspect ratio for the occluder frame segments 750 along a portion of the length thereof may be at least approximately 2:1, but may include a range of between approximately 1:1 and approximately 4:1 along the length of the occluder frame segments 750. In one embodiment, the aspect ratio for the occluder frame segments 750 may range between 1:1 and 12:1 along the length of the occluder frame segments 750.

In another embodiment, the medical device 602 may include different sizing options, such as a small size, a medium size and large size. Such sizing options may primarily be measured by way of the anchor portion 603, in a fully expanded state, and attached to the hub 752. For example, each anchor frame segment of the anchor portion 603 may include a length and a height, the length being the distance from the proximal end of the hub to the distal most end of the anchor loops 748 and the height being the lateral distance, relative and perpendicular to the length, between the anchor loops at, for example, where the anchor loops contact the occluder portion 605. The height of the anchor portion 603 for the different sizing options may include, for example, 21 mm, 28 mm and 35 mm for the small, medium and large sizes, respectively. The length of the anchor portion 603 for the different sizing options may include 18 mm, 22 mm and 25 mm for the small, medium and large sizes, respectively. Of course, these sizing options may vary and the present invention is not limited to such sizing options.

Figure 41:
FIG. 41 is a partial perspective view of an articulating catheter, depicting a distal portion of the catheter, according to an embodiment of the present invention.
Figure 41A:
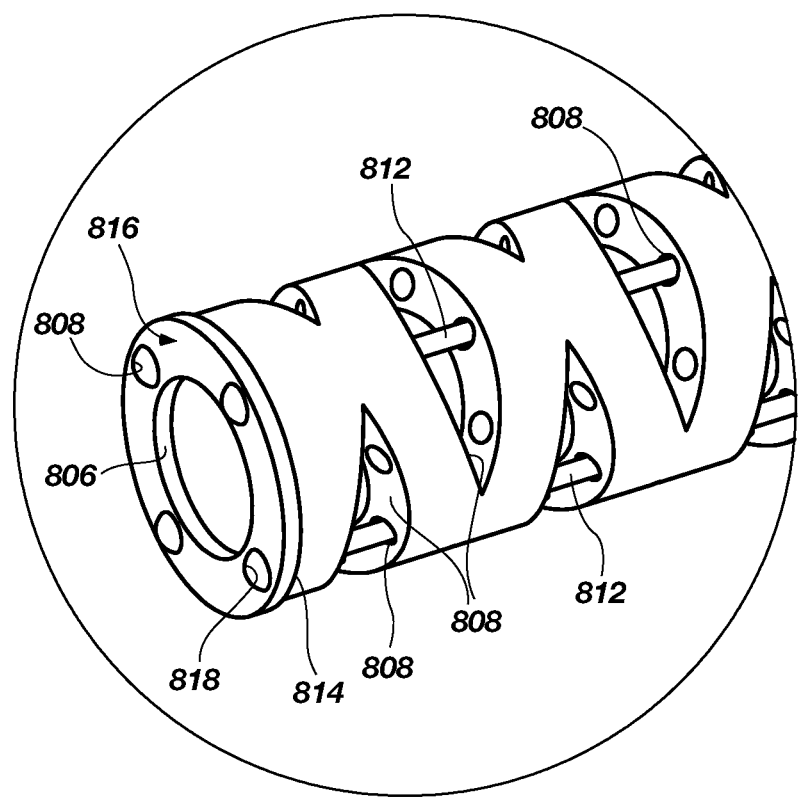
FIG. 41A is an enlarged perspective view of the distal portion of the articulating catheter, taken from section 41A of FIG. 41, according to an embodiment of the present invention.

Referring now to FIGS. 41 and 41A, a distal portion 804 of a catheter 802 configured to articulate at the distal portion 804 thereof is shown. Such a catheter 802 may be the catheter described in the above embodiment, but also may be the sheath described above. The catheter 802 may define a central lumen 806 and multiple peripheral lumens 808, such as four peripheral lumens, each extending along a longitudinal length of the catheter 802. Further, within the distal portion 804 of the catheter 802, the catheter 802 may define slots 810 or notches extending laterally therethrough between an outer surface and an inner surface of the catheter 802. Such slots 810 may be defined in columns, such as four columns, along the distal portion 804 of the catheter 802 with two sets of opposing slots 810 in a staggered configuration such that adjacent columns of slots 810 are staggered relative to each other. The slots 810 can define a slit-like configuration being wider in the middle and narrower at the opposing ends of the slots. A variety of slot configurations may be employed, such as crescent shape, v-shaped, helical shaped or any other suitable shaped slot. With this arrangement, the slots 810 facilitate loosening the transverse strength of the distal portion 804 of catheter 802 to allow greater flexibility therein while substantially maintaining the axial strength of the distal portion 804 of the catheter 802.

Further, the catheter 802 may include wires 812 or other structural members extending through the peripheral lumens 808 of the catheter 802. Such wires 812 may be fixed to a distal end 814 of the catheter 802 by, for example, securing the wires 812 to a plate 816. The plate 816 may also include openings 818 corresponding with the peripheral lumens 808 through which ends of the wires 812 may be secured. The plate 816 may be secured to the distal end 814 of the catheter 802 by way of tension applied to the plate by the wires 812, or by other, independent means including, for example, adhesive. The central lumen 806 of the catheter 802 may be utilized for delivering a medical device for permanent or short term placement, or for any other suitable purpose, such as introducing a substance, retrieving a device or unwanted substance from the vasculature, providing passage for another catheter, or any other suitable purpose where an articulating catheter may be employed.

Referring to FIGS. 42 and 42A, the catheter 802 may be coupled to an articulating handle system 830. The handle system 830 may include an articulating handle member 832, such as a universal joint or any other suitable articulating member, positioned between a distal handle portion 834 and a proximal handle portion 836. Each of the distal handle portion 834 and the proximal handle portion 836 may define a first bore 838 and a second bore 840, respectively, axially extending through their respective portions and configured to be axially aligned relative to each other. The catheter 802 may axially extend through the handle 830, namely, the first bore 838 of the distal handle portion 834 and through at least a portion of the second bore 840 of the proximal handle portion 836 in a fixed relationship therewith. Further, between the distal handle portion 834 and the proximal handle portion 836, the handle system 830 may include a flexure member 842 positioned within or adjacent the articulating handle member 832.

Figure 43:
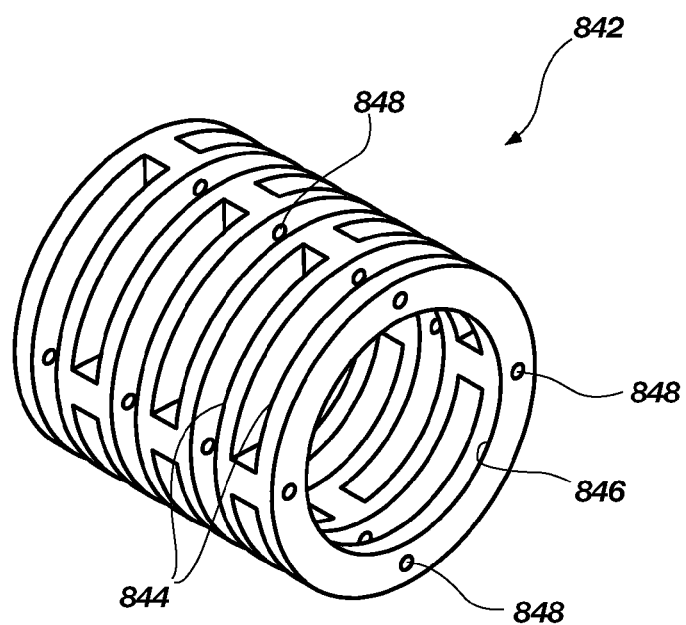
FIG. 43 is a perspective view of a flexure member, according to an embodiment of the present invention.

As shown in FIGS. 42A and 43, the flexure member 842 may include a tubular configuration with multiple spaced channels 844 defined laterally through a periphery of the tubular configuration. The flexure member 842 may be a resilient member sized and configured to bend or contort as the articulating handle member 832 is manually articulated. The flexure member 842 may include a central opening 846 extending through the flexure member 842 with peripheral openings 848 extending along the periphery of the flexure member 842 and corresponding with, or extending substantially parallel to, an axis of the central opening 846. Such peripheral openings 848 may be sized and configured to support and guide the wires 812 therethrough and the central opening 846 may be sized and configured to be positioned over the catheter 802 that extends therethrough.

With respect to FIG. 42A, the catheter 802 may define openings 850, at a proximal portion of the catheter 802 within the distal handle portion 834, through which the wires 812 may extend. Further, first tubing 852, with a lumen defined therethrough, extends outwardly and proximally from the openings 850 and through the distal handle portion 834 and is configured such that the wires 812 extend through the lumens of the first tubing 852. For example, the four wires 812 may extend through the catheter 802 through the four openings 850 and through the corresponding first tubing 852, one wire 812 extending through each opening 850 and a corresponding first tubing 852. The openings 850 may be defined in the catheter 802 at positions opposite another opening such that each adjacent opening may be radially positioned approximately ninety degrees from the other opening. Of course, if there are more or less wires and corresponding openings than the above example of four wires and four openings, such openings may be equally spaced about the catheter at other angular frequencies.

Further, as previously set forth, the wires 812 may be channeled from the openings 850 to extend outwardly and proximally through the first tubing 852 to a larger spaced relationship as compared to the spacing of the wires 812 within the catheter 802. The wires 812 continue to extend proximally, through the peripheral openings 848 (FIG. 43) of the flexure member 842 and through the proximal handle portion 836. Within the proximal handle portion 836, each wire 812 may extend through at least one second tubing 854.

Figure 44:
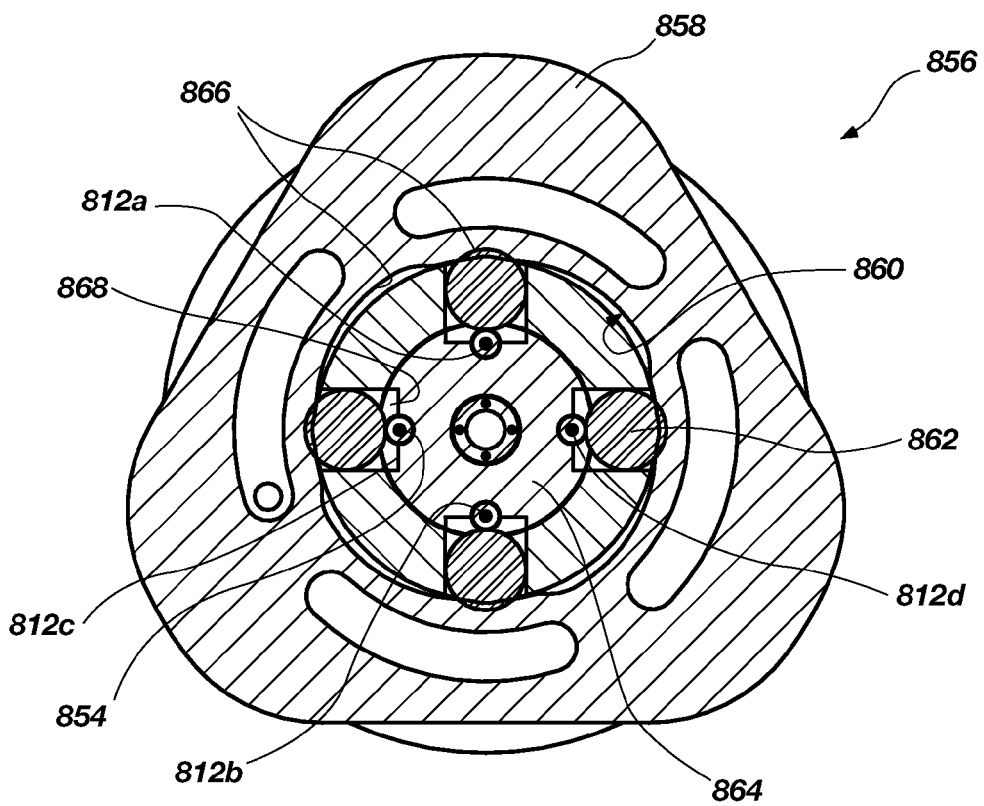
FIG. 44 is a cross-sectional view of a wire engaging member, taken from line 44 of FIG. 42, according to an embodiment of the present invention.

Referring to FIGS. 42A and 44, the proximal handle portion 836 may also include a wire engaging member 856. The wire engaging member 856 may include a rotatable knob 858, a ramped surface—referred to herein as a ramp 860 —, multiple spheres 862 and an inner member 864. The ramp 860 may be an inner surface of the knob 858 and may include a detent surface 866 defined therein exhibiting various sloping, recessed portions extending radially within the ramp 860 that are sized and configured to correspond with and move the spheres 862 in a tightened or clamping relationship with the wires 812. Further, the inner member 864 may include a recess 868 through which the wires 812 extend, the recess 868 also being positioned and configured to receive a portion of the spheres 862. With this arrangement, the detent surface 866 corresponds with the spheres 862 such that, when rotating the knob 858, the detent surface 866 rolls over the spheres 862 and is configured to clamp the wires against the inner member 864. In this manner, the wires 812 may become placed in a fixed relationship with the proximal handle portion 836. When the knob 858 is rotated to a disengaged position, the wires 812 may be loosened within the second tubing 854 and be fixed only at the distal portion 804 of the catheter 802. Further, as previously set forth, the wires 812 are channeled to extend in a spaced relationship through the handle system 830 and, in particular, through the flexure member 842. The increased radially spaced relationship of the wires 812 facilitates a wider travel for the wires 812 to articulate the distal portion 804 of the catheter 802 than if the wires 812 exhibited spacing similar to the spaced distance of the wires 812 within the catheter 802.

More specifically, for example, with respect to FIGS. 41 and 42A, if the distal handle portion 834 is articulated downward, via the articulating handle member 832, the upper wire 812a (i.e., the wire depicted as the "upper" wire in FIG. 42A) will be moved into tension within the flexure member 842, while the lower wire 812b will have less or no tension. This downward movement of the distal handle portion 834 and difference in tension between the upper wire 812a and the lower wire 812b will pull or articulate the distal portion 804 of the catheter 802 in an upward configuration (still considering the orientation of FIG. 42A) due to the wires 812 being fixed within the proximal handle portion 836.

Similarly, upward movement of the distal handle portion 834 will place or pull the lower wire 812b in tension due to the flexibility of the flexure member 842, thereby, articulating the distal portion 804 of the catheter 802 downward. Likewise, the wires 812c and 812d (only shown in FIG. 44) channeled through the sides of the flexure member 842 will facilitate articulation of the distal portion 804 of the catheter 802 laterally with a similar arrangement. In this manner, fixing the wires 812 in the proximal handle portion 836 and spacing the wires 812 through the flexure member 842 facilitates the travel needed for effective articulation of the distal portion 804 of the catheter 802 in the opposite direction than the direction the distal handle portion 834 is articulated via the articulating handle member 832. It is noted that although the above-description of an articulating handle system 830 has been provided for a catheter, such as the catheter for delivering the medical device set forth above, the articulating handle system may also be employed with the sheath of the medical device delivery system previously set forth, or employed for any suitable purpose for which an articulating catheter may be desired.

Referring now to FIG. 45, medical device 900 is shown according to another embodiment of the present invention. It is noted that only a portion of the medical device 900 is shown in cross-section. The medical device 900 includes an occluder portion 902 and an anchor portion 904, similar to various embodiments previously described herein. The occluder portion 902 may include a plurality of occluder frame segments 906 and a tissue growth member 908. The anchor portion 904 may include a plurality of anchor frame segments 910 having engagement members 912 or nubs thereon. The engagement members 912 may be similar to those described with respect to other embodiments provided herein. As with previously described embodiments, the occluder portion 902 and the frame portion 904 may be separately and independently deployed.

An extension member 914 may be coupled to a distal end 916 of each anchor frame segment 910 and extend inwardly and proximally from adjacent the engagement members 912. For example, in one embodiment, the extension member 914 may include a filament or a wire coupled to an eyelet 918 (or other coupling member) associated with the frame segment 910. The extension member 914 may be configured, for example, to extend proximally from the distal end 916 of the anchor segment 910 and through a hub portion 920 that couples the various occluder frame segments 906 and anchor frame segments 910 together. In use, the extension members 914 may be displaced proximally to retract the anchor frame segments 910 for repositioning or recapture of the device 900. In one embodiment, the anchor frame segments 910 may be configured to be displaced primarily radially inwardly upon proximal displacement of the extension members 914. In another embodiment, the anchor frame segments 910 may be configured to roll into a catheter or other component of a delivery device, similar to other embodiments described herein.

Upon satisfactory deployment of the medical device 900 in an LAA, the extension members may be decoupled from the anchor frame segments 910. For example, the extension members 914 may be decoupled from their associated eyelets 918 and retracted from the device 900. In another embodiment, the extension members 914 may remain coupled with the eyelets 918 but trimmed or cut or released, such as at the proximal face of the medical device 900. While the extension members 918 act as structural members in tension to retract the anchor frame segments 910, they may also be configured to act as structural members in compression to push against the anchor frame segments 910 in certain embodiments. In the case that the extension members 914 also act as compression members, they may be pivotally coupled with the anchor frame segment 910.

Referring to FIG. 46, a medical device 930 according to another embodiment is shown. The medical device 930 includes an anchor portion including multiple anchor frame segments 932 (only one is shown for convenience) and an occluder portion with a tissue growth member 934 coupled directly with the anchor frame segments 932. Engagement members 936 may be formed on a distal and radially outward portion of the anchor frame segments 932. Extension members 938 may be coupled with the anchor frame segments 932 in a similar manner, and function substantially the same as, those described with respect to FIG. 45. In this embodiment, when the medical device 930 is deployed, if the physician desires to reposition to a more preferred location within the LAA, the extension member 938 may be pulled proximally to move the engaging members 938 from a tissue-engaging position to a tissue-nonengaging position. The physician may then reposition the occluder portion to a preferred position and then release the extension member 938 to allow the anchor frame segments 932 to self expand to move the engaging members 936 to the tissue-engaging position. This process may be repeated until the physician is satisfied with the location of the medical device 930 and, then, proceed to releasing the medical device 930 similar to that described in previous embodiments.

Referring to FIG. 47, a medical device 950 according to another embodiment is shown. The medical device 950 may include an occluder portion and an anchor portion. The anchor portion may include multiple anchor frame segments 952 with engagement members 936 extending from a radial distal end portion of the frame segments 952. The occluder portion may include a tissue growth member 934 coupled to a proximal face of the multiple anchor frame segments 952. In this embodiment, the medical device 950 is substantially the same as shown and described with respect to FIG. 46, except that instead of a discrete extension member (e.g., extension member 938 shown in FIG. 46), the anchor frame segment 952 includes a loop portion 954 (that exhibits an extension portion extending inwardly and proximally from adjacent the engagement members 952) that acts as, or functions similar to, the discrete extension member of the embodiments shown in FIGS. 45 and 46.

Figure 48:
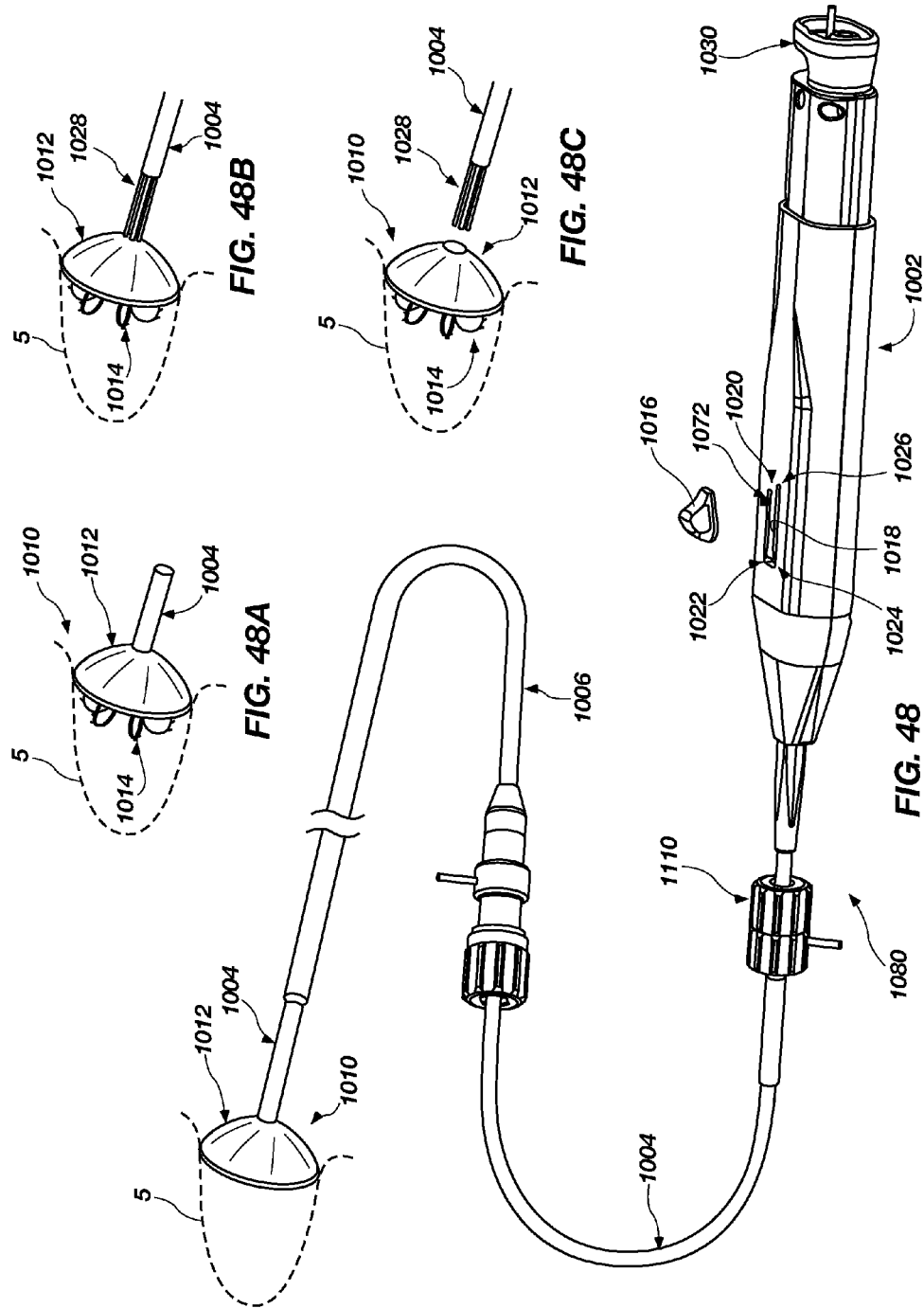
FIG. 48 is a perspective view of a handle of a medical device system, illustrating a deployed occluder portion of a medical device, according to one embodiment of the present invention.

Referring now to FIGS. 48 and 48A-48C, another embodiment of a medical device system 1000 configured to deliver and implant a medical device in the LAA 5 (shown in outline form) is shown. Similar to previous embodiments, the system 1000 includes a handle 1002, a delivery catheter 1004, a sheath 1006, and a medical device 1010 operatively coupled to the handle 1002, the medical device 1010 including an occluder portion 1012 and an anchor portion 1014. The handle 1002 is coupled to the delivery catheter 1004 and exhibits actuation functions that can be employed with one-hand that translates movements to the medical device 1010 and delivery catheter 1004 similar to previous embodiments. For example, the handle 1002 may include a single actuation knob 1016 or slider button that is moveable along a channel 1018 defined in the handle 1002 to actuate the anchor portion 1014 of the medical device 1010 and also withdraw the delivery catheter 1004 to place the medical device 1010 in a float mode (FIG. 48B). The channel 1018 may be u-shaped or j-shaped or the like. The actuation knob 1016 may be moved along the channel 1018 to various positions to control the medical device 1010, namely, the actuation knob may be moved to a first position 1020, a second position 1022, a third position 1024, and a fourth position 1026.

Movement of the actuation knob 1016 between the different positions provides similar functionality to that set forth in the previous embodiments of a handle. For example, with respect to FIGS. 48 and 48A, movement of the actuation knob 1016 between the first position 1020 and the second position 1022 moves the anchor portion 1014 between an anchors retracted position and an anchors deployed position (FIG. 48A), respectively. Movement of the actuation knob 1016 from the second position 1022 to the third position 1024 in the channel 1018 may lock the anchor portion 1014 to the anchors deployed position. Likewise, movement of the actuation knob 1016 from the third position 1024 to the second position 1022 will un-lock the anchor portion 1014 at the anchors deployed position to, thereby, enable a physician to retract the anchor portion 1014 to the anchors retracted position by moving the actuation knob 1016 back to the first position 1020. Also, the actuation knob 1016 in the third position 1024 in the channel 1018 enables a release mechanism in the handle (or provides the ability to release the medical device 1010) as well as enables a physician to place the medical device 1010 in a float mode (FIG. 48B). As depicted in FIGS. 48 and 48B, movement of the actuation knob 1016 between the third position 1024 and the fourth position 1026 moves the delivery catheter between an un-float mode (FIG. 48A) and a float mode (FIG. 48B), respectively. In other words, the delivery catheter 1004 moves or withdraws proximally relative to the medical device 1010, leaving only the tension of the tethers 1028 interconnected to the medical device 1010, thereby, placing the medical device 1010 in a float mode or a state with minimal tension on the medical device 1010 that may resemble the state or position of the medical device after release thereof. Further, as depicted in FIGS. 48 and 48C, the medical device 1010 can be released or detached from the medical device system 1000 via a release knob 1030. Additional detail will be set forth herein relating to the actuation of the handle 1002 to perform the various stages for deploying and releasing the medical device 1010 from the medical device system 1000.

Figure 49:
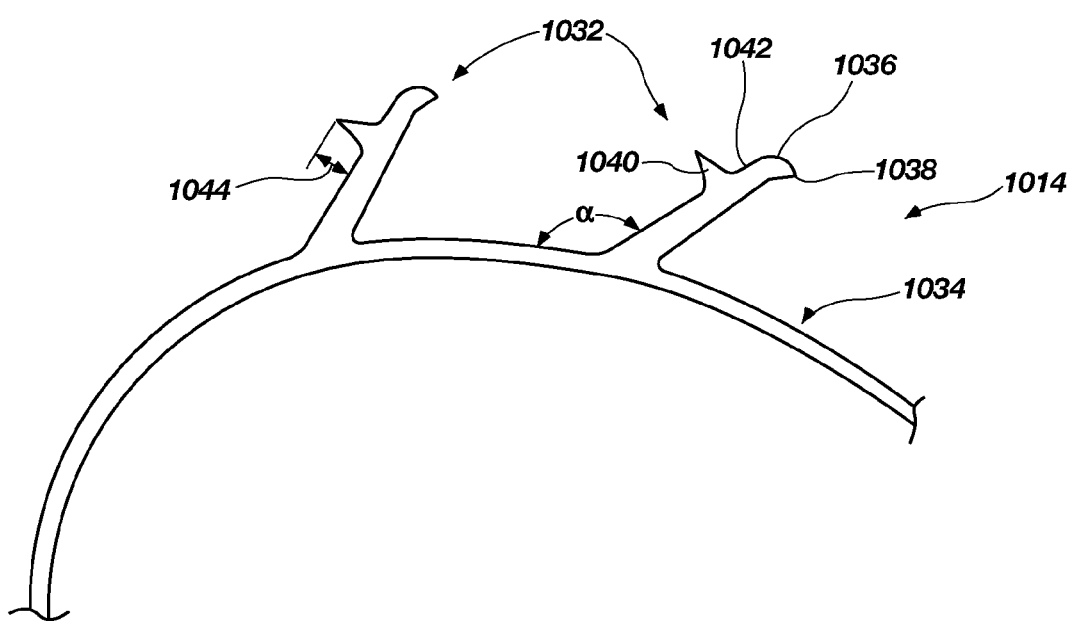
FIG. 49 is an enlarged partial profile view of an anchor loop of the medical device implant, according to an embodiment of the present invention.

FIG. 49 is an enlarged profile view of one embodiment of engaging members 1032 of the medical device 1010. A similar view of such engaging members 1032 is also found in FIG. 12A, of a previous embodiment provided herein. The medical device 1010 of this embodiment may include two or three or more engaging members 1032 on each anchor loop 1034 of the anchor portion 1014. Similar to the previous embodiment of the engaging members, the engaging members 1032 of this embodiment extend proximally at an angle α of about one-hundred thirty-five degrees from the tangent of the anchor loop 1034 from which it extends and includes a wave crest configuration with a peak portion 1036 and a descending tapered edge 1038 below the peak portion 1036. The peak portion 1036 may be rounded or blunt and the tapered edge 1038 is configured to engage tissue upon proximal movement of the medical device 1010. In addition, each engaging member 1032 of this embodiment may include a tine 1040 extending distally from a distal surface 1042 of the engaging member 1032. The tine 1040 may include a triangular profile. The tine 1040 may also include a height 1044 between 0.2 mm and 0.3 mm, and may also extend to a height 1044 between 0.1 mm and 0.35 mm. Further, the tine includes a depth (not shown) into the page with a dimension similar to that of the anchor loop 1034, set forth in previous embodiments. Such distally extending tine 1040 may be sized and configured to grab or engage tissue in the LAA upon distal movement of the medical device 1010. Further, the distal surface 1042 acts as a back-stop to tissue to which the distally extending tine 1040 may engage. With this arrangement, the engaging members 1032 of this embodiment are configured to stabilize the medical device 1010 in the LAA by aggressively engaging tissue and substantially prevent both proximal and distal movement of the medical device 1010 upon deploying the anchor portion 1014 in the LAA. Further, the engaging members 1032 are sized and configured to substantially prevent perfusions or piercing of the tissue of the LAA while also providing the traction to stabilize the medical device in the LAA. Furthermore, the self expanding radial force of the anchor loops 1034 bias the anchor loops 1034 against tissue of the LAA (toward a fully expanded position) while the engaging members 1032 are sized and configured and angled to be atraumatic or to not pierce the tissue, but rather, sized and configured to substantially prevent both proximal and distal movement of the device in the LAA.

Figure 50:
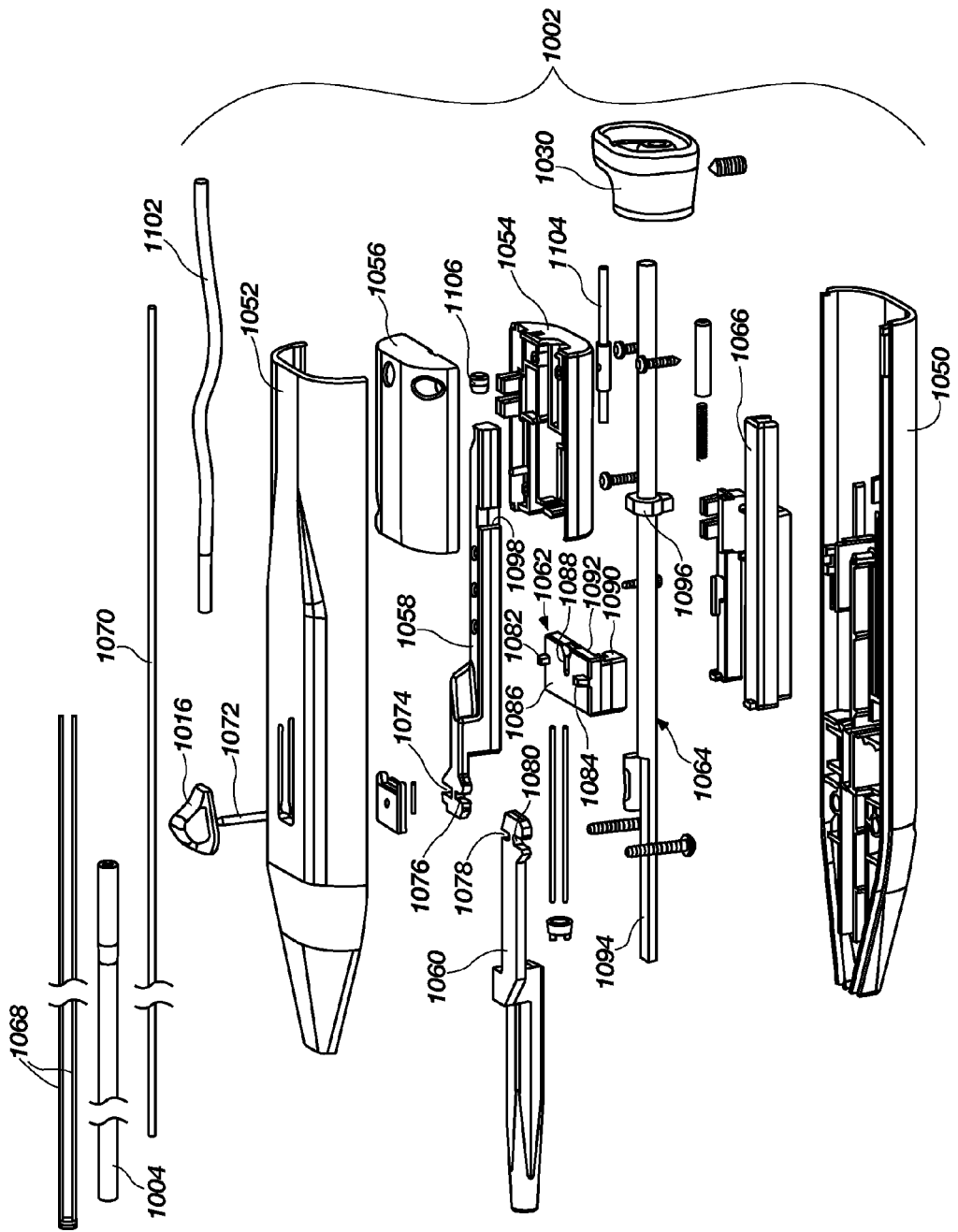
FIG. 50 is an exploded view of the medical device delivery system, according to an embodiment of the present invention.

In addition, although not shown, the anchor loops 1034 of this embodiment may include a wire coiled or wrapped around the anchor loops similar to that depicted in FIGS. 12B and 38. Such coiled wire provides a fail-safe feature to substantially prevent potential perfusions in the LAA over long periods of time if one of the anchor loops where to become fatigued and fracture. The coil being intended to substantially prevent any potential fractured portion of the anchor portion 1014 or anchor loops 1034 from extending from the coiled parameter and damaging tissue in the LAA. In this manner, the coiled wire around the anchor loops 1034 provides a fail-safe feature for the anchors portion. Further, parameters may be built-in the anchor portion, such as within the anchor loops adjacent to or in the hub, to allow breakage at locations where the strain is the greatest provide intended modes for failure. md FIG. 50 is an exploded view of the handle 1002 to illustrate the various components of the handle 1002 along with the components associated with the delivery catheter. For example, the handle 1002 may include a lower housing 1050 and an upper housing 1052 as well as a rear lower housing 1054 and a rear upper housing 1056 with the release knob 1030 at a proximal end of the handle 1002. Internal components of the handle 1002 may include an anchor operator 1058, a float operator 1060, a mode switch 1062, a release enable rod 1064, and an occluder release member 1066, each of which are sized and configured with structure of, for example, various latches, slots, notches and/or tabs to enable or lock-out the actuation functions of the medical device (not shown) and may be activated or implemented with the actuation knob 1016 and/or the release knob 1030. Also, the rear lower housing 1054 may include integrated molded components to act as an anchor release member.

Further, for example, the delivery catheter 1004 may include, similar to previous embodiments (e.g., FIG. 39) one or more occluder tethers 1068 and an anchor tether 1070 each configured to extend through discrete lumens defined longitudinally through the delivery catheter 1004 as well as release wires (not shown) extending through each of the occluder tethers 1068 and the anchor tether 1070 attached at one end to the medical device, and attached at the other end to the respective occluder release member 1066 and the rear lower housing 1054 or the anchor release member, discussed in more detail hereafter.

The actuation knob 1016 or slider button, positioned on the upper housing 1052, may be fixed to a pin 1072 that extends through the upper housing 1052 within the channel 1018 and may be configured to be manually moveable or slideable along the channel 1018 defined in the upper housing 1052. As the pin 1072 moves to and from the different positions in the channel 1018, the pin 1072 is configured to actuate each of the anchor operator 1058, mode switch 1062, and the float operator 1060 depending on the position of the actuation knob 1016 along the channel 1018, discussed in more detail hereafter.

The anchor operator 1058 may include a first slot 1074 and a second slot 1076 defined at a distal portion of the anchor operator 1058. Similarly, the float operator 1060 may include a first slot 1078 and a second slot 1080 defined in a proximal portion of the float operator 1060. The mode switch 1062 may include a first tab 1082 and a second tab 1084 extending from an upper side 1086 of the mode switch 1062 as well as a mode switch slot 1088 defined in the upper side 1086 of the mode switch 1062. Further, the mode switch 1062 also includes a lower shelf 1090 extending from a lower side 1092 of the mode switch 1062 in a j-shaped configuration sized and configured to interact with the release enable rod 1064 to prevent rotation of the release enable rod 1064 when the actuation knob 1016 is in the first position 1020 or second position 1022.

The first tab 1082 of the mode switch 1062 may be sized and configured to correspond with the first slot 1074 of the anchor operator 1058 and the second tab 1084 may be sized and configured to correspond with the second slot 1080 of the float operator 1060. The pin 1072, extending through the channel 1018 of the upper housing 1052, is sized and configured to slideably couple to the second slot 1076 of the anchor operator 1058, the mode switch slot 1088, as well as the first slot 1078 of the float operator 1060, each depending upon the position the actuation knob 1016.

The release knob 1030 may be fixed to the release enable rod 1064 and configured to be moved from a first release knob position to a second release knob position. From the initial position or first release knob position of the release knob, the release knob can rotate to the second release knob position and then may move linearly and proximally to a third release knob position or released position. The release enable rod 1064 also may include a flat portion 1094 along a distal portion thereof. Such flat portion 1094 is sized and configured to be positioned within or over the shelf 1090 of the mode switch 1062 when the actuation knob 1016 is at the first position 1020 and second position 1022 to prevent the release enable rod 1064 from rotating and, thereby, lock-out the ability to release the medical device 1010. The release enable rod 1064 also may include a latch 1096 fixed to the rod 1064 along an intermediate portion thereof. The latch 1096 is sized to correspond and engage with a notch 1098 in the anchor operator 1058 so that the anchor operator 1058 maintains a fixed linear position relative to the release enable rod 1064 through all positions of the actuation knob 1016 until the release enable rod 1064 is rotated via the release knob 1030, discussed in further detail below.

The handle 1002 also may include a flushing system configured to flush air from particular lumens or channels within the medical device system. The flushing system may include an input fluid port 1102, an intermediate tube 1104, one or more sealing rings 1106, the anchor tether 1070 and the delivery catheter 1004. The interconnection of the components for the flushing system will be discussed in detail hereafter.

Figure 51A:
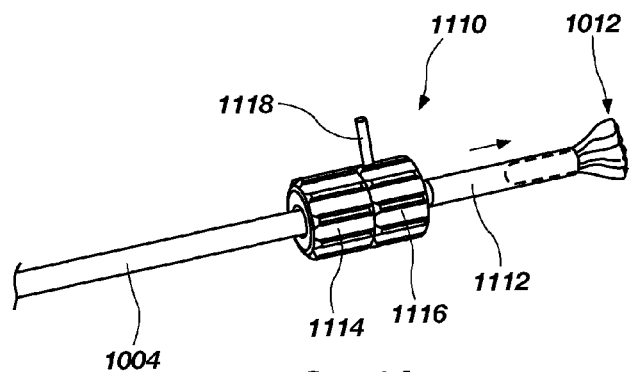
FIG. 51A is a perspective view of a loader, illustrating the loader being pushed over the occluder portion of the medical device, according to an embodiment of the present invention.

Referring now to FIGS. 48 and 51A, the medical device system 1000 may include a loader 1110 sized and configured to facilitate loading the occluder portion 1012 of the medical device 1010 into the sheath 1006 so that the delivery catheter 1004 can push the occluder portion 1012 through the sheath 1006 to a distal portion thereof. The loader 1110 may include a tubular configuration that may be slideably positioned over the delivery catheter 1004 such that the delivery catheter 1004 extends through a bore defined through the loader 1110. The loader 1110 may include a loader portion 1112, a rotatable valve 1114, and a body 1116 with a fluid port 1118 extending from the body 116. As depicted in FIG. 51A, the loader may be moved to the distal end of the delivery catheter 1004 and manually moved or forced over the occluder portion 1012 of the medical device 1010 so that occluder portion 1012 moves to a constricted position. The loader 1110 may move completely over the occluder portion 1012, at which point the medical device 1110 is prepared to be advanced through the sheath 1006.

Figure 51B:
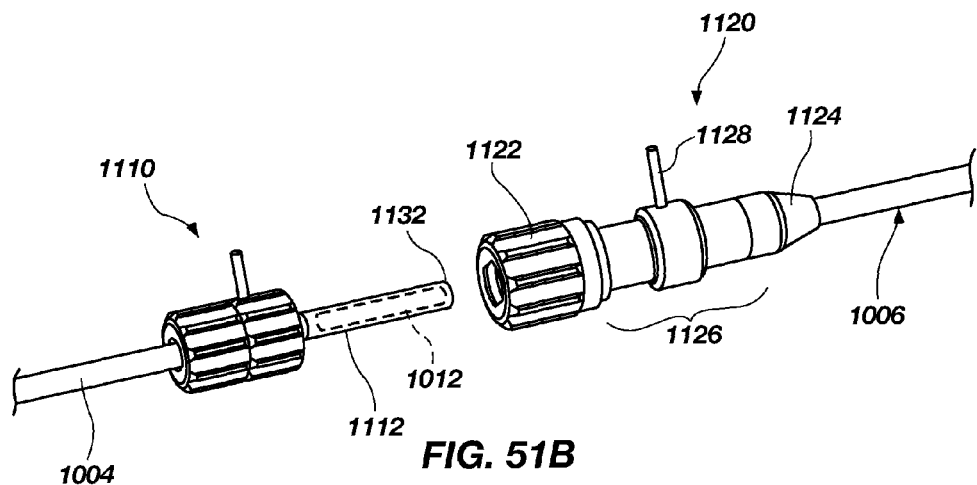
FIG. 51B is a perspective view of the loader aligned with a sheath hub and a sheath, according to an embodiment of the present invention.
Figure 51C:
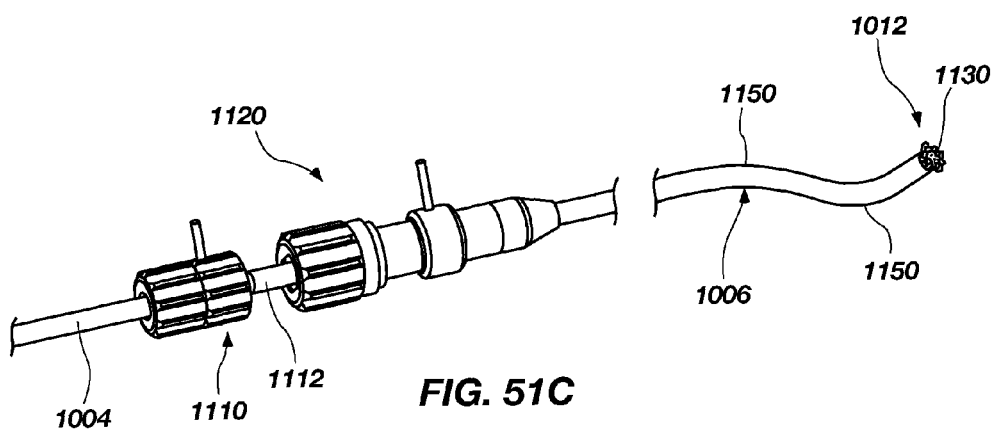
FIG. 51C is a perspective view of the loader inserted into the sheath hub with a portion of the occluder portion exposed at a distal end of the sheath, according to an embodiment of the present invention.

As depicted in FIGS. 51B and 51C, the loader 1110 may be inserted into the sheath 1006 and, more particularly, a sheath hub 1120. The sheath hub 1120 may be fixedly integrated at the proximal end of the sheath 1006. The components of the sheath hub 1120 may include a rotating valve 1122 and a hub tip 1124 with a hub portion 1126 extending therebetween. The rotating valve 1122 may be a rotating hemostasis valve, such as a Touhy Borst valve, configured to constrict back-flow of blood from the sheath 1006 upon rotation of the valve 1122. The hub tip 1124 may be fixed to a proximal end of the sheath 1006. The hub portion 1126 may include a fluid port 1128 extending from an intermediate location of the sheath hub 1120. The hub portion 1126 may be made from a transparent material configured to allow a physician to view air that may have been introduced into the system. If air is located, the physician may readily pull the air from the hub portion 1126 via the fluid port 1128 and be confident that the air has been removed due to the viewability of the transparent hub portion 1126.

As previously set forth, the loader 110 may be mated or inserted into the sheath hub 1120 with a snap or click fit via nubs 1132 at the distal end of the loader portion 1112 and a rib (not shown) within the sheath hub 1120. Once the loader 1110 is positioned within the sheath hub 1120, the delivery catheter 1004 may be advanced through the sheath 1006 such that the distal end of the delivery catheter 1004 moves to a distal portion of the sheath 1006 to expose a distal end of the occluder portion 1012 from the distal end of the sheath 1006. At this stage, the distal portion of the sheath 1006, with the occluder portion 1012 in its constricted state, may be positioned within the LAA. With this arrangement, the distal tip of the occluder portion 1012 is exposed at the distal end of the sheath 1006 and provides, due to the occluder material, a cushion tip 1130, without any exposed metal frame members, facilitating an atraumatic entry into the LAA, thereby, reducing the potential of perfusions in the LAA.

Figure 52A:
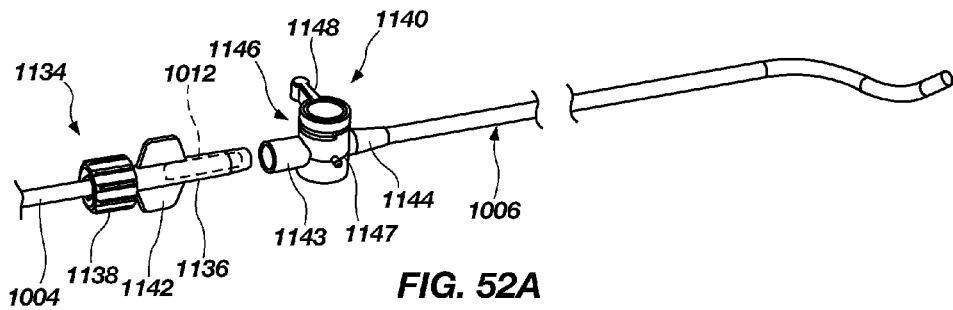
FIG. 52A is a perspective view of a loader and a sheath hub, according to another embodiment of the present invention.

With respect to FIG. 52A, another embodiment of a loader 1134 and a sheath hub 1140 is provided. The sheath hub 1140 of this embodiment includes a valve configuration 1146 that may be configured to prevent blood therethrough, facilitates removing air via a fluid port 1147, and can also be opened to facilitate the delivery catheter 1004 and occluder portion (not shown) to be pushed through the valve configuration 1146.

Similar to the previous embodiment, the loader 1134 may include a loader portion 1136 having a tubular configuration slidably moveable over the delivery catheter 1004. The loader 1134 also may include a rotatable valve 1138 and a grip portion 1142. The sheath hub 1140 may include a proximal portion 1143 and a distal portion 1144 with the valve configuration 1146 therebetween. The valve configuration 1146 may be manually moved between a closed position and an open position via a rotating member 1148. Such valve configuration 1146 may be employed for hemostasis, wherein the valve configuration 1146 may be moved to a closed position to substantially prevent the back-flow of blood through the sheath 1006.

Figure 52B:
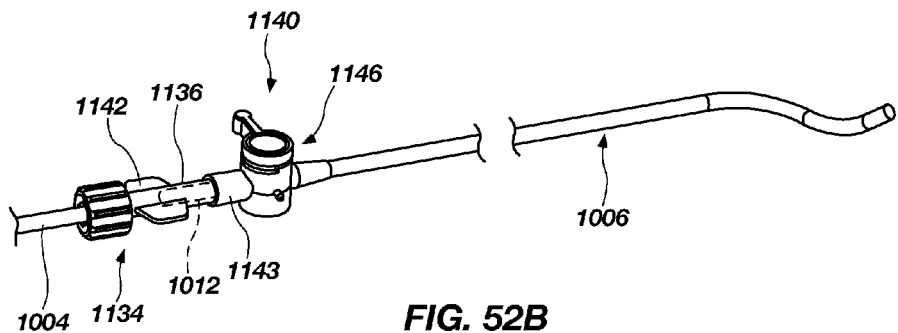
FIG. 52B is a perspective view of the loader inserted in the sheath hub, according to another embodiment of the present invention.
Figure 52C:
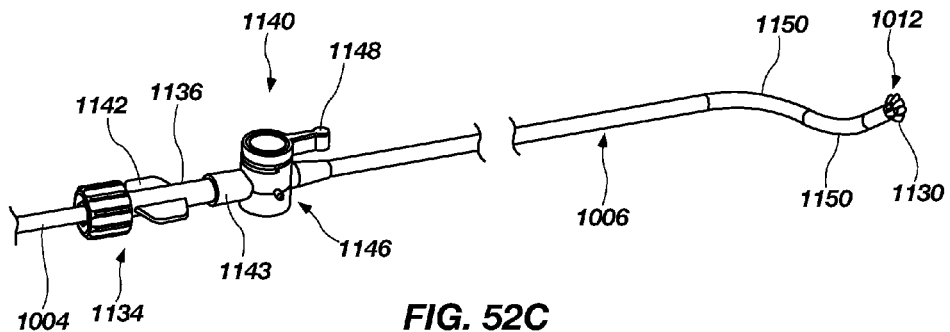
FIG. 52C is a perspective view of the loader inserted in the sheath hub with a medical device implant positioned at the distal portion of the sheath, according to an embodiment of the present invention.

For example, with respect to FIGS. 52A-52C, the loader 1134 may be pushed over the occluder portion 1012 of the medical device 1010 similar to that depicted in the previous embodiment. The valve configuration 1146 of the sheath hub may be in a closed position once the distal portion of the sheath 1006 has been advanced to the left atrium to provide hemostasis and prevent the back-flow of blood therethrough. The loader 1134 may then be inserted into or mated with the proximal portion 1143 of the sheath hub 1140. The grip portion 1142 may then be turned to secure the loader 1134 to the proximal portion 1143 of the sheath hub 1140 via windings formed on the loader portion 1136 and inside the proximal portion 1143 of the sheath hub 1140. The rotating member 1148 of the sheath hub 1140 may then be moved to the open position so that the delivery catheter 1004 and medical device 1010 can be advanced through the loader 1134, the sheath hub 1140 and to the distal portion of the sheath 1006 until a distal tip of the occluder portion 1012 of the medical device 1010 is slightly exposed at the distal end of the sheath 1006, similar to that depicted in FIG. 52C. At this time, the distal portion of the sheath 1006 can be advanced and positioned in the LAA in a safe manner with the cushion tip 1130 of the occluder portion 1012 exposed at the distal end of the sheath 1006.

Further, as depicted in FIGS. 51C and 52C, the distal portion of the sheath 1006 may include one or more bends 1150 that provide a favorable angle of approach to the LAA. Such sheath 1006 may be made from a polymeric material as known to one skilled in the art. The distal portion of the sheath 1006 may be heat-formed over a mandrel to form the one or more bends 1150. This heat-treating process may be employed by heating the mandrel first and then sliding the mandrel through the distal portion of the sheath 1006 to obtain hardening with the preferred one or more bends 1150. Another heat-treating process that may be employed is heating the distal portion of the sheath 1006 after the mandrel is positioned in the sheath 1006. In another embodiment, the distal portion of the sheath may be positioned in a clam-shell device and heated to obtain the one or more bends 1150 in the sheath 1006. Since the favorable angle of approach to the LAA may vary between patients, multiple sheaths 1006 may be provided to the physician with, for example, one bend, two bends, or three bends. In another embodiment, the sheath 1006 may include an articulating distal portion that may be manipulated by a physician at a proximal portion of the sheath, similar to that set forth relative to FIGS. 41-44 herein.

Detail will now be provided relating to the function of the various handle 1002 components employed relative to the functionality of the medical device 1010, namely, for delivering, positioning, deploying, floating, and releasing the medical device 1010 to and in an LAA. Referring first to FIGS. 48 and 53, the handle 1002 is in a first position or anchors retracted position such that the pin 1072 of the actuation knob 1016 is positioned in a first position along the channel 1018. It is in the first position or anchors retracted position that the handle 1002 is maintained when the device 1010 is advanced through the sheath 1006, as previously set forth relative to FIGS. 51 and 52, and as the occluder portion 1012 is deployed from the sheath 1006 in the LAA. Deployment of the occluder portion 1012 of the medical device 1010 may be controlled solely by manually withdrawing the sheath 1006, from which the occluder portion 1012 is configured to self expand in the LAA. Similarly, the occluder portion 1012 may be constricted by advancing the sheath 1006 back over the occluder portion 1012 should the physician desire to reposition the occluder portion 1012 within the LAA.

As illustrated in FIG. 53, in the anchors retracted position or first position 1020 of the handle 1002, the mode switch 1062 is also in a first mode switch position and the anchor operator 1058 may also be in a proximal or retracted position. The anchor operator 1058 may be maintained in the retracted position via the pin 1072 of the actuation knob (not shown) positioned in the second slot 1076 of the anchor operator 1058. Further, as depicted in FIGS. 53 and 53A, with the mode switch 1062 in the first mode switch position, the float operator 1060 is maintained in a distal position or non-retracted position via the second tab 1084 of the mode switch 1062 positioned in the second slot 1080 of the float operator 1060. Also, the flat portion 1094 of the release enable rod 1064 is positioned over the shelf 1090 or within the slot defined between the lower side 1092 and the shelf 1090 of the mode switch 1062 to prevent rotation of the release enable rod 1064. In other words, the shelf or slot is sized and configured to receive the flat portion 1094 of the release enable rod 1064 to facilitate linear movement of the release enable rod 1064 therethrough but not rotational movement. The release enable rod 1064 is coupled to the release knob 1030 at a proximal end thereof.

With respect to FIGS. 53 and 53B, the release enable rod 1064 also may include the latch 1096 fixedly coupled thereto. The latch 1096 may be fixed to the release enable rod at a position that corresponds with the notch 1098 defined in the anchor operator 1058. The latch 1096 may include a cam-like configuration with a first latch portion 1152 and a second latch portion 1154. The first latch portion 1152 may be sized and configured to correspond and be positioned within the notch 1098 of the anchor operator 1058. The functions of the first and second latch portions 1152, 1154 will be further described hereafter.

Now turning to FIGS. 54, 54A, 54B, description of handle 1002 components for flushing the handle 1002 will now be provided, FIG. 54 being an end view of the handle 1002 depicted in FIG. 53 and FIG. 54A being a cross-sectional view taken along section line 54A of FIG. 54. The handle 1002 components or flushing system for flushing the medical device system to substantially eliminate air within particular portions of the system when delivering the medical device may include the input fluid port 1102, the intermediate tube 1104, the anchor tether 1070 and the delivery catheter 1004. The input fluid port 1102 may feed through the release knob 1030 at a proximal side of the handle 1002. The input fluid port 1102 may be coupled to the intermediate tube 1104 that extends through both the release knob and is coupled to a proximal side of the rear lower housing 1054 through one or more sealing rings 1106 within the proximal end of the anchor operator 1058. Fluid may then pass through the anchor operator 1058 and, more specifically, through the anchor tether 1070.

As depicted in FIGS. 53B, 54A and 54B, the anchor tether 1070 may include a polymeric coating, which within the anchor operator 1058 its outer surface is sealed to an inner bore defined longitudinally through the anchor operator 1058. As such, fluid may be channeled from the intermediate tube 1104 directly through the anchor tether 1070 and continues directly to the primary or central lumen of the delivery catheter 1004. At a proximal portion of the delivery catheter 1004, the anchor tether 1070 may include a flush port (not shown) through the polymeric coating that facilitates fluid to exit the anchor tether 1070 and flow through both the lumens defined in the anchor tether 1070 and the primary or central lumen of the delivery catheter 1004 to ultimately exit at the distal end of the delivery catheter 1004.

Figure 55:
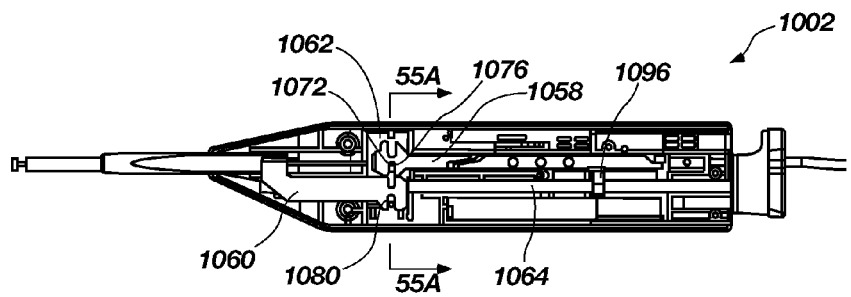
FIG. 55 is a side view of the handle (upper housing removed), illustrating the handle in a second position, according to another embodiment of the present invention.
Figure 55A:
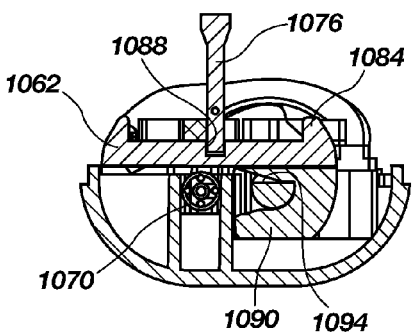
FIG. 55A is a cross-sectional view of the handle along section line 55A of FIG. 55, according to the present invention.

Now referring to FIGS. 48, 55 and 55A, the second position 1022 of the handle 1002 or anchors deployed position with the anchor operator 1058 in a distal position is provided. As previously set forth, the anchor tether 1070 may be directly coupled to the anchor operator 1058. As such, movement of the anchor operator 1058 from the proximal position (FIG. 53) to a distal position moves the anchor tether 1070 distally to, thereby, move the anchor portion 1014 of the medical device 1010 to a deployed position. Actuation of the anchor operator 1058 distally is employed by manual movement of the actuation knob 1016 from the first position 1020 to the second position 1022. The pin 1072, extending from the actuation knob 1016 through the channel 1018 defined in the upper housing 1052 (FIG. 48), is positioned in the second slot 1076 of the anchor operator 1058, which facilitates distal movement of the anchor operator 1058 to the mode switch slot 1088 defined in the mode switch 1062. With the mode switch 1062 in the first mode switch position, the actuation knob can be freely moved between the first position 1020 and the second position 1022 or, otherwise said, between the anchors retracted position and the anchors deployed position, respectively. Also, when the mode switch is in the first mode switch position, the second tab 1084 of the mode switch 1062, being coupled to the second slot 1080 of the float operator 1060, maintains the float operator 1060 in a fixed position. Further, movement between the first position 1020 and second position 1022 of the actuation knob 1016 of the handle 1002 also moves the release enable rod 1064 linearly over the shelf 1090 of the mode switch 1062 via the latch 1096 coupled to the anchor operator 1058. In this manner, the flat portion 1094 of the release enable rod 1064 can move linearly over the shelf 1090 of the mode switch 1062, but is prevented from rotational movement, while the mode switch 1062 is in the first mode switch position.

Figure 56:
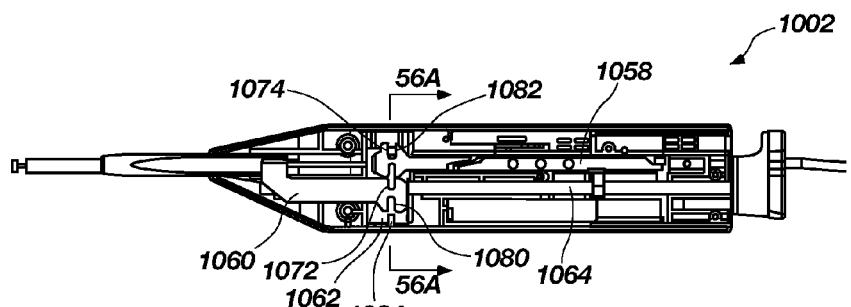
FIG. 56 is a side view of the handle (upper housing removed), illustrating the handle in a third position, according to another embodiment of the present invention.
Figure 56A:
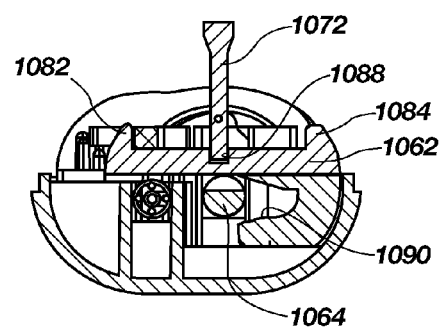
FIG. 56A is a cross-sectional view at section A of FIG. 56, illustrating a second mode switch position of the mode switch, according to an embodiment of the present invention.

With respect to FIGS. 48, 56 and 56A, the third position 1024 of the handle 1002 or anchors locked position is provided. The handle 1002 moves to the third position 1024 by moving the actuation knob 1016 from the second position 1022 to the third position 1024. Such movement of the actuation knob 1016 moves the mode switch 1062 from the first mode switch position to the second mode switch position via the pin 1072 positioned in the mode switch slot 1088. Further, movement of the mode switch 1062 to the second mode switch position or third position 1024 of the handle 1002 locks the anchor portion 1014 in the anchors deployed position via the first tab 1082 of the mode switch 1062 being moved into the first slot 1074 of the anchor operator 1058. Likewise, such movement removes the second tab 1084 of the mode switch 1062 from the second slot 1080 of the float operator 1060, thereby, enabling a physician to then actuate the float mode of the handle 1002. It should also be noted, once the mode switch 1062 is in the second mode switch position, the mode switch 1062 moves such that the release enable rod 1064 is no longer confined over the shelf 1090 or slot of the mode switch 1062, thereby, enabling the release enable rod 1064 to rotate via rotation of the release knob 1030 if desired. In other words, the steps necessary to release the medical device 1010 may be employed at any time once the mode switch 1062 is in the second mode switch position. Such steps for releasing the medical device 1010 will be discussed in further detail hereafter.

Figure 57:
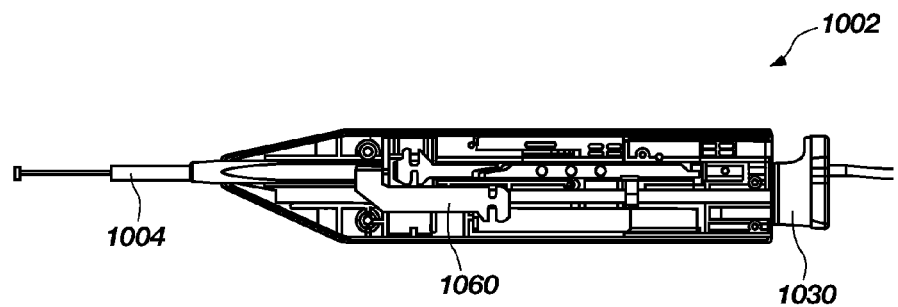
FIG. 57 is a side view of the handle (upper housing removed), illustrating the handle in a fourth position or float mode, according to an embodiment of the present invention.

Now turning to FIGS. 48 and 57, once the mode switch 1062 is moved to its second mode switch position, the float operator 1060 may be moved proximally via the actuation knob 1016 to the fourth position 1026 of the handle 1002. Movement of the actuation knob 1016 to the fourth position 1026 moves the float operator 1060 proximally, which also directly withdraws the delivery catheter 1004 proximally relative to the tethers 1028 and medical device 1010 (see FIG. 48B). Such movement places the medical device 1010 in a position in the LAA with minimal tension on the medical device 1010. The physician may then conduct a push-pull test on the device 1010 to determine if the medical device 1010 is stable in the LAA. If stable, the medical device 1010 may be released from the tethers 1028.

Figure 58:
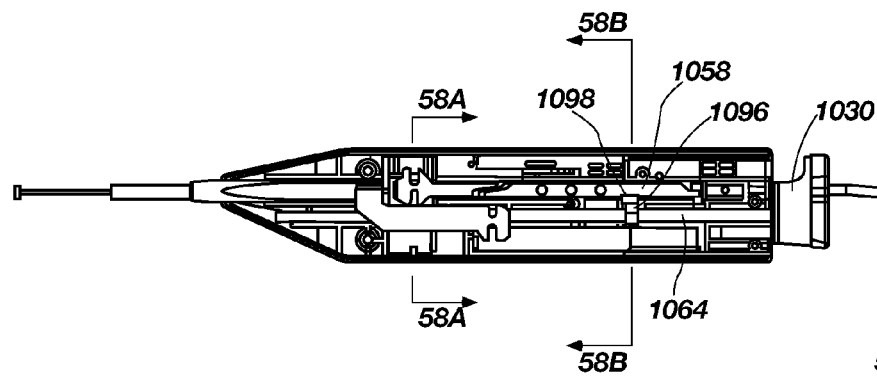
FIG. 58 is a side view of the handle (upper housing removed), illustrating a release knob in a rotated position or release enable position, according to an embodiment of the present invention.
Figure 59:
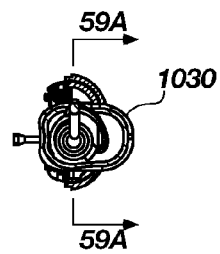
FIG. 59 is an end view of the handle of FIG. 58, according to the present invention.
Figure 58A:
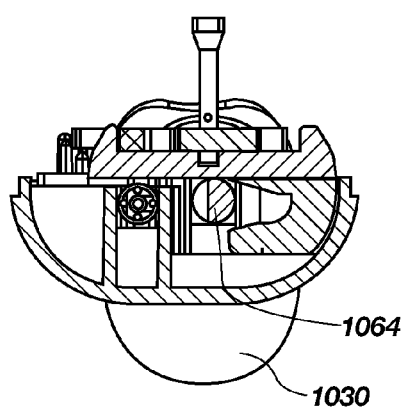
FIG. 58A is a cross-sectional view of the handle taken along section line 58A of FIG. 58, illustrating the release enable rod rotated, according to an embodiment of the present invention.
Figure 58B:
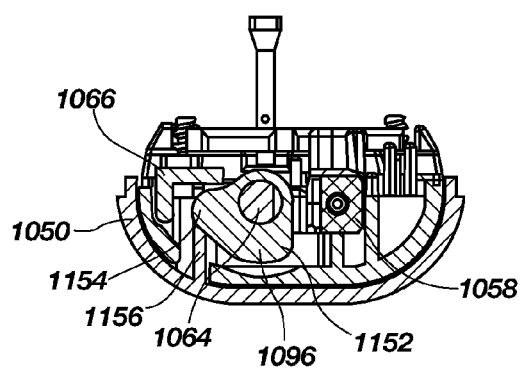
FIG. 58B is a cross-sectional view of the handle taken along section line 58B of FIG. 58, illustrating the latch in a rotated position, according to an embodiment of the present invention.

The medical device may be released from the tethers 1028 by employing a two step process. As depicted in FIGS. 58 and 59, the release knob 1030 has been rotated from a first release knob position (e.g., FIG. 57) to a second release knob position. The release knob 1030 may be moved to the second release knob position by rotating, for example, a quarter turn in the clock-wise direction. This rotated position of the release knob 1030 is a pre-step for detachment such that rotation enables or facilitates detachment of the tethers 1028 from the medical device 1010. As depicted in FIGS. 58 and 58A, rotation of the release knob 1030 also rotates the release enable rod 1064 since the release knob 1030 is fixed to the release enable rod 1064. As depicted in FIGS. 58 and 58B, rotation of the release enable rod 1064 also rotates the latch 1096 from a latched position with the anchor operator 1058, in which the first latch portion 1152 is moved from the notch 1098 of the anchor operator 1058 to, thereby, de-couple the anchor operator 1058 from the release enable rod 1064. Further, the second latch portion 1154 of the latch 1096 is moved against a protrusion 1156 of the lower housing 1050 which unlatches the occluder release member 1066 from the lower housing 1050 to, thereby, facilitate or enable the occluder release member 1066 to by-pass the protrusion 1156 and facilitate linear movement of the occluder release member 1066.

Figure 59A:
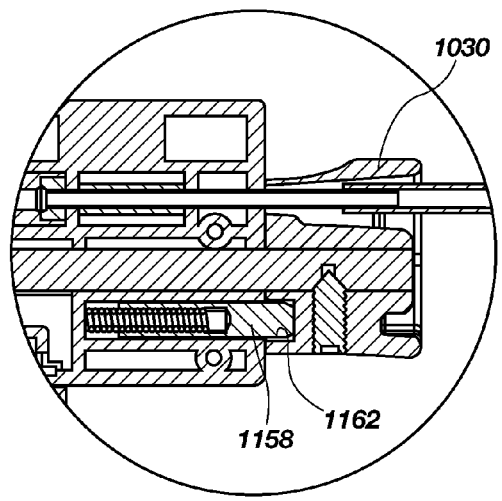
FIG. 59A is an enlarged partial cross-sectional view of the handle taken along line 59A of FIG. 59, illustrating the release knob and a spring-loaded pin in the rotated position, according to an embodiment of the present invention.
Figure 59B:
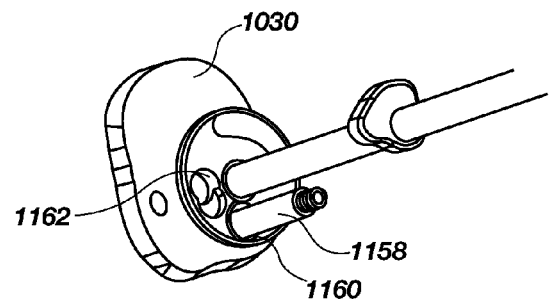
FIG. 59B is a distal side perspective view of the release knob and release enable rod without the handle, illustrating the spring-loaded pin and cavities defined in the release knob, according to an embodiment of the present invention.

As depicted in FIGS. 54B and 59A, the release knob 1030 is provided in a first release knob position and a second release knob position (or rotated position), respectively. In the first release knob position, the release knob 1030 includes a spring-loaded pin 1158 held in a tapered cavity 1160 defined in the release knob 1030. FIG. 59B depicts a distal side of the release knob 1030 exhibiting the spring-loaded pin 1158 positioned in the tapered cavity 1160. The tapered cavity 1160 facilitates the spring-loaded pin 1158 to contract and slide-out of the tapered cavity 1160 upon rotational force of the release knob 1030. As depicted in FIGS. 59A and 59B, such movement of the release knob to the second release knob position moves the spring-loaded pin 1158 in a second cavity 1162 that is non-tapered, thereby, substantially preventing the release knob 1030 from further rotation, such as, to its previous position. In this manner, once the release knob 1030 is rotated to the second release knob position, the non-tapered cavity of second cavity 1162 maintains or locks the release knob in the second release knob position. The medical device 1010 is then ready to be detached from the medical device system 1000.

Figure 60:
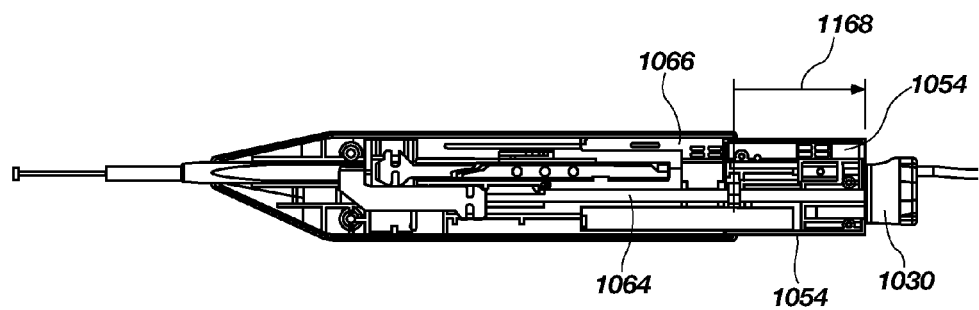
FIG. 60 is a side view of the handle (upper housing removed), illustrating the handle in a released position, according to an embodiment of the present invention.

As depicted in FIG. 60, the release knob 1030 may be moved linearly in a proximal direction, as indicated by arrow

1168. Such movement of the release knob 1030 also linearly moves the, release enable rod 1064, rear lower housing 1054 (and rear upper housing 1056) as well as the occluder release member 1066 in the proximal direction. Further, movement of the rear lower housing 1054 (or anchor release member) and occluder release member 1066 detaches the tethers 1028 from the medical device 1010 (FIG. 48C). The tethers 1028 (anchor tether and occluder tethers) each may include wires or, for example, the first wire 640 and the second wire 642, extending through coils of the tethers, coupled to the medical device 1010 in a similar manner to that previously set forth in FIG. 39. As previously set forth, the first wire 640 may be a pull wire and the second wire 642 may be a pin wire.

Figure 61:
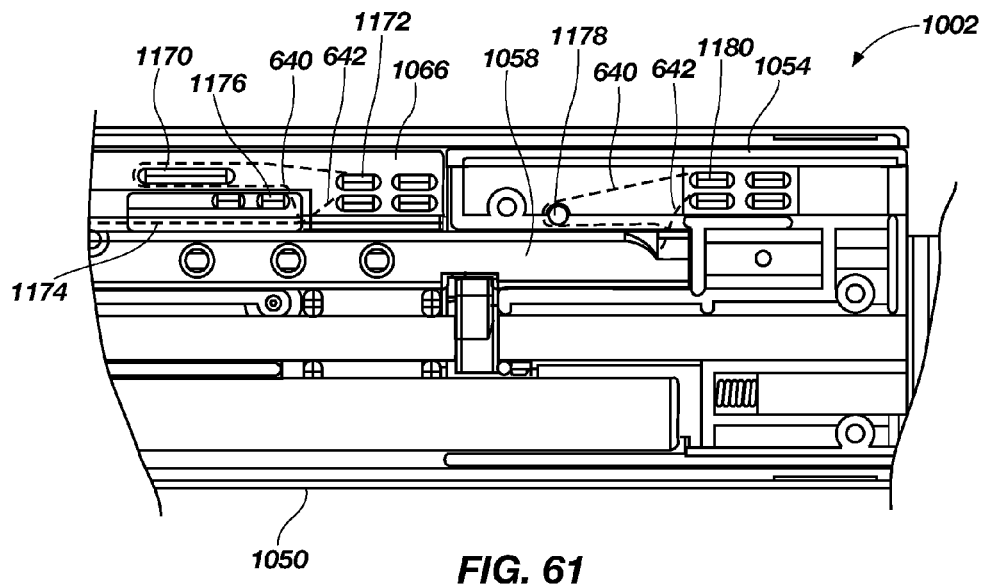
FIGS. 61 and 62 are enlarged side views of the handle (upper housing removed) in the non-released and released positions, respectively, illustrating the tether/wire windings in the handle to effect release, according to another embodiment of the present invention.
Figure 62:
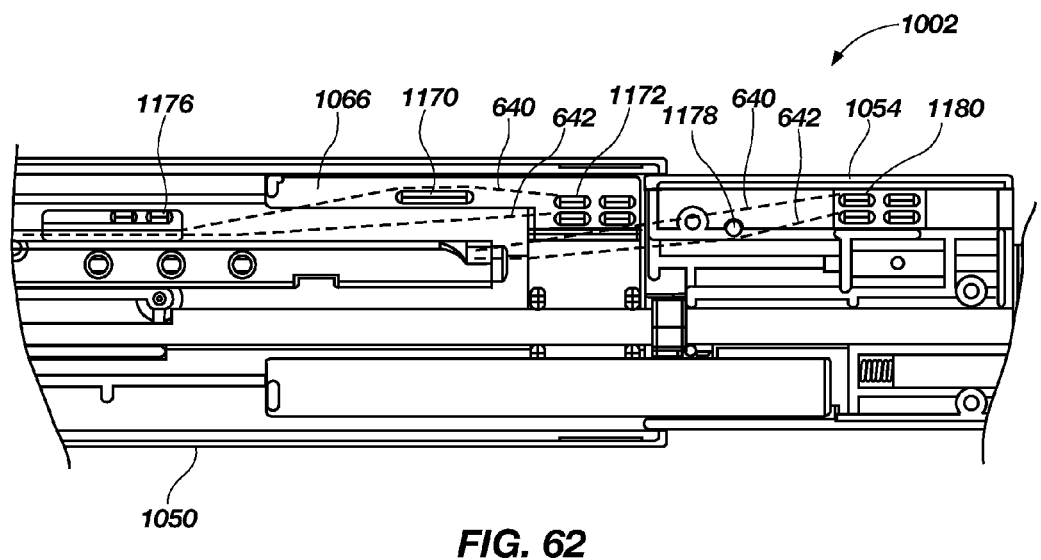

As depicted in FIGS. 61 and 62, enlarged side views of the handle (with the upper housing removed) are provided to illustrate the first wire 640 and second wire 642 (shown in outline form) in the handle 1002 at the first (or second) release knob position and the third release knob position, respectively. Each of the first and second wires 640, 642 for each tether extend through the delivery catheter (not shown) and into the handle 1002. In the handle 1002, the wires may be channeled around various structures of the lower housing 1050 of the handle 1002, occluder release member 1066 and the anchor release member 1054. For example, the occluder release member 1066 may include an occluder first post 1170 and an occluder second post 1172 for manipulating the wires. In addition, the lower housing 1050 may include an occluder fixed post 1176 and may include a channel 1178 defined in the lower housing 1050 for holding or channeling the occluder tethers (not shown). The anchor release member 1054 may also include anchor first post 1178 and an anchor second post 1180.

With respect to FIG. 61, the first and second wires 640, 642 may exit the occluder tether (now shown) at an end of the channel 1174 defined in the lower housing 1050. The first wire 640 for each occluder tether may extend out of the occluder tether/coil, around the occluder fixed post 1176, then around a distal end of the occluder first post 1170, and then extend to the occluder second posts 1172 to be fixed thereto. The second wire 642 for each occluder tether may extend out of the occluder tether/coil and directly to the occluder second post 1172 to be fixed thereto. A similar arrangement is provided for the first and second wires 640, 642 extending from the anchor tether (not shown). For example, as previously set forth, the anchor tether and coil extend into the anchor operator 1058. At a proximal end of the anchor operator 1058, the first wire 640 extends distally to and wraps partially around the anchor first post 1178 and then extends proximally to the anchor second posts 1180 to be fixed thereto. The second wire 642 of the anchor tether also extends from the proximal end of the anchor operator 1058 directly to the anchor second posts 1180 to be fixed thereto. With this arrangement, the first and second wires 640, 642 for each of the occluder tethers and the anchor tether are wound through the handle 1002 to facilitate detachment of the medical device upon linearly moving the release knob to the third release knob position, as previously described. Linear movement of the release knob simultaneously moves the occluder release member 1066 and the anchor release member 1054. Upon such linear movement, the slack built into the first wire 640 allows the second wire 642 to be moved first through the delivery catheter and from the medical device. In other words, because the second wire 642 for each of the occluder tethers and the anchor tether extends directly to the respective occluder second posts 1172 and anchor second posts 1180, the entire length of the second wires 642 move before the entire length of the first wires 640. The slack is built-in by the first wires 640 extending proximally to the respective occluder first post 1170 and the anchor first post 1178.

As depicted in FIG. 62, once the occluder release member 1066 and anchor release member 1054 linearly move a defined distance, the slack of the first wires 640 are overcome and the entire first wires 640 are also pulled through the tethers. The defined distance for the occluder release member 1066 to be moved may roughly be twice the distance between the distal end of each of the occluder first post 1170 and the occluder second post 1172, as positioned prior to linear movement (FIG. 61). Similarly, the defined distance for the anchor release member 1054 to be moved to overcome the slack in the wires may roughly be twice the distance between the anchor first post 1178 and anchor second post 1180, as positioned prior to linear movement of the anchor release member 1054 (FIG. 61). By pulling the second wire 642 or pin wire first before the slack in the first wires 640 is overcome, the first and second wires 640, 642 readily disengage or detach from the medical device, as depicted and set forth relative to FIG. 39. With this handle arrangement, as depicted in FIGS. 48C and 62, linear movement of the release knob substantially simultaneously detaches the tethers or, more specifically, the first and second wires 640, 642 from the occluder portion and anchor portion of the medical device.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A method for occluding a left atrial appendage of a heart, the method comprising:
  advancing a delivery catheter and medical device through a sheath to the left atrium of a heart and to a distal portion of the sheath, the medical device having an occluder portion and an anchor portion independently moveable between a non-deployed position and a deployed position;
  positioning the distal portion of the sheath within the left atrial appendage of the heart with both the occluder portion and anchor portion in the non-deployed position;
  withdrawing the sheath relative to the medical device to move the occluder portion of the medical device from the non-deployed position to the deployed position with the anchor portion maintaining the non-deployed position such that the anchor portion is proximal a most distal end of the occluder portion;
  actuating a portion of a handle operatively coupled to the medical device with distal movement to move the anchor portion distally from the non-deployed position to the deployed position while the occluder portion maintains the deployed position such that the anchor portion is moved from a proximal position to a distal position so that a portion of the anchor portion is distal the occluder portion;
  stabilizing the medical device in the left atrial appendage with the anchor portion engaging tissue in the left atrial appendage in the deployed position; and
  releasing the medical device from the delivery catheter in the left atrial appendage.

2. The method according to claim 1, wherein the positioning comprises exposing a distal end of the occluder portion from a distal tip of the sheath to expose a cushion tip without exposing any metallic portions of a frame of the medical device.

3. The method according to claim 1, wherein the actuating comprises moving an actuation element of the handle between a first position and a second position that corresponds with the non-deployed position and the deployed position of the anchor portion, respectively.

4. The method according to claim 3, wherein the actuating comprises moving the actuation element from the second position to a third position for locking-out actuation of the anchor portion of the medical device and enabling a float mode of the medical device.

5. The method according to claim 4, wherein the actuating comprises moving the actuation element from the third position to a fourth position for withdrawing the delivery catheter relative to the medical device to put the medical device in a float mode.

6. The method according to claim 1, further comprising floating the medical device by withdrawing the delivery catheter relative to the medical device to expose tethers coupled to the medical device.

7. The method according to claim 1, wherein the releasing comprises rotating a release knob and linearly moving the release knob to detach a coupling element from the medical device.

8. The method according to claim 1, wherein the stabilizing comprises atraumatically engaging tissue with engaging members that substantially minimize movement of the medical device in both a distal direction and a proximal direction.

9. The method according to claim 1, wherein subsequent to the stabilizing, further comprising modifying a position of the occluder portion in the left atrial appendage by actuating the portion of the handle to move the anchor portion from the deployed position to the non-deployed position.

10. A method of occluding a left atrial appendage of a heart, the method comprising:
providing a medical device having an occluder portion and an anchor portion, a handle having an actuation assembly, and a coupling member extending through a delivery catheter between the medical device and the actuation assembly of the handle;
advancing the medical device to the left atrial appendage through a sheath;
deploying the occluder portion in the left atrial appendage by withdrawing the sheath while the anchor portion maintains a retracted position such that the anchor portion is entirely proximal a most distal end of the deployed occluder portion;
moving an actuation element coupled to the actuation assembly from a first hard stop to a second hard stop so as to move the actuation element in a distal direction to move the anchor portion distally from the retracted position to a deployed position so that a portion of the anchor portion is distal the occluder portion while the occluder portion maintains a deployed position;
stabilizing the medical device in the left atrial appendage with the anchor portion engaging tissue in the left atrial appendage in the deployed position; and
releasing the medical device from the delivery catheter in the left atrial appendage.

11. The method according to claim 10, wherein the releasing comprises rotating a release knob to enable detachment of the medical device, and then linearly moving the release knob to detach the medical device from the coupling member extending through the delivery catheter.

12. The method according to claim 11, wherein the linearly moving the release knob comprises moving a pin wire and a pull wire operatively coupled to the release knob at the handle and directly coupled to the medical device.

13. The method according to claim 10, wherein the advancing comprises exposing a distal end of the occluder portion from a distal tip of the sheath to expose a portion of the occluder portion to provide a cushion tip without substantially exposing any metallic portions of a frame of the medical device.

14. The method according to claim 13, wherein the advancing comprises atraumatically positioning the distal tip of the sheath in the left atrial appendage with the cushion tip of the occluder portion exposed at the distal tip of the sheath.

15. The method according to claim 10, wherein the deploying the occluder portion further comprises movably positioning the occluder portion while in the deployed position in the left atrial appendage and while the anchor portion is in the retracted position.

16. The method according to claim 10, wherein subsequent to the stabilizing, further comprising moving the occluder portion to a different position in the left atrial appendage by actuating the handle to move the anchor portion from the deployed position to the retracted position.

17. The method according to claim 10, wherein the advancing comprises advancing the sheath into the left atrial appendage with a distal end of the occluder portion exposed from a distal tip of the sheath to provide a cushion tip without exposing any metallic portions of a frame of the medical device.

* * * * *